US010732115B2

(12) United States Patent
Wiesner et al.

(10) Patent No.: US 10,732,115 B2
(45) Date of Patent: Aug. 4, 2020

(54) MESOPOROUS OXIDE NANOPARTICLES AND METHODS OF MAKING AND USING SAME

(71) Applicant: Cornell University, Ithaca, NY (US)

(72) Inventors: Ulrich Wiesner, Ithaca, NY (US); Kai Ma, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/410,223

(22) PCT Filed: Jun. 24, 2013

(86) PCT No.: PCT/US2013/047313
§ 371 (c)(1),
(2) Date: Dec. 22, 2014

(87) PCT Pub. No.: WO2013/192609
PCT Pub. Date: Dec. 27, 2013

(65) Prior Publication Data
US 2015/0366995 A1 Dec. 24, 2015

Related U.S. Application Data

(60) Provisional application No. 61/662,999, filed on Jun. 22, 2012.

(51) Int. Cl.
*G01N 21/64* (2006.01)
*A61K 9/51* (2006.01)
*A61K 49/00* (2006.01)
*A61K 47/69* (2017.01)

(52) U.S. Cl.
CPC ........ *G01N 21/6486* (2013.01); *A61K 9/5115* (2013.01); *A61K 9/5146* (2013.01); *A61K 47/6935* (2017.08); *A61K 49/0041* (2013.01); *A61K 49/0093* (2013.01); *Y10T 428/2982* (2015.01)

(58) Field of Classification Search
CPC .............. A61K 9/5115; A61K 31/00; A61K 47/48907; A61K 9/5146; A61K 49/0054; A61K 47/48953; G01N 21/6486; Y10T 428/2982
See application file for complete search history.

(56) References Cited

U.S. PATENT DOCUMENTS

2008/0287288 A1* 11/2008 Ying .................. B82Y 10/00 502/159
2010/0035365 A1 2/2010 Wiesner et al.
2010/0331436 A1* 12/2010 Qiu ..................... C08G 61/10 521/124

FOREIGN PATENT DOCUMENTS

| CN | 102320612 | 1/2012 |
|---|---|---|
| WO | 03037297 | 5/2003 |
| WO | 2005000740 | 1/2005 |
| WO | 2011099932 | 8/2011 |
| WO | 2011/133925 A2 | 10/2011 |
| WO | WO 2011/133925 A2 * | 10/2011 |
| WO | 2012/075087 A2 | 6/2012 |
| WO | 2011062217 | 9/2012 |

OTHER PUBLICATIONS

Slowing et al. ("Mesoporous Silica Nanoparticles for Drug Delivery and Biosensing Applications," in Advanced Functional Materials, 2007, 17, pp. 1225-1236.*
Febvay et al. "Targeted Cytosoli Delivery of Cell-Impermeable Compounds by Nanoparticle-Mediated, Light-Triggered Endosome Disruption," Nano Letters, Mar. 6, 2010.*
Kim et al., Multifunctional Uniform Nanoparticles Composed of a Magnetite Nanocrystal Core and a Mesoporous Silica Shell for Magnetic Resonance and Fluorescence Imaging and for Drug Delivery, Angewandte Chemie Int'l Ed., vol. 47, No. 44, pp. 8438-8441. Oct. 20, 2008.
He et al., Mesoporous silica nanoparticle based nano drug delivery systems: synthesis, controlled drug release and delivery, pharmacokinetics and biocompatibility, J. of Materials Chemistry, vol. 21, No. 16, pp. 5845-5855. Jan. 1, 2011.
Meng et al., Use of Size and a Copolymer Design Feature to Improve the Biodistribution and the Enhanced Permeability and Retention Effect of Doxorubicin-Loaded Mesoporous Silica Nanoparticles . . . , ACS Nano, vol. 5, No. 3, pp. 4131-4144. May 24, 2011.
Slowing, I,, et al., Mesoporous Silica Nanoparticles for Drug Delivery and Biosensing Applications, Advanced Functional Materials, Mar. 20, 2007, vol. 17, pp. 1225-1236.
Lin, Y-S., et al., Impacts of Mesoporous Silica Nanoparticle Size, Pre Ordering, and Pore Integrity on Hemolytic Activity, J. Am. Chem. Soc., Mar. 15, 2010, vol. 132, pp. 4834-4842.
Tang, F., et al., Mesoporous Silica nanoparticles: Synthesis, Biocompatibility and Drug Delivery, Advanced Materials, Feb. 29, 2012, vol. 24, pp. 1504-1534.
He, Q., et al., The effect of PEGylation of mesoporous silica nanoparticles on nonspecific binding of serum proteins and cellular responses, Biomaterials, Oct. 31, 2009, vol. 31, pp. 1085-1092.
Ma et al., Controlling growth of ultrasmall sub-10nm fluorescent mesoporous silica nanoparticles, Chemistry of Materials, vol. 25, Iss. 5, pp. 677-691. Feb. 11, 2013.

(Continued)

*Primary Examiner* — Blessing M Fubara
(74) *Attorney, Agent, or Firm* — Hodgson Russ LLP

(57) ABSTRACT

Mesoporous oxide nanoparticles, compositions comprising such nanoparticle, and methods of making and using such nanoparticles. The nanoparticles (e.g., compositions comprising the nanoparticles) have an average size of less than 15 nm and a narrow size distribution. The nanoparticles can be used in imaging applications and delivery of molecular cargo (e.g., a drug) to an individual.

26 Claims, 31 Drawing Sheets

(56) References Cited

OTHER PUBLICATIONS

Ma et al., Ultrasmall Sub-10nm Near-Infrared Fluorescent Mesoporous Silica Nanoparticles, JACS, vol. 134, Issue 32, pp. 13180-13183. Jul. 25, 2012.
Burns et al., Fluorescent Silica Nanoparticles with Efficient Urinary Excretion for Nanomedicine, Nano letters, vol. 9, Iss. 1, pp. 442-448. Dec. 19, 2008.

* cited by examiner

MESOPOROUS OXIDE NANOPARTICLES AND METHODS OF MAKING AND USING SAME

CROSS-REFERENCE TO RELATED APPLICATIONS

This application claims priority to U.S. Provisional Application No. 61/662,999, filed on Jun. 22, 2012, the disclosure of which is incorporated herein by reference.

STATEMENT REGARDING FEDERALLY SPONSORED RESEARCH

This invention was made with government support under contract no. Grant Number MPS/DMR-1008125 awarded by the National Science Foundation. The United States Government has certain rights in the invention.

FIELD OF THE DISCLOSURE

The present disclosure generally relates to mesoporous oxide nanoparticles having a size of, e.g., 3 nm to 15 nm and a narrow size distribution. More particularly, the disclosure relates to compositions comprising such nanoparticles, and methods of making and using such nanoparticles.

BACKGROUND OF THE DISCLOSURE

Cancer has become a leading cause of death worldwide, accounting for over 7.5 million deaths in 2008. While one of the most important forms of cancer treatment, chemotherapeutic drugs often also kill healthy cells and cause toxicity to the patient. In the search for improved alternatives nanocarriers have become an emerging platform for cancer therapy enabling drug delivery specifically into tumors. Beginning in the mid-1980s, several types of targeting nanocarriers, based on polymer-protein conjugates and lipids, have successfully reached clinical trials. However, there are still many challenges remaining, including rapid clearance, burst drug release and non-specific uptake. In order to overcome these challenges, nanocarriers with better properties need to be designed. A promising alternative material to polymers is mesoporous silica due to its high-surface area, stability and bio-compatibility. Surface-functionalized mesoporous silica nanoparticles (MSNs) can deliver multiple types of cargo, such as DNA, drug molecules or even quantum dots, into cells and tissues of plants or animals. However, in the current state of development such MSN-based nanocarriers have not yet reached clinical trials. One of the reasons is that silica typically needs a fairly long time to dissolve under physiological conditions, resulting in potential particle accumulation in the body, which may in turn cause long-term toxicity. Even in cases where MSNs dissolve quite rapidly, questions about the dissolution mechanism, bio-distribution and toxicity remain.

In order to endow ultra-small silica nanoparticles with additional, e.g. therapeutic properties for clinical applications it is desirable to develop mesoporous particles with sizes smaller than 10 nm. Although recently the size of MSNs has been pushed down to less than 20 nm, the synthesis of fluorescent MSNs smaller than 10 nm and with narrow particle size distributions still remains a challenge.

BRIEF SUMMARY OF THE DISCLOSURE

In an aspect, the present disclosure provides a composition comprising polyethylene-glycol (PEG) functionalized mesoporous oxide (e.g., silica) nanoparticles having an average size of 15 nm or less, at least 90% of the nanoparticles are within 3 nm of the average size, and at least a portion of the non-pore surface is at least partially functionalized with polyethylene glycol groups. The oxide nanoparticles can be metal oxide nanoparticles, non-metal oxide nanoparticles, or mixed metal non-metal nanoparticles, or a combination thereof. The nanoparticles have a porous morphology and can have 1 to 5 pores per particle. A plurality of the nanoparticles have a single pore.

The nanoparticles can be functionalized. For example, at least a portion of the individual nanoparticle non-pore surface and at least a portion of the individual nanoparticle pore surface are functionalized. The at least a portion of the nanoparticle non-pore surface and the at least a portion of the pore surface can have different functionalization.

The nanoparticles can comprise a molecular cargo. For example, in a composition comprising the nanoparticles, at least a portion of the nanoparticles comprise a molecular cargo. For example, the molecular cargo is a therapeutic agent, prophylactic agent, or a fluorescent dye. The molecular cargo can be covalently bonded (e.g., via a linker) to at least a portion of the pore surface and/or non-pore surface of the nanoparticles. The molecular cargo can be sequestered in a pore of the nanoparticles.

In an aspect, the disclosure provides a method for making the polyethylene glycol (PEG) functionalized mesoporous oxide (e.g., silica) nanoparticles having an average size of 15 nm or less, at least 90% of the nanoparticles are within 3 nm of the average size, and at least a portion of the non-pore surface is at least partially functionalized with polyethylene glycol groups comprising the steps of: a) forming a reaction mixture in an aqueous solvent having a basic pH comprising: i) a surfactant, and ii.) an oxide precursor (e.g., a silica precursor such as TMOS); b) holding the reaction mixture at a temperature and for a time such that mesoporous oxide (e.g., silica) nanoparticles are formed; c) adding a PEG-functionalized oxide (e.g., a PEG-functionalized silica) precursor, d) holding the reaction mixture at a temperature and for a time such that the PEG-functionalized mesoporous oxide (e.g., silica) nanoparticles are formed; e) optionally, holding the PEG-functionalized mesoporous oxide (e.g., silica) nanoparticles at a temperature 50° C. to 95° C. for 0.5 to 24 hours; f) cooling the reaction mixture to room temperature; and g) removing the surfactant from the nanoparticles.

The methods can further comprise the step of functionalizing the nanoparticles. For example, the PEG-functionalized nanoparticles are contacted with a fluorescent dye conjugated oxide precursor such that at least a portion of the pores are functionalized with a fluorescent dye. As another example, the PEG-functionalized nanoparticles are contacted with a molecular cargo such that at least a portion of the molecular cargo is sequestered in the pores of the nanoparticles.

In another aspect, the disclosure provides methods of using the (PEG) functionalized mesoporous oxide (e.g., silica) nanoparticles. The nanoparticles can be used in imaging methods and molecular cargo delivery methods.

For example, a method for delivering a molecular cargo to an individual comprises: administering to an individual a composition comprising polyethylene-glycol (PEG) functionalized mesoporous oxide (e.g., silica) nanoparticles having an average size of 15 nm or less, at least 90% of the nanoparticles are within 3 nm of the average size, and at least a portion of the non-pore surface is at least partially functionalized with polyethylene glycol groups comprising a molecular cargo, wherein at least a portion of the molecular cargo is released in the individual. In this method, the molecular cargo can be a therapeutic agent or prophylactic agent.

DETAILED DESCRIPTION OF THE DISCLOSURE

Figure 1:
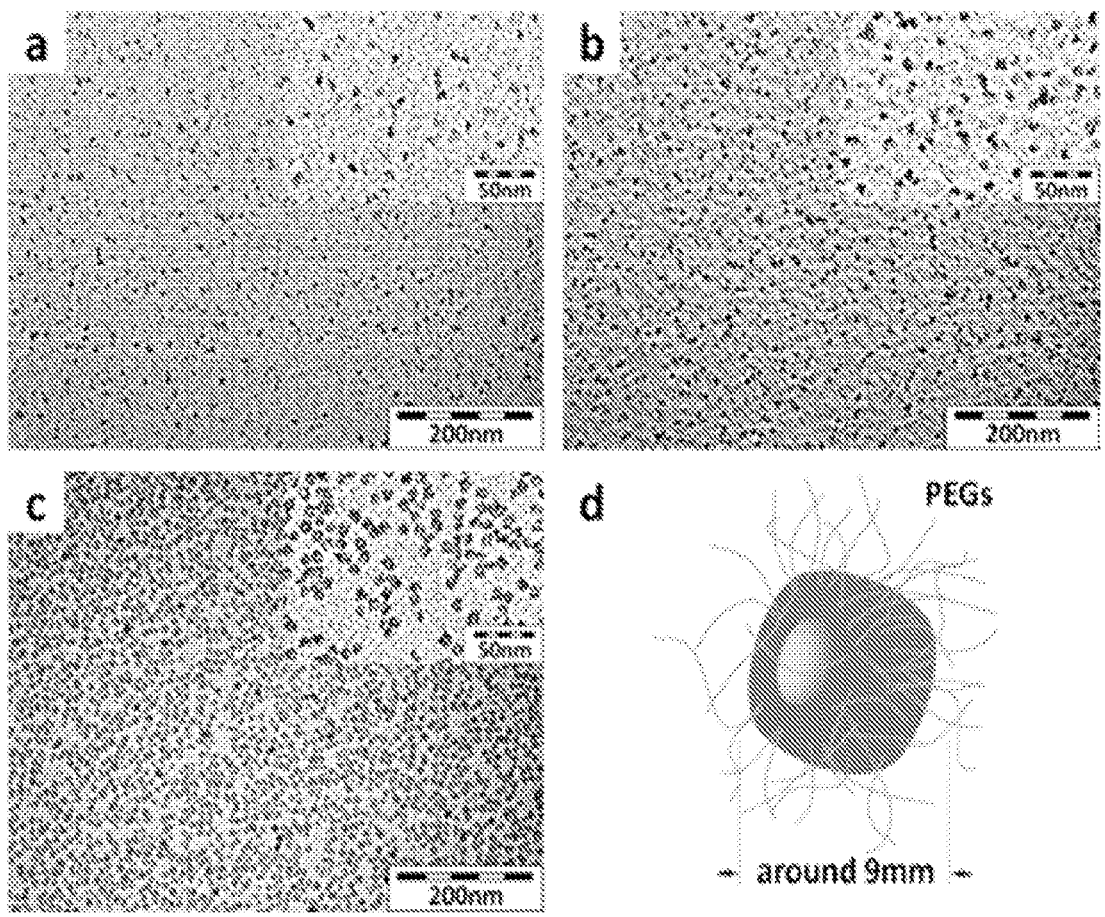
FIG. 1 shows representative TEM images of silica particles with different diameters: (a) 6.6 nm, (b) 8.2 nm and (c) 9.3 nm. Inserts display images of the same samples but at higher magnification. (d) Schematic of a single-pore MSN coated with PEG chains.

The present disclosure provides polyethylene glycol (PEG)-functionalized mesoporous oxide nanoparticles and compositions comprising such nanoparticles. Also provided are methods of making the nanoparticles and uses of the nanoparticles.

The nanoparticles (e.g., the nanoparticles in the compositions) have a narrow size distribution. The narrow size distribution can be realized by adding a PEG-functionalized oxide precursor to the nanoparticle reaction mixture at a selected time after the nanoparticle reaction forming reaction has started. It is desirable to make such compositions without the need for filtration or other similar separation techniques. In an embodiment, the nanoparticles (e.g., compositions comprising the nanoparticles) are formed without the need for filtration or other similar separation techniques.

In an aspect, the disclosure provides compositions comprising PEG-functionalized mesoporous oxide nanoparticles (nanoparticles are also referred to herein as mC dots). In an embodiment, the compositions comprise a plurality of such nanoparticles. The nanoparticles have an average size of 15 nm or less. At least a portion of the non-pore surface is functionalized with polyethylene glycol groups.

The PEG-functionalized mesoporous oxide nanoparticles can be non-metal oxide nanoparticles, metal oxide nanoparticles, or mixed non-metal and metal oxide nanoparticles. An example of non-metal oxide nanoparticles is silicon oxide nanoparticles (also referred to herein as silica nanoparticles). Examples of metal oxide nanoparticles include aluminum oxide nanoparticles, titanium oxide nanoparticles, niobium oxide nanoparticles, zinc oxide nanoparticles, iron oxide nanoparticles, and calcium phosphate nanoparticles. Examples of mixed non-metal and metal oxide nanoparticles include aluminosilicate nanoparticles and calcium phosphate/silica composites.

The PEG-functionalized mesoporous oxide nanoparticles have a range of sizes. The nanoparticles can have an average size of 3 nm to 15 nm, including all values to the 0.1 nm and ranges therebetween. In an embodiment, the nanoparticles have an average size of 3 nm to 12 nm. In various embodiments, the nanoparticles have an average size of 15 nm, 12 nm or less, 10 nm or less, 8 nm or less, 6 nm or less, or 4 nm or less. The nanoparticles (e.g., compositions comprising the nanoparticles) have a narrow size distribution. By "narrow size distribution" it is meant that the polydispersity index (PDI) of the nanoparticles is 0.2 or less. In various embodiments, the PDI is 0.005 to 0.2, including all values to 0.001 and ranges therebetween. In an embodiment, the PDI is 0.01 to 0.2. PDI as used herein is $\sigma^2/Z_D^2$, where $\sigma$ is the standard deviation of the nanoparticle size and $Z_D^2$ is the intensity weighted mean hydrodynamic size of the nanoparticles. In various embodiments, at least 80%, 85%, 90%, 95%, 96%, 97%, 98% or 99% of the nanoparticles are within 3 nm of the average nanoparticle size. In an embodiment, 100% of the nanoparticles are within 3 nm of the average nanoparticle size. The nanoparticle size can be measured by methods known in the art such as dynamic light scattering or microscopy (e.g., transmission electron microscopy).

The PEG-functionalized mesoporous oxide nanoparticles have a porous morphology. The nanoparticles can have multiple pores or a single pore. Without intending to be bound by any particular theory, it is considered that surfactant micelles can provide a template for nanoparticle formation that provides nanoparticles having multiple pores or single pores. The nanoparticles can have 0 to 5 pores per nanoparticle, including all portions of a pore and ranges therebetween. The pores can have a longest dimension (e.g., diameter in the case of a spherical pore) of 1 nm to 6 nm, including all values to the 0.1 nm and ranges therebetween. In an embodiment, the pores are asymmetrical (e.g., the width of the pore is longer than the length of the pore. In an embodiment, the pores have a width of about 3 nm and a length of about 3 nm, where about means the diameter and/or length can be 15% greater or less than 3 nm. In an embodiment, the composition comprises a plurality of the nanoparticles having a single pore.

The PEG-functionalized mesoporous oxide nanoparticles have a pore surface. The pore surface is also referred to herein as the interior surface. The nanoparticles also have a non-pore surface. The non-pore surface is also referred to herein as the exterior nanoparticle surface.

The non-pore surface of the PEG-functionalized mesoporous oxide nanoparticles is at least partially functionalized with PEG groups. The PEG groups are covalently bonded to the surface of the nanoparticle. For example, the PEG groups are covalently bonded to the surface via a Si—O—C bond. The PEG groups are derived from PEG polymer having a molecular weight (Mw) of 400 g/mol to 650 g/mol, including all integer g/mol values and ranges therebetween. In an embodiment, the PEG groups are derived from PEG polymer having a Mw of 460 g/mol to 590 g/mol, which contain 6 to 9 ethylene glycol units. In various embodiments, the nanoparticles are at least 50%, at least 75%, at least 90%, or at least 95% functionalized with PEG groups. In an embodiment, the nanoparticles are functionalized with PEG groups with the maximum number of PEG groups such that the pores remain accessible (e.g., the pores can be functionalized). In an embodiment, the pore surface is a silica surface having terminal silanol (Si—OH) groups.

The PEG-functionalized mesoporous oxide nanoparticles can be functionalized. By "functionalized" it is meant that a surface of the nanoparticle can have functional groups other than those resulting from the synthesis of the nanoparticles (e.g., —OH groups (resulting from terminal Si—OH groups on a nanoparticle surface) and PEG groups (resulting from Si-PEG groups on the nanoparticle surface). Such functionalization and functionalization methods are known in the art.

In an embodiment, at least a portion of the individual nanoparticle non-pore surface and at least a portion of the individual nanoparticle pore surface are functionalized. In an embodiment, at least a portion of the nanoparticle non-pore surface and the at least a portion of the pore surface have different functionalization.

The pore surface (e.g., at least a portion of the pore surface) and/or the non-pore surface (e.g., at least a portion of the non-pore surface) of the nanoparticles can be functionalized. For example, the nanoparticles can be reacted with compounds such that a functional group of the compound is presented on (e.g., covalently bonded to) the surface of the nanoparticle. The surface can be functionalized with hydrophilic groups (e.g., polar groups such as ketone groups, carboxylic acid, carboxylate groups, and ester groups), which provide a surface having hydrophilic character, or hydrophobic groups (e.g., nonpolar groups such as alkyl, aryl, and alkylaryl groups), which provide a surface having hydrophobic character. Such functionalization is known in the art. For example, diethoxydimethylsilane (DEDMS) is condensed on at least a portion of the pore surface such that the pore surface has hydrophobic character, allowing increased loading performance of a hydrophobic molecular cargo relative to nanoparticles that are not functionalized so.

The nanoparticles can comprise a molecular cargo. In an embodiment, at least a portion of the nanoparticles comprise a molecular cargo. In an embodiment, the composition comprises at least two different nanoparticles where the nanoparticles have different molecular cargo. In an embodiment, the composition comprises nanoparticles have at least two different molecular cargoes (e.g., a mixture of molecular cargoes). For example, 80% or more of the nanoparticles has accessible well-developed pores that can load one or more molecular cargo. By "well-developed pores" it is meant that pores have a desirable shape that is not blocked by PEG groups on the nanoparticle surface.

Examples of molecular cargoes include functional compounds such as fluorescent dyes, therapeutic agents, prophylactic agents, and mixtures thereof. Examples of suitable fluorescent dyes include near infrared (NIR) dyes such as Cy5, Cy5.5, blue dyes such as 7-diethylaminocoumarin-3-carboxylic acid, succinimidyl ester (DEAC), and green dyes such as tetramethylrhodamine (TMR). Fluorescent dyes used in biological imaging can be used. Examples of suitable therapeutic agents and/or prophylactic agents include antibiotics, chemotherapeutic agents, biologics such as peptides and antibody or antigen-binding compositions, nutraceuticals, vaccines, adjuvants, vitamins, minerals, growth factors, hormones, analgesics, compounds which affect cardiovascular, neurological or muscular function, or any other compound (e.g., a small molecular compound) that is intended to have an effect on a body, organ, tissue, cell or cellular component.

The molecular cargo can be covalently bonded to at least a portion of the pore surface and/or non-pore surface of a nanoparticle. In an embodiment, the molecular cargo is covalently bonded to at least a portion of the pore surface via a linker. Suitable linkers and conjugation methods are known in the art. For example, a thiol maleimide reaction or a N-hydroxysuccinimide (NHS) esters amine reaction can be used to provide a molecular cargo covalently bonded to the pore surface and/or non-pore surface of a nanoparticle. In another example, a biocleavable group (e.g., a disulfide) can be used as a linker group to provide controlled release of the molecular cargo from the nanoparticle.

The molecular cargo can be sequestered (e.g., non-covalently loaded) in a pore of a nanoparticle. By "sequestered" it is meant that the molecular cargo is at least partially encapsulated by a pore of a nanoparticle. In an embodiment, the molecular cargo is completely encapsulated a pore of a nanoparticle. For example, a hydrophobic molecular cargo can be loaded in a pore of the nanoparticle despite the low solubility of such a cargo in water.

In an embodiment, the nanoparticles are functionalized with gate-keeper groups (e.g., additional PEG pore surface functionalization) that block the pore entrances. The gate keeper groups can be cleavable gate-keeper groups (e.g., PEG groups) that can be cleaved to provide controlled release of the molecular cargo.

In an embodiment, the molecular cargo is a fluorescent dye. For example, the molecular cargo can be present in the nanoparticle matrix (i.e., dispersed in the oxide (e.g., silica)) or covalently bonded to a surface of the nanoparticle.

Nanoparticles comprising a fluorescent dye can be fluorescent and exhibit fluorescence at a wavelength depending at least on the nature of the fluorescent dye. In an embodiment, the nanoparticles comprise two or more fluorescent dyes where the dyes have different fluorescence wavelengths. Such nanoparticles can be suitable for fluorescence imaging applications. For example, the dye can be conjugated to a silane that is condensed on at least a portion of a surface of the nanoparticle.

The non-pore (exterior) surface can be functionalized with functional groups for specific applications. In an embodiment, the non-pore (exterior) surface is at least partially functionalized with targeting groups for specific diseases or targets related to a disease state. For example, the non-pore (exterior) surface is functionalized with cancer targeting agents (e.g., a cancer targeting ligand is conjugated to one terminus of a heterobifunctinal PEG group via a thiol maleimide reaction and the other terminus is conjugated to a silane via N-hydroxysuccinimide (NHS) esters amine reaction and the silane condensed on the surface of the nanoparticle (e.g., via a thiol) via a such that the nanoparticles have tumor targeting properties. Suitable, cancer targeting ligands include cRGDy and αMSH peptides.

The nanoparticles can have combinations of functionalization and molecular cargo. For example, at least a portion of the pore surface of a nanoparticle is functionalized to provide a surface (e.g., pore cavity) having hydrophobic character and a hydrophobic molecular cargo is sequestered in the pore.

The compositions can comprise a plurality of PEG-functionalized mesoporous oxide nanoparticles. The compositions can comprise a mixture of nanoparticles. For example, the compositions comprise nanoparticles having different nanoparticle composition and/or different functionalization. In an embodiment, a composition comprising PEG-functionalized mesoporous oxide nanoparticles does not have observable aggregates. Aggregation can be observed by methods known in the art such as transmission electron microscopy.

The nanoparticles can be made by methods disclosed herein. In an embodiment, the PEG-functionalized mesoporous oxide nanoparticles are made by a method disclosed herein.

In an aspect, the disclosure provides methods of making PEG-functionalized mesoporous oxide nanoparticles. The methods are based on fast hydrolysis of the oxide precursor (e.g., silica precursor(s)) to allow for near homogeneous nucleation (it is desirable to have fast hydrolysis in order to synthesize small oxide (e.g., silica) nanoparticles having narrow size distributions), slow oxide precursor (e.g., silica source) condensation to control the growth rate, and capping of particle growth/size by adding PEG-functionalized oxide precursor (e.g., PEG-silane) at selected time points to control size. Precursors are also referred to herein as sources. In an embodiment, the nanoparticles are nanoparticles are those described herein.

In an embodiment, the method of making the polyethylene glycol (PEG) functionalized mesoporous oxide nanoparticles comprises the steps of: forming a reaction mixture in an aqueous solvent having a basic pH comprising: a surfactant and oxide precursor(s) (e.g., a silica source such as tetramethoxy orthosilicate (TMOS)), holding the reaction mixture at a temperature and for a time such that mesoporous oxide nanoparticles are formed, adding a PEG-functionalized oxide precursor (e.g., a PEG-functionalized silane), holding the reaction mixture at a temperature and for a time such that the PEG functional mesoporous oxide nanoparticles are formed, cooling the reaction mixture to room temperature, and removing the surfactant from the nanoparticles.

Optionally, the method comprises the step of holding the PEG-functionalized mesoporous oxide nanoparticles at an elevated temperature. For example, the nanoparticles are held at 50° C. to 95° C., including all integer ° C. values and ranges therebetween, for 0.5 to 24 hours, including all 0.1 hour values and ranges therebetween. Without intending to be bound by any particular theory, it is considered this optional step facilitates condensation of PEG-functionalized oxide precursor with the surface of the mesoporous oxide nanoparticles. For example, PEG-functionalized mesoporous silica nanoparticles are held at a temperature of 80° C. for 24 hours.

It is desirable to use an oxide precursor (e.g., a silica source such as TMOS) that is water soluble and has a high hydrolysis rate under the reaction conditions. It is also desirable, that a high surfactant (e.g., an alkyl ammonium halide surfactant such as CTAB) to oxide precursor (e.g., silica precursor) ratio is used such that the nanoparticles have a desirable pore morphology. It is also desirable, that the reaction mixture have a composition such that the oxide precursor (e.g., silica precursor) condensation rate is favorable (e.g., a low ammonium hydroxide concentration). It is also desirable, that a high PEG-functionalized oxide precursor (e.g., PEG-functionalized silane) to oxide precursor (e.g., silica precursor) ratio be used such that nanoparticles having a narrow size distribution are formed.

The pH of the reaction mixture can range from neutral (pH 7) to slightly basic. The reaction mixture can be held at a temperature of 20° C. to 95° C., including all integer ° C. values and ranges therebetween, for 0.1 to 24 hours, including all 0.1 hour values and ranges therebetween.

The PEG-functionalized oxide precursor (e.g., PEG-functionalized silicon oxide precursor (also referred to herein as a PEG-functionalized silane)) is added to quench the reaction. For example, the PEG-functionalized oxide precursor (e.g., PEG-functionalized silicon oxide precursor) is added to the reaction mixture after the oxide precursor (e.g., silicon oxide precursor) hydrolysis and condensation reactions have started or when a desirable average nanoparticle size and/or porous morphology is present in the reaction mixture (e.g., after 0.1 minute to 24 hours of reaction time). Suitable PEG-functionalized precursors can be formed by conjugating a suitably functionalized PEG group to an oxide precursor. Such PEG-functionalized precursors are known in the art. Also, such functionalized PEG groups and methods of conjugating the functionalized PEG groups to oxide precursors is known in the art.

The reaction mixture can further comprise a molecular cargo. For example, the reaction mixture includes a fluorescent dye and the method provides fluorescent nanoparticles.

Determination of the reaction conditions (e.g., reaction time and temperature) required to make nanoparticles of a desired size are within the purview of one having skill in the art.

The method can include a step (or steps) where the PEG-functionalized mesoporous silica nanoparticles are functionalized. For example, the nanoparticles are functionalized such that the pore-surface and/or non-pore surface has functional groups or the nanoparticles have a molecular cargo (e.g., a molecular cargo covalently bonded to the pore-surface and/or non-pore surface or sequestered in a pore of the nanoparticle). Methods on nanoparticle functionalization are known in the art. Any methods compatible with the PEG-functionalized mesoporous silica nanoparticles can be used.

In an embodiment, the PEG-functionalized nanoparticles are contacted with a fluorescent dye conjugated silane precursor such that at least a portion of the pores are functionalized with a fluorescent dye. Examples of suitable fluorescent dye conjugated silane precursors and methods of fluorescent dye conjugated silane precursors are known in the art.

In an aspect the disclosure provides uses of the nanoparticles (e.g., compositions comprising a plurality of the nanoparticles). Examples of uses of the nanoparticles include methods for delivering a molecular cargo to an individual and imaging methods.

In an embodiment, a method for delivering a molecular cargo to an individual comprises administering to an individual a composition comprising polyethylene-glycol (PEG) functionalized mesoporous oxide nanoparticles comprising a molecular cargo, wherein the molecular cargo is released in the individual. For example, the molecular cargo is a therapeutic agent or prophylactic agent.

The compositions can be administered by any suitable means. Examples of suitable means include parenteral, subcutaneous, intraperitoneal, intrapulmonary, intranasal, topical and oral administration. Parenteral infusions include intramuscular, intravenous, intraarterial, intraperitoneal, or subcutaneous administration. The compositions can be formulated into any suitable formulation, including but not necessarily limited to pharmaceutical formulations, and thus can comprise any pharmaceutically acceptable stabilizers, excipients, carriers and the like. The compositions can be provided as a solution, suspension, emulsion, dispersion, or as a powder, pill, tablet or capsule.

The individual can be any human or non-human animal. In an embodiment, the human or non-human animal is a mammal. In an embodiment, the composition is useful for therapeutic or prophylaxis for non-human animals (e.g., non-human mammals).

In an embodiment, a method for imaging comprises the steps of administering to an individual a composition comprising polyethylene-glycol (PEG) functionalized mesoporous oxide nanoparticles comprising a molecular cargo capable of producing an image, and obtaining an image of the individual.

In another embodiment, the method comprises steps of contacting a cell or plurality of cells with a composition comprising polyethylene-glycol (PEG) functionalized mesoporous oxide nanoparticles comprising a molecular cargo capable of producing an image, and obtaining an image of the cell or plurality of cells. In an embodiment, the composition comprises nanoparticles having two or more fluorescent dyes. For use of the compositions in bioimaging methods, the composition can be contacted with cells which are to be imaged. For example, cells can be incubated with the composition. Upon incubation, the nanoparticles enter the cells and the cells can then be visualized for imaging. Methods using nanoparticles in imaging applications are known in the art.

The image can be obtained by any suitable method used to detect fluorescence from an individual or a cell. Suitable methods are known in the art. For example, a fluorescence microscope, a multiphoton microscope, a confocal microscope, epifluorescence, two photon, or any other in vitro or in vivo imaging method can be used. Additionally computer aided analysis can be used to image or quantitate the fluorescence. An imprint of the fluorescence can be recoded digitally. By this method, the morphology of the cells can be studied.

The present method can be used to diagnose a disease, disorder, or condition. Target cells can be visualized in culture, but can also be visualized in vivo. Therefore, it is not necessary that the cells be removed from the body. Animal cells or tissues may be labeled and imaged in situ. The target cells or tissue may be contacted with the composition and imaged without disrupting the surrounding tissue or cells. A disease, disorder or condition that is characterized by a change in cell morphology, cell permeability or other parameter that can be detected by staining may be diagnosed according to the present method. For imaging cells in vivo, the composition can be administered by any standard method.

Examples of cells that can be studied by the method of the present invention include, but are not limited to, prokaryotic cells, eukaryotic cells, mammalian cells, and plant cells. Examples of mammalian cells include fibroblasts, epithelial cells, neural cells, intestinal cells, embryonic and adult stem cells, ovarian cells, liver cells, prostate cells, kidney cells, bladder cells, blood cells, yeast cells, bacteria cells, and immune cells. Additionally, cell lines including immortalized cells, can also be studied. Such cells include but are not limited to: HeLa, KB, UC1-107, MCF-7, Mia-Paca, Pac-1, TE-671, etc.

The steps of the method described in the various embodiments and examples disclosed herein are sufficient to carry out the methods of the present disclosure. Thus, in an embodiment, the method consists essentially of a combination of the steps of the methods disclosed herein. In another embodiment, the method consists of such steps.

The following examples are presented to illustrate the present disclosure. They are not intended to limiting in any manner.

Example 1

This example shows sub-10 nm mesoporous silica nanoparticles (mC-dots) with a narrow size distributions and homogeneous porous particle morphology. Key features are (i) fast hydrolysis of a silane precursor to allow for near homogeneous nucleation, (ii) slow condensation to control the growth rate, and (iii) capping of particle growth by addition of a PEG-silane at specific time-points of the synthesis to control size.

By specifically varying these three steps, control over average particle size ranging from 6 to 15 nm, with increments below 1 nm, have been achieved. This addition of PEG allows for the synthesis of sub 10 nm particles without aggregation. Dynamic light scattering (DLS) and transmission electron microscopy (TEM) measurements have confirmed these particle sizes.

These mC-dots can be differentially functionalized so that the outer surface of the particle can have one functional motif while the inner pore contains a different functional motif. The inner pore as well can be used to transport therapeutic molecules or other material and compounds. The mC-dots can also have fluorescent dyes encapsulated within them such as blue [DEAL], green [TMR] and near infrared [Cy5.5]), which are useful in diagnostic as well as other uses. These particles can also be used for a combined diagnostic and therapeutic use.

These mC-dot particles around and below 10 nm are useful for sensing, drug delivery, therapeutic/diagnostic, research, and other applications.

Ultra-small nanoprobes have been made containing a single pore, tunable sizes around 12 nm and less with narrow size distributions that can be labeled with dye such as Cy5.5. Particles are characterized by a combination of transmission electron microscopy, dynamic light scattering, fluorescence correlation spectroscopy and optical spectroscopy. The ability to distinguish an "inside" and "outside" render these particles an interesting subject for use in sensing, drug delivery, research, theranostics (therapeutic and/or diagnostic), and other applications.

In this example, a one-pot synthesis of PEGylated MSNs with sizes precisely tunable around 9 nm (FIG. 1) that have narrow particle size distributions, a single pore and can be labeled with dye, such as near infrared (NIR) dye Cy5.5 is presented. Keys for the successful synthesis of such ultrasmall MSNs are (i) fast hydrolysis of the silica (silane) precursors, (ii) slow silica condensation/particle growth, and (iii) particle growth termination via the addition of PEG-silane quenching further silica condensation on the particle surface.

One embodiment of the synthesis was performed near room temperature (30° C.) in aqueous solution in the presences of hexadecyltrimethyl ammonium bromide (CTAB) as structure directing agent, with tetramethyl orthosilicate (TMOS) as silica source and ammonium hydroxide as base catalyst. PEG-silane was added directly into the synthesis batch to quench particle formation. A post-synthesis heating step and subsequent solution work-up, including acid extraction of CTAB via dialysis, provided the final particles.

While tetraethyl orthosilicate (TEOS) is commonly used in the synthesis of MSNs, here TMOS was chosen as the silica source. The hydrolysis rate of TMOS is much faster than that of TEOS and its solubility in water is higher. As a result, instead of forming a second oil-phase and gradually hydrolyzing at the oil droplet-water interface like in the case of TEOS, TMOS directly dissolves in water and hydrolyzes once added into the reaction. An accelerated completion of the hydrolysis process helps initiating/nucleating more MSN growth in the presence of CTAB micelles over a smaller period of time thus leading to smaller particles and better control over particle size distribution. Lowering the condensation rate by moving to near room temperature conditions or lowering the concentration of TMOS and CTAB results in slower particle growth and smaller particles. By carefully optimizing the system, conditions where the particles grow from around 2 nm to sizes larger than 10 nm within a convenient time window were found. Particle growth is terminated by quenching further condensation on the particle surface through addition of PEG-silane. A final heat-treatment at 80° C. at the end of the synthesis improves particle stability. Through the PEGylation step as part of the one-pot synthesis the resulting sub-10 nm MSNs are already sterically stabilized, a prerequisite for working in many biological environments.

Figure 2:
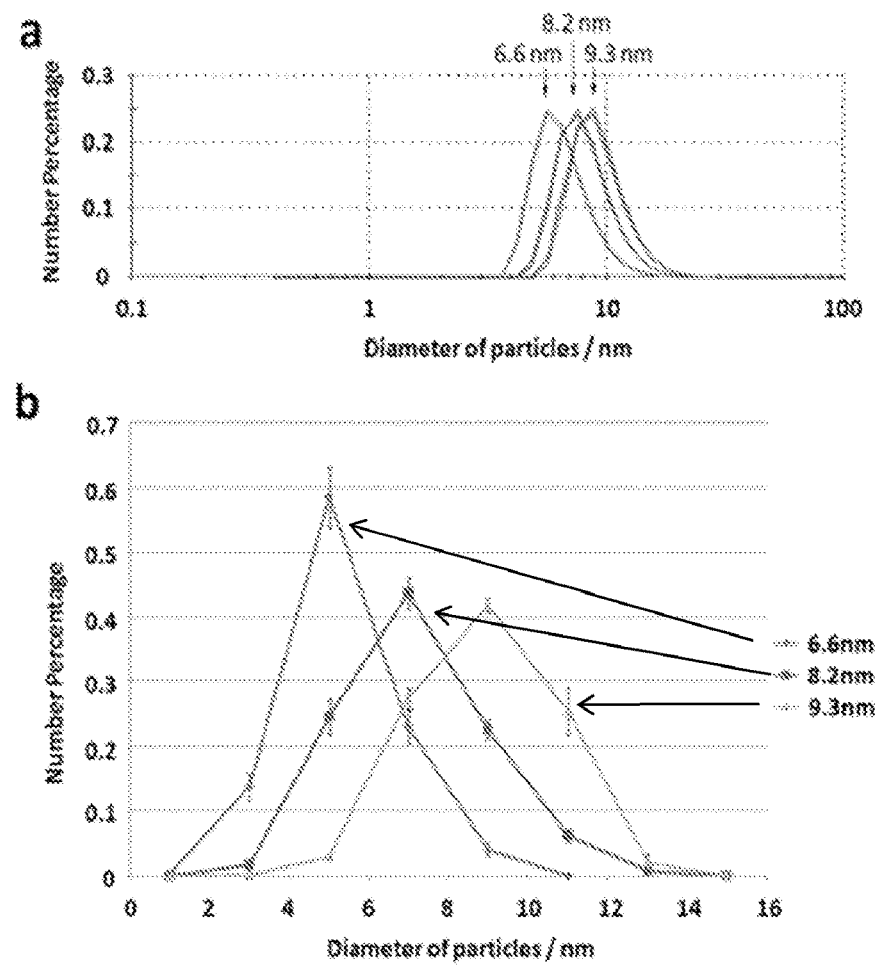
FIG. 2 shows representative size distribution of particles determined by (a) DLS and (b) TEM image analysis. In DLS each data set was measured three times per batch.

In order to demonstrate the kind of particle size and size distribution control achievable by this approach FIG. 1a-c shows transmission electron microscopy (TEM) results on particles from three synthesis batches obtained from varying synthesis conditions (see Table 1) leading to increasing particle size in the direction from a-c. The smaller magnification images illustrate the high degree of homogeneity in particle size while the higher resolution images in the insets reveal details of particle structure. In all cases TEM results suggest that silica has grown around an individual pore formed by CTAB template. An illustration of this type of structure, including the PEG chains on the outside of the particles, is depicted in FIG. 1d. While in FIG. 1a single pore particle formation is largely incomplete, FIG. 1b already displays side-on as well as head-on particles. Particles in FIG. 1c exhibit the most well-defined structure. FIG. 2a shows results of three independent size measurements for each of the three particle batches by dynamic light scattering (DLS). The data sets are very consistent and provide average hydrodynamic diameters of 6.6 nm, 8.2 nm and 9.3 nm for particles in FIG. 1a-c, respectively. Alternatively, particle size and size distribution were determined by quantitative TEM image analysis. TEM average diameters from data in FIG. 2b are 5.7 nm, 7.3 nm, and 8.9 nm, i.e. slightly smaller than from DLS. Both DLS and TEM results reveal fairly narrow size distributions and absence of any significant aggregation behavior. Smaller average diameters from TEM are expected, as this technique, in contrast to DLS, is insensitive to the PEG layer and water molecules dragged with it. As a result in the following DLS diameters as descriptors of the different particles were used.

Figure 3:
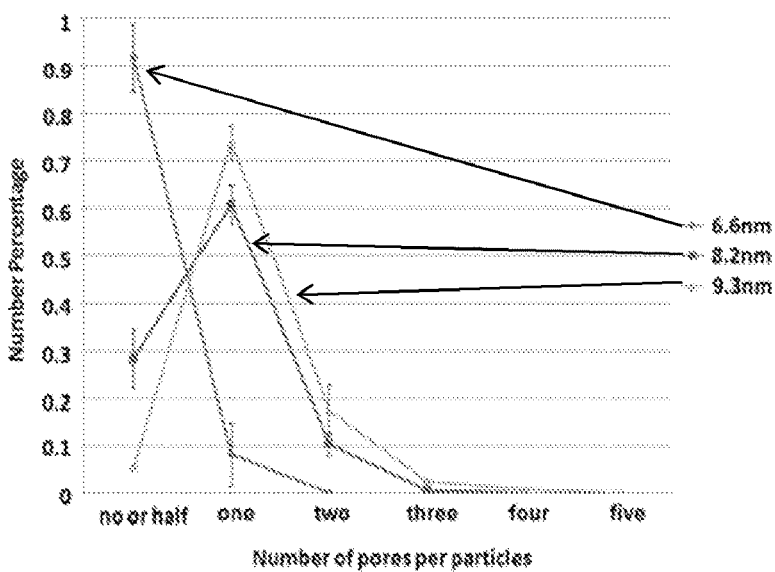
FIG. 3 shows representative distribution of number of pores per particle as determined from TEM image analysis; each data point is obtained by averaging three independent analyses.

TEM images also allowed analyzing the distribution of the number of pores per particle. As shown in FIG. 3, for around 90% of the 6.6 nm particles single-pore particle formation is incomplete (referred to as "no or half" pore particles in FIG. 3). As the diameter increases to 8.2 nm, the percentage of incomplete single-pore particles significantly drops from around 90% to below 30%. Increasing the diameter to 9.3 nm finally results in a fairly narrow distribution of the number of pores per particle in which more than 70% are single-pore particles. This distribution already is quite symmetric. Further increasing particle size most likely would bias the distribution towards an increase in the number of particles with more than one pore. The optimized hydrodynamic particle diameter for achieving single-pore particles in the synthesis should be close to the 9.3 nm value of the third synthesis batch.

Figure 4:
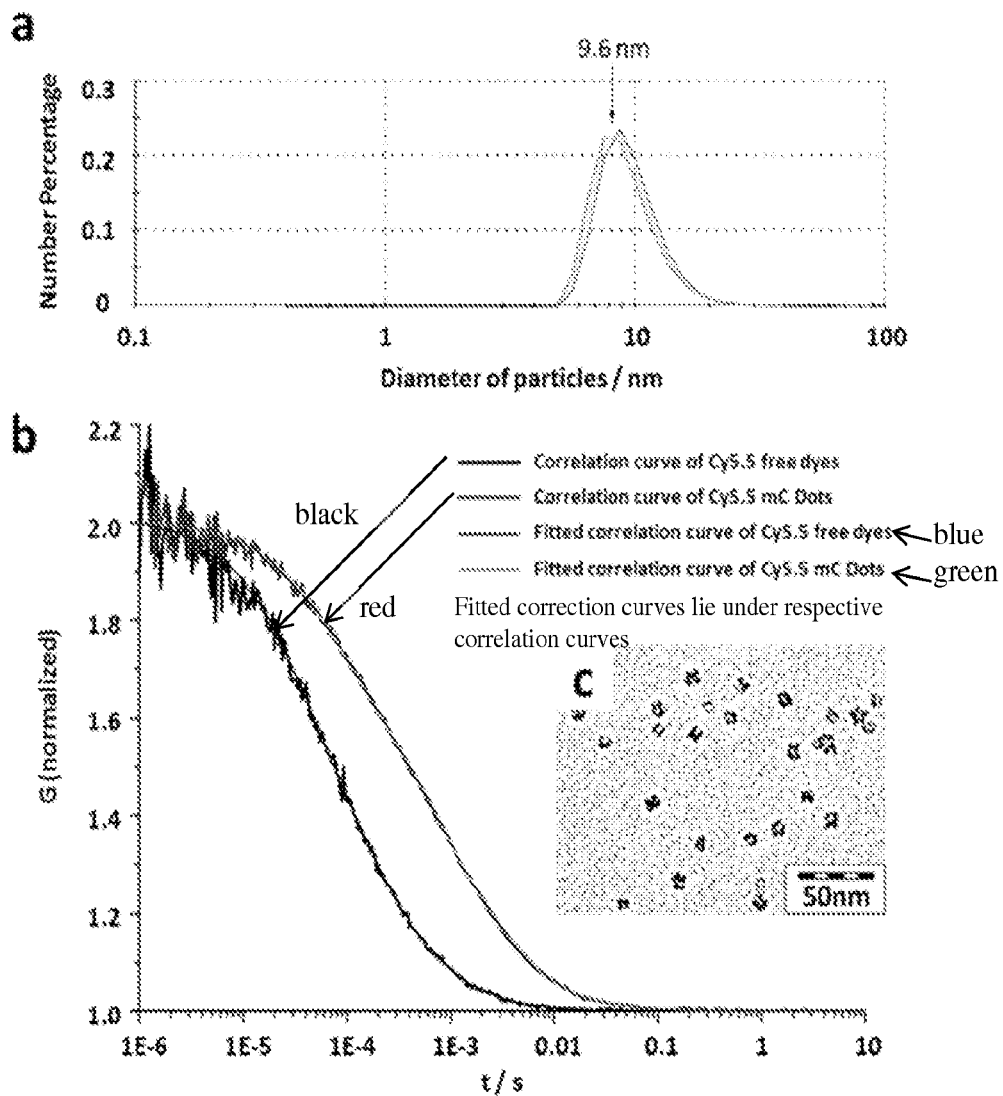
FIG. 4 shows representative characterization of Cy5.5 labeled mC dots. (a) DLS size measurements. (b) Normalized FCS curves for Cy5.5 free dye (black and blue lines) and Cy5.5 containing mC dots (red and green lines). (c) TEM image of the Cy5.5 mC dots.
Figure 7:
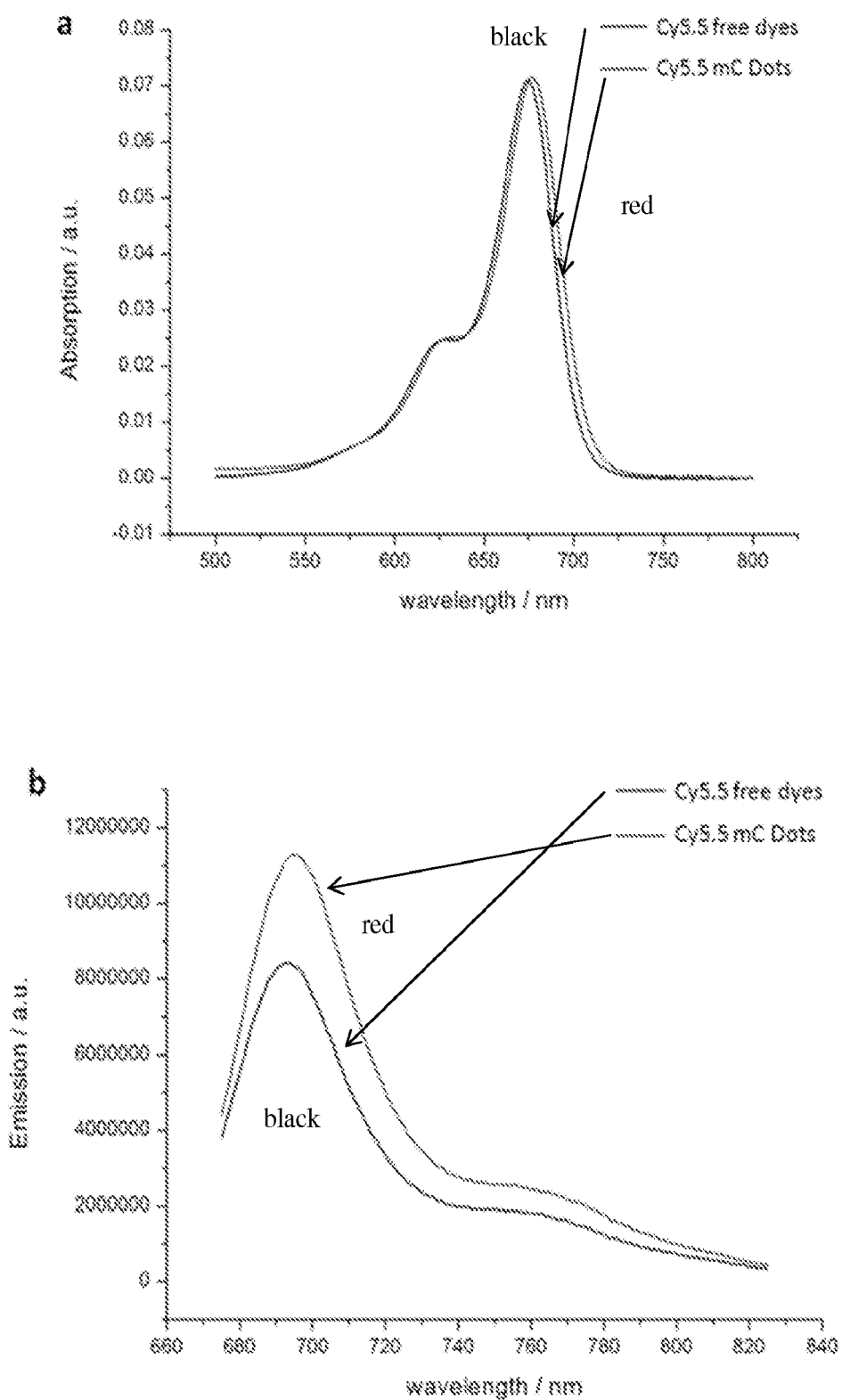
FIG. 7 shows representative absorption (a) and emission (b) spectra of Cy5.5 free dye (black line) and Cy5.5 labeled mC dots (red line).
Figure 8:
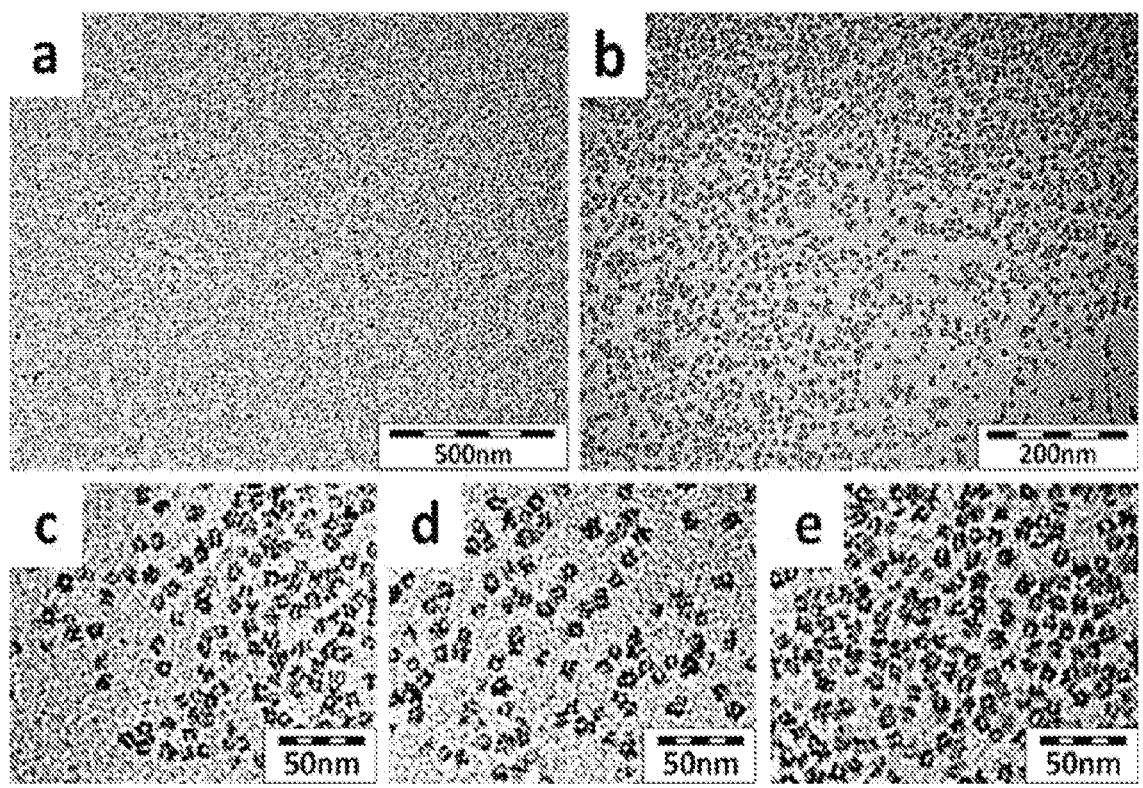
FIG. 8 shows representative TEM images of 9.3 nm particles at different magnification.

In order to visualize such <10 nm sized single-pore silica nanoparticles, in particular in biological environments, labeling with near infrared (NIR) dyes is highly desirable. In one embodiment, the synthesis protocol was slightly modified for the 9.3 nm particles by simultaneously adding silane conjugated Cy5.5 and TMOS into the reaction mixture. These dye-labeled mesoporous silica nanoparticles were referred to as mC dots. Cy5.5 has absorption and emission maxima around 675 nm and 700 nm, respectively, thus limiting interference from background fluorescence in biological tissue. Adding Cy5.5-silane conjugate to the reaction left the particle architecture largely unchanged. The DLS derived average hydrodynamic diameter of this sample increased to 9.6 nm as compared to 9.3 nm for the unlabeled particle (FIG. 4a). Furthermore, most of the particles still showed single-pore architecture (FIG. 4c). In order to verify that these particles carry a fluorescent label, fluorescent correlation spectroscopy (FCS) was used for further particle characterization (FIG. 4b). This technique is similar to DLS but uses the fluorescence of the diffusing moiety rather than the scattered light to generate auto-correlation data. FIG. 4b compares FCS results from free Cy5.5 dye and Cy5.5 labeled single-pore silica nanoparticles. As expected for the slower diffusing particle its curve is shifted to longer times. From the correlation time hydrodynamic diffusion coefficients can be derived. They are 1.5 nm and 10.2 nm for free dye and particle, respectively. FCS may thus slightly bias the true particle distribution to larger sizes. It should be noted, however, that the differences are rather small (10.2 nm from FCS vs. 9.6 nm from DLS). From the amplitude G(0) of the FCS autocorrelation one can derive the dye/particle concentration in solution while the optical detector count rate per diffusing species provides a direct measure of its brightness. Furthermore, in combination with static optical and fluorescence spectroscopy, FCS helps to provide information about number of dyes per particle, per dye enhancement over free dye in aqueous solution, as well as particle brightness. From analysis of spectrophotometer and spectrofluorometer data in combination with FCS concentration information on the free dye and particles, there are around 2.6 Cy5.5 dyes in one particle and the quantum enhancement of the Cy5.5 dye in the particles versus in aqueous solution is around 1.3 (FIG. 7). Thus a Cy5.5 doped mC dot is around 3.4 times brighter than a free Cy5.5 dye. This is consistent with direct brightness comparisons from FCS optical detector count rates (Table 3). It is further consistent with results of equivalent measurements on Cy5 containing ~7 nm C dots.

It is interesting to note that the single-pore silica nanoparticles described here have an "inside" and an "outside" that can be distinguished when additional conjugation chemistry is desired, e.g. to bind targeting or pharmaceutical moieties. During the PEGylation process the particle pores are occupied by structure directing CTAB molecules. Therefore, in contrast to the outer silica surface, it is expected that the PEG-silane coating has a significantly diminished probability of attaching to the (inside) surface of the pores. After CTAB extraction the unoccupied inside of the pore walls thus can be used for additional silane chemistry to conjugate specific moieties, which could be complementary to what is used on the outside of the PEGchains. Being in a similar size regime it is this ability to distinguish between the inside and the outside, and the larger overall surface area available for conjugation chemistry, which distinguishes these single-pore silica nanoparticles (or mC dots) from conventional C dots. This feature is an advantage in areas like sensing, drug delivery and theranostics.

Materials. All chemicals were used as received. Hexadecyltrimethylammonium bromide (CTAB), dimethyl sulfoxide (DMSO), (3-mercaptopropyl)trimethoxysilane (MPTMS), tetramethyl orthosilicate (TMOS) and 2.0 M ammonium hydroxide in ethanol were purchased from Sigma Aldrich. Methoxy-terminated poly(ethylene glycol) chains (PEG-silane, molecular weight around 500) was purchased from Gelest. Acetic acid was purchased from Mallinckrod. Cy5.5 florescent dye was purchased from GE. Absolute anhydrous 99.5% ethanol was purchased from Pharmco-Aaper. De-ionized (D.I.) water was generated using a Millipore Milli-Q system.

Synthesis of sub-10 nm ultra-small mesoporous silica nanoparticles. For the synthesis of 9.3 nm mesoporous silica nanoparticles, 0.23 mmol of CTAB and 2 ml of 0.02M ammonium hydroxide aqueous solution were added into 8 ml of D.I. water. Then the solution was stirred at 30° C. for 30 mins until CTAB fully dissolved. After that, 0.43 mmol of TMOS was added into the solution under vigorous stirring and the solution was further stirred at 30° C. for 24 hs. Following that, 0.21 mmol of PEG-silane was added and the solution was stirred at 30° C. for another 24 hs. In the next step, the temperature was increased from 30° C. to 80° C. and then stirred at 80° C. for another 24 hs. Afterwards, the solution was cooled to room temperature and then transferred into a dialysis membrane tube (Pierce, Molecular Weight Cut off 10000). The solution in the dialysis tube was dialyzed in 100 ml acid solution (which was a mixture of D.I. water, ethanol and acetic acid with the volume ratio 1:1:0.007) for 24 hs to extract CTAB out of the pores of the particles. This process was repeated three times. The solution was then dialyzed in 2000 ml DI-water for another 24 hs. This process was again repeated for three times. The particles were finally filtered through a 200 nm syringe filter (fisher brand) and then stored. The molar ratio of the reaction was 1 TMOS:0.53 CTAB:0.093 ammonium hydroxide:0.49 PEG-silane:1292 $H_2O$.

Particles with smaller sizes were synthesized using the same protocol but with lower concentrations of CTAB and TMOS as shown in Table 1.

TABLE 1

Synthesis condition of particles with different size

| | Concentration of CTAB | concentration of TMOS |
|---|---|---|
| 6.6 nm | 0.006M | 0.011M |
| 8.2 nm | 0.012M | 0.022M |
| 9.3 nm | 0.023M | 0.043M |

As the concentration of TMOS decreases, the condensation rate of the hydrolyzed silanes decreases. Thus the growth of the particles is slower and the particles become smaller in case all other conditions stay fixed.

Synthesis of Cy5.5 labeled single-pore silica nanoparticles. Cy5.5 dye with malemido functionality was conjugated to MPTMS in DMSO. The Cy5.5-silane conjugate was added together with TMOS into the synthesis solution to co-condense into the particles. The molar ratio of Cy5.5-silane conjugate to TMOS is 1:4855. The remainder of the synthesis protocol was kept the same as for the synthesis of the 9.3 nm particles.

Characterization of particle morphology and size. Transmission electron microscopy (TEM) images were taken using a FEI Tecnai T12 Spirit microscope operated at an acceleration voltage of 120 kV. Hydrodynamic particle sizes and size distributions were measured by dynamic light scattering (DLS) using a Malvern Zetasizer Nano-SZ at 20° C. Each DLS sample was measured three times and results were overlaid, see FIGS. 2a and 4a.

Figure 5:
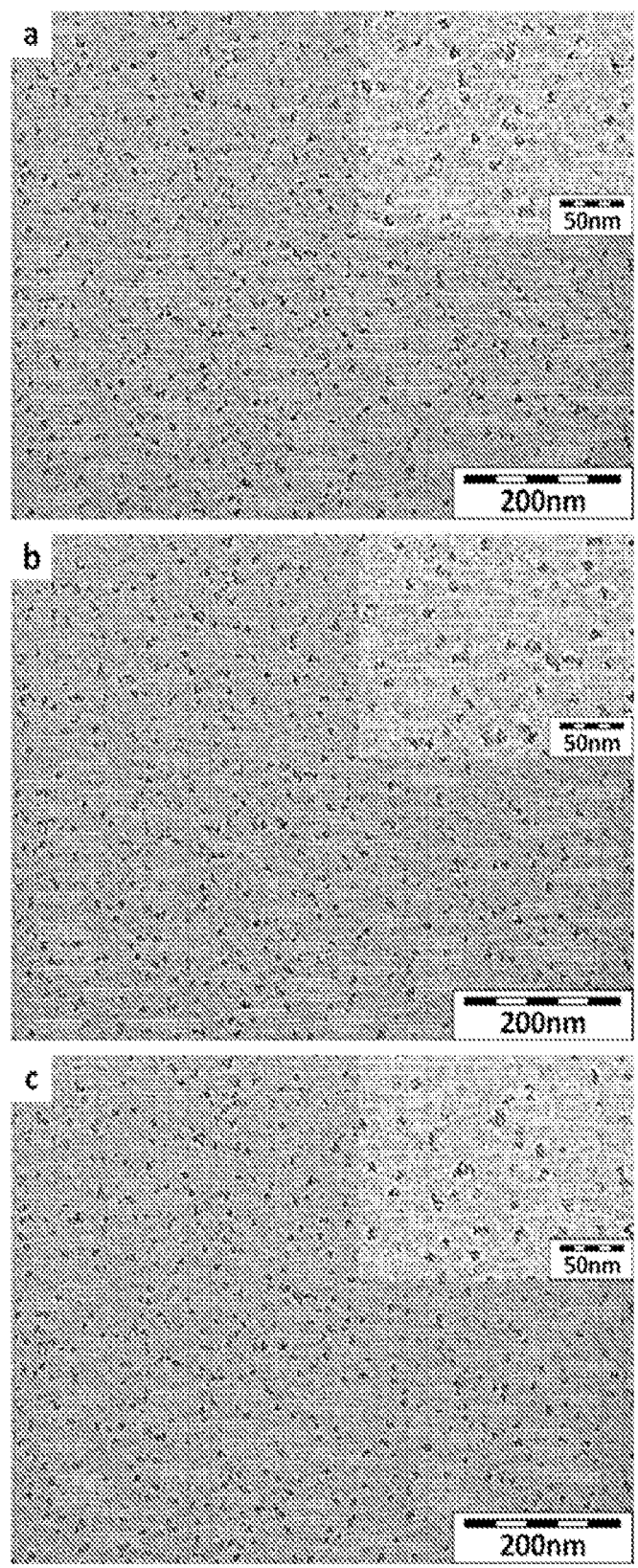
FIG. 5 shows representative TEM images of 8.2 nm sample used to analyze the size distribution of particles. (a), (b), (c) depict three separate size determinations using the same TEM image. Inserts display images of the same images but at higher magnification.
Figure 6:
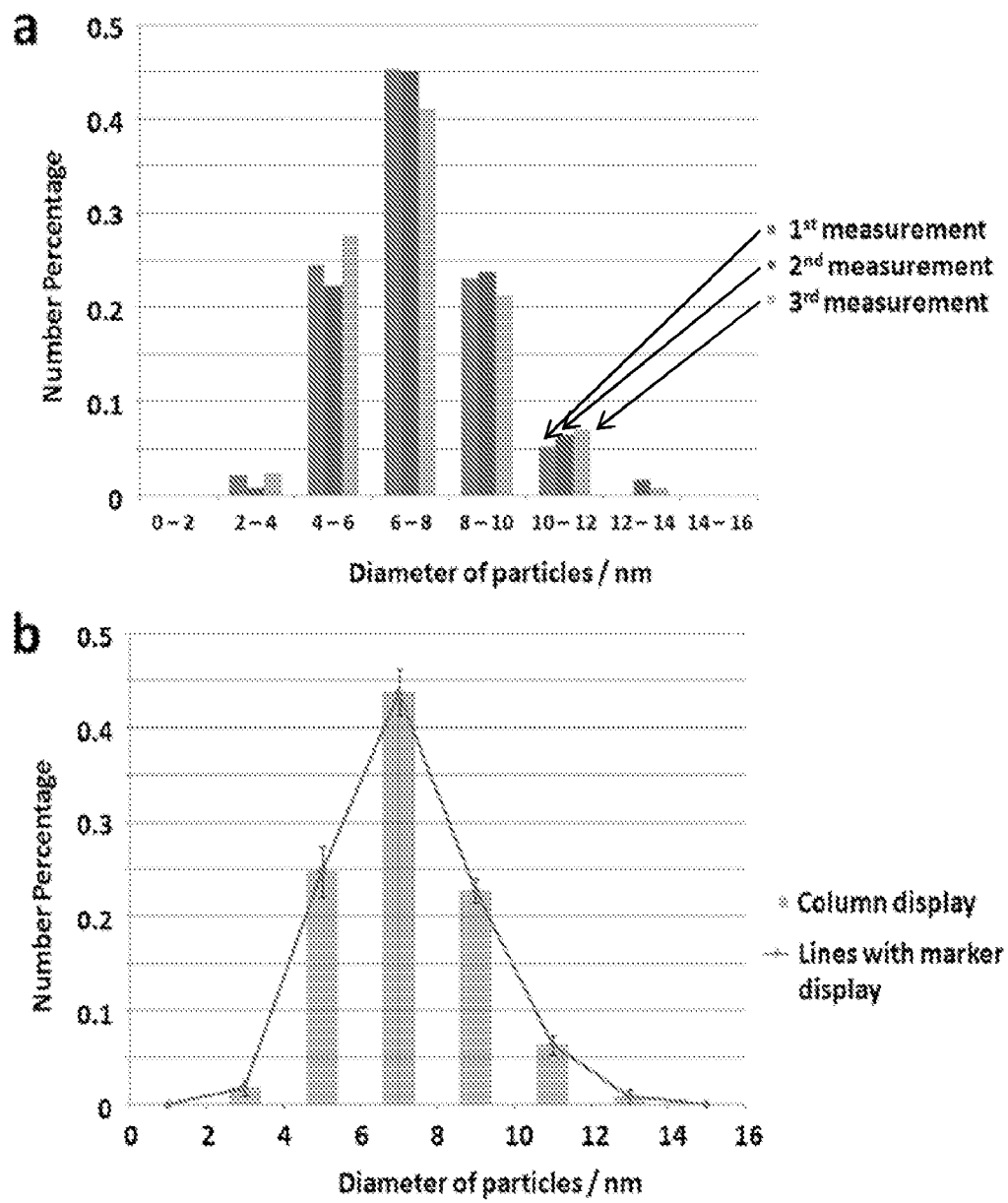
FIG. 6 shows representative diameter distribution of 8.2 nm sample measured by TEM. (a) Results of three individual measurements using the same TEM image. (b) Final averaged distribution with standard errors displayed for comparison by both columns and lines with markers.

Particle size distribution from TEM image analysis. In order to obtain size distribution data from TEM images, the diameters of over 100 particles were measured in the same image using a ruler tool provided by the TEM facility software. (FIG. 5a depicts this analysis for an image of the 8.2 nm particles). The software automatically recorded the diameters of all of the measured particles. Sorting the recorded diameters into bins generated the distribution of the particle size. Considering that the systematic error of the ruler tool can be as high as over 1 nm, due to the limited resolution of the TEM, the increment of the bins was set to 2 nm in order to optimize the analysis. Furthermore, in order to lower the standard error of each data point, this process was repeated three times for each sample (FIG. 5, FIG. 6a). The distribution results were then averaged and the standard errors were calculated (FIG. 6b). In order to compare the distributions of different samples in one diagram, lines with markers instead of columns were used to display the data (FIG. 6b). The average diameters measured by DLS and TEM are compared in Table 2.

TABLE 2

Comparison of the diameters measured by DLS and TEM

| sample | DLS diameters | TEM diameters |
|---|---|---|
| 6.6 nm | 6.6 nm | 5.7 nm |
| 8.2 nm | 8.2 nm | 7.3 nm |
| 9.3 nm | 9.3 nm | 8.9 nm |

TEM characterization of the distribution of the number of pores per particle. The distribution of the number of pores per particle of each sample was obtained through analyzing over 500 particles on a single TEM image with appropriate magnification. This process was repeated three times for each sample. The distribution results were then averaged and the standard errors were calculated. In order to compare the distributions of different samples in one diagram, lines with markers instead of columns were used to display the data.

Characterization of the fluorescent properties of Cy5.5 doped mC dots. Absorption-matched samples were prepared by appropriate dilution of Cy5.5 particles or Cy5.5 free dye with water and measured in quartz cuvettes using a Varian Cary 5000 spectrophotometer (Varian, Palo Alto, Calif.) (FIG. 7a). The extinction coefficient of Cy5.5 (250,000 M−1cm−1) was used to calculate the concentration of the dyes in the samples.

Fluorescence measurements of absorption-matched samples were performed on a Photon Technologies International Quantamaster spectrofluorometer (PTI, Birmingham, N.J.) in order to estimate the quantum efficiency enhancement per dye of the Cy5.5 dyes in the particles (FIG. 7b).

The absorption-matched samples were further measured on a home-built FCS using HeNe 633 nm excitation to characterize florescent properties, such as brightness per particle, hydrodynamic diameter and concentration of particles. The FCS instrument was calibrated for size prior to all measurements. The number of dyes per particle was derived from the ratio between the concentration of dyes measured by absorption spectra and the concentration of particles measured by FCS of the same sample. Results are shown in Table 3.

The slightly elevated number of dyes (# dyes) per diffusing species from FCS measurements of free Cy5.5 dye may be due to a small degree of aggregation of hydrophobic dye Cy5.5 in water. It should be noted, however, that it is within the error bar of the measurement.

TABLE 3

FCS characterization results for free Cy5.5 dye and Cy5.5 doped mC dots. Both, average value and standard deviation, are displayed.

| | Hydrodynamic diameter | #dyes/particle | Brightness/particle |
|---|---|---|---|
| Cy5.5 free dyes | 1.5 nm ± 0.2 | 1.07 ± 0.11 | 1452 kHz ± 21 kHz |
| Cy5.5 mC dots | 10.2 nm ± 0.4 | 2.60 ± 0.02 | 5322 kHz ± 29 kHz |

Liquid $^1H$ NMR analysis. All liquid $^1H$ NMR spectra were measured on a Varian Mercury 300 spectrometer. Two samples of the 9.3 nm particles were used in liquid $^1H$ NMR analysis. The first sample was dialyzed into water immediately after synthesis without acid extraction. The second sample was washed following the regular washing steps described in the synthesis protocol (first washed in acid to extract CTAB and later in water). Afterwards, the samples were dried under vacuum and then added into dimethyl sulfoxide-$d^6$ (DMSO-$d^6$, 99.96% d, Sigma-Aldrich) at an approximate concentration of 5 wt %. The fully washed sample initially showed some degree of sedimentation; however the sediments slowly redispersed after several hours of storage. Spectra were taken immediately after addition and after 2 days for comparison. Results showed no significant differences except for signal intensity. Control samples, i.e. CTAB and free PEG-silane, were dissolved in DMSO-$d^6$ and were measured immediately after dissolution.

Figure 19:
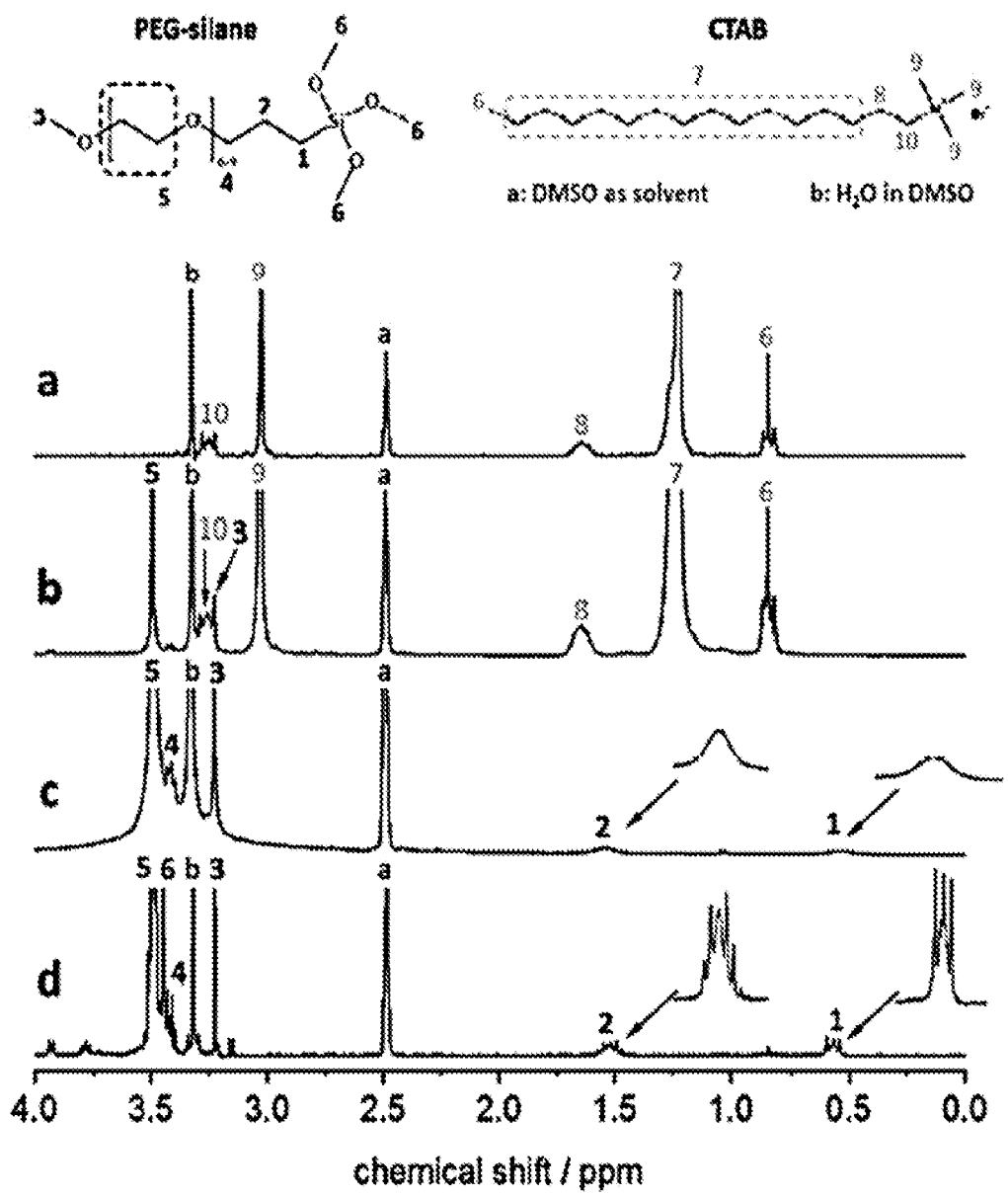
FIG. 19 shows a representative liquid $^1$H NMR spectra of (a) CTAB, (b) 9.3 nm particles washed with water without acid extraction, (c) 9.3 nm particles first washed with acid to extract CTAB and then washed with water, (d) free parent PEG-silane.

The $^1$H NMR spectra of the non-acid-extracted sample showed distinct peaks at chemical shifts corresponding to CTAB (0.8 ppm, 1.3 ppm and 3.0 ppm, compare spectra of CTAB and particles in FIGS. 19a and b), as well as peaks corresponding to PEG chains (3.5 ppm, compare spectra of particles and parent PEG-silane in FIGS. 19b and d). In comparison, there was no detectable signal from CTAB in the spectra of the fully-washed, CTAB extracted sample (FIG. 19c). This demonstrates the successful removal of CTAB via acid extraction.

Successful PEGylation can be inferred from broad signals of protons of PEG chains in the fully-washed sample (FIG. 19c), especially the peaks at 0.5 ppm and 1.5 ppm, which correspond to the α- and β-protons next to the silicon center of the PEG-chain. The line width broadening relative to the spectrum of the parent PEG-silane (FIG. 19d) indicates limited mobility of these protons, which is attributed to the formation of covalent bonds between PEG chains and the silica particle surface.

Figure 20:
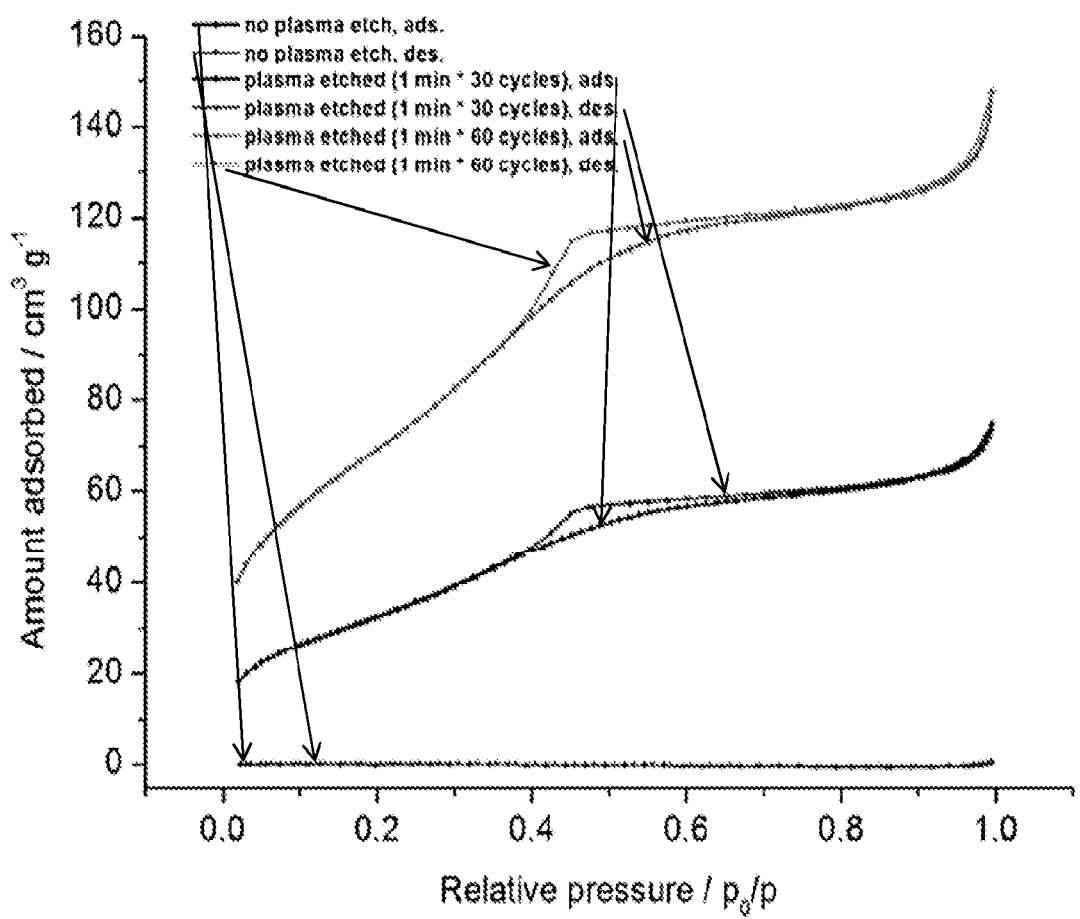
FIG. 20 shows representative $N_2$ sorption isotherms of 9.3 nm particles with different durations of plasma treatment.

Nitrogen sorption/desorption analysis. Nitrogen sorption/desorption measurements were performed on a Micromeritics ASAP 2020 instrument at 77K. Before the measurements, 9.3 nm fully-washed particles were first dried under vacuum and then subjected to a plasma etch treatment for different durations of time. Multiple cycles of plasma treatments were performed on a Harrick Plasma Cleaner with 1 min (or in one case 3 mins, see FIG. 21) cycle duration, to prevent sample heating. As demonstrated in FIG. 20, without plasma treatment the sample did not show any accessible surface area. This most likely is due to the PEG chains on the particle surface making accurate isotherm measurements difficult, consistent with earlier reports. As the duration of plasma treatment increased, more surface area became accessible.

Figure 21:
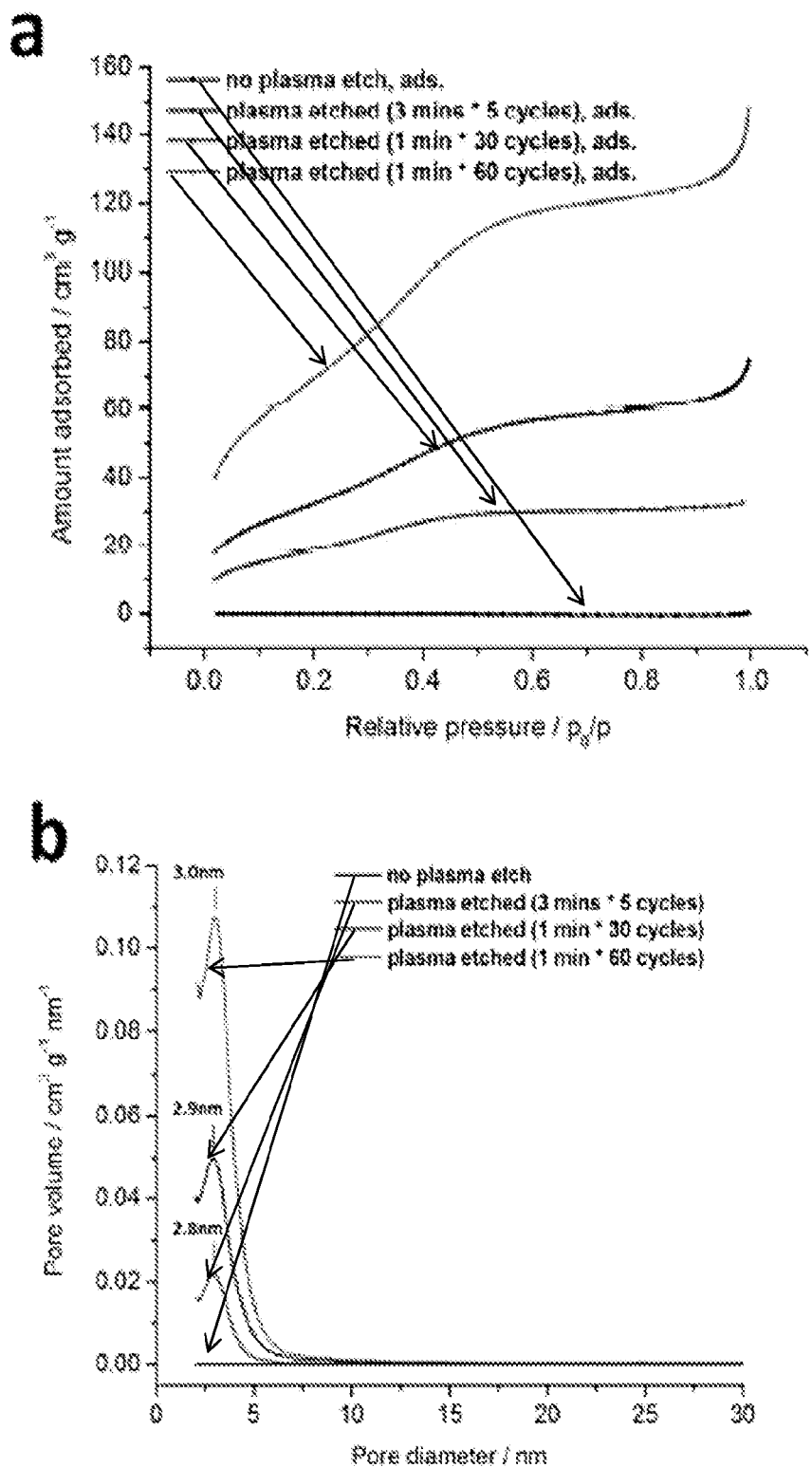
FIG. 21 shows representative comparison of pore size distribution, surface area and pore volume of 9.3 nm particles calculated from nitrogen adsorption data after different durations of plasma treatment (0, 15, 30, and 60 mins) (a) $N_2$ adsorption isotherms. (b) Pore size distributions obtained from $N_2$ adsorption isotherms employing the BJH method. Dependence of surface area (c) and pore volume (d) on duration of plasma treatment.
Figure 21:
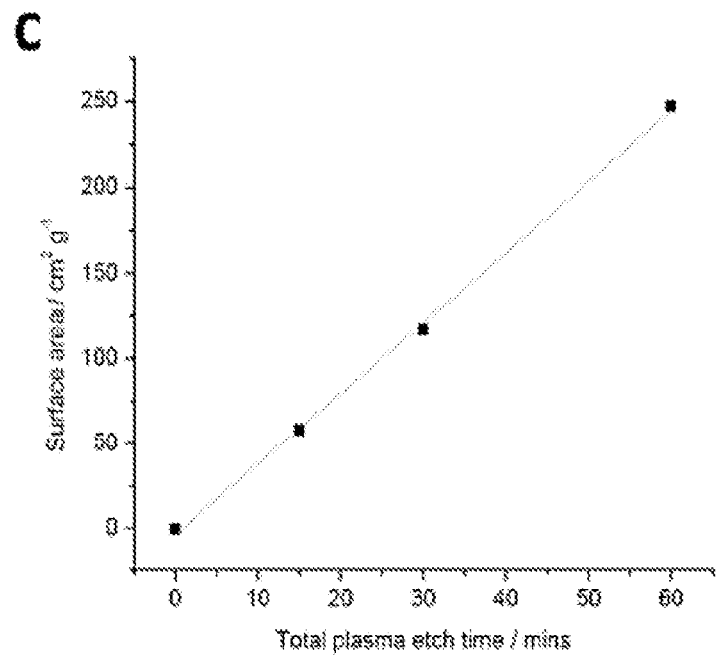
Figure 21:
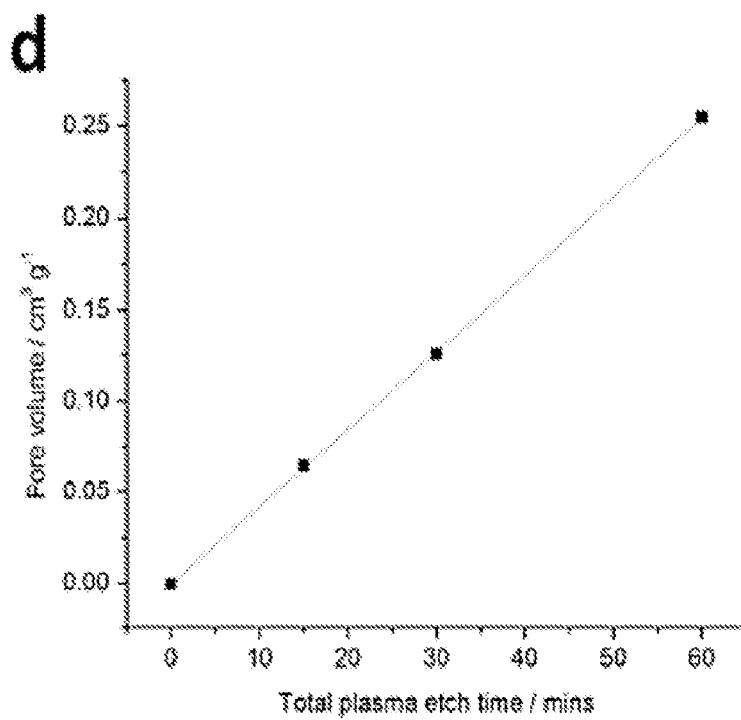

In order to corroborate the TEM images on pore structure and determine pore size distribution, the duration of plasma treatment was varied from 0 to 60 mins and the adsorption isotherms were used to calculate Barrett-Joyner-Halenda (BJH) pore size and pore size distribution, surface area and pore volume (FIG. 21). With increasing plasma treatment duration (15, 30, and 60 mins) surface area as well as pore volume increased. At the same time the average pore diameter increased from 2.8 nm (15 mins) to 2.9 nm (30 mins) to 3.0 nm (60 min) All of the plasma treated samples gave well defined pore sizes and pore size distributions, consistent with TEM analysis (FIG. 21b).

Example 2

This example describes a synthesis approach to sub-10 nm mesoporous silica nanoparticles with narrow size distributions and homogeneous porous particle morphology. Key features enabling this structure control are (i) fast hydrolysis, (ii) slow condensation, and (iii) capping of particle growth by addition of a PEG-silane at different time-points of the synthesis. Variation of synthesis conditions including monomer/catalyst concentrations, temperature, and time-point of PEG-silane addition leads to synthesis condition—particle structure correlations as mapped out by a combination of results from data analysis of dynamic light scattering (DLS) and transmission electron microscopy (TEM) measurements. Results establish precise control over average particle diameter from 6 to 15 nm with increments below 1 nm. In addition to MSNs, porous (single pore) fluorescent silica nanoparticles (mC dots) encapsulating blue (DEAC) and green (TMR) dyes were synthesized and characterized by a combination of DLS, TEM, static optical spectroscopy and fluorescent correlation spectroscopy (FCS) establishing dots for multi-color fluorescence applications. The ultra-precise particle size control demonstrated here in particular for sizes around and below 10 nm make useful for sensing, drug delivery and theranostic applications.

Figure 9:
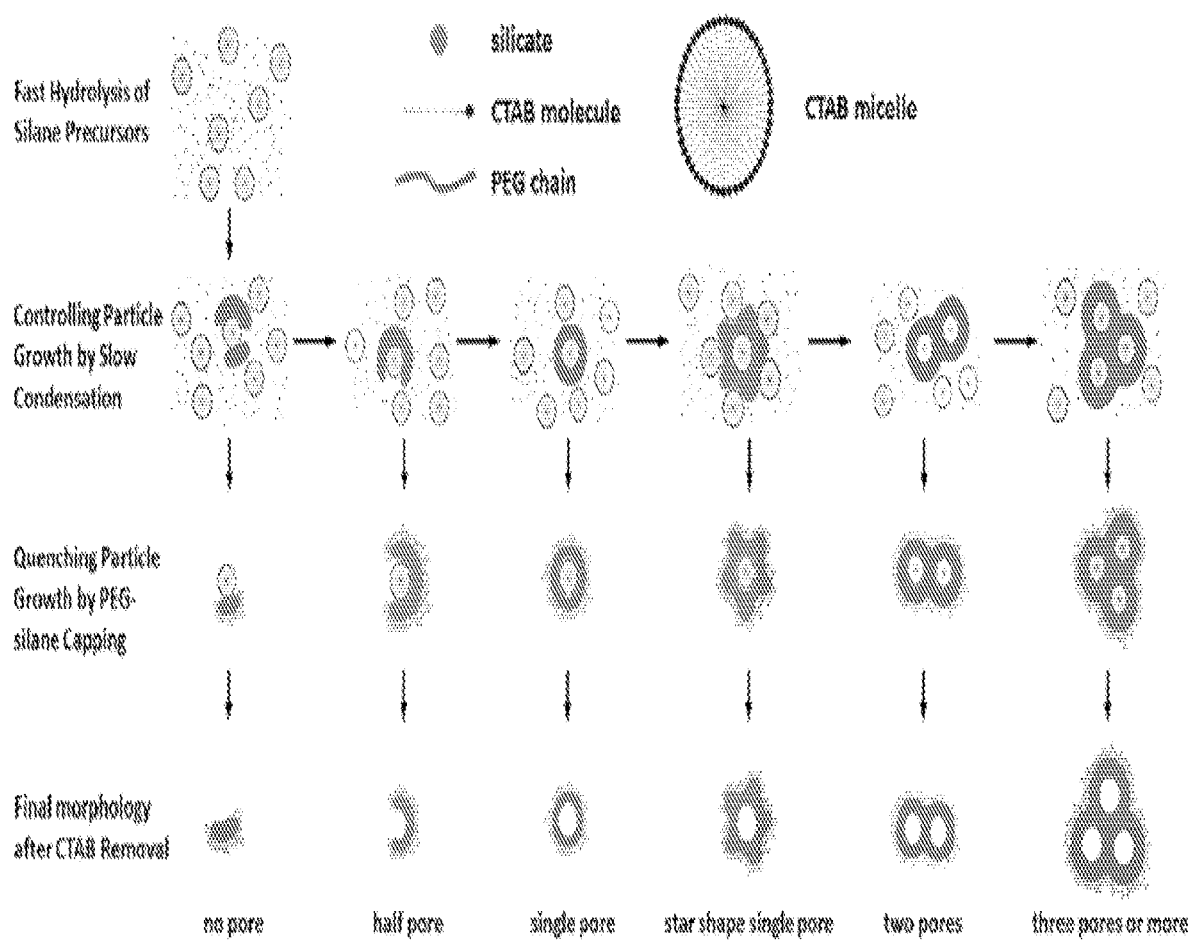
FIG. 9 shows an example of the synthesis procedure of ultra-small mesoporous silica nanoparticles with different particle size and morphology.

As shown in FIG. 9, there are three key steps which may help the synthesis of ultra-small mesoporous silica nanoparticles with narrow particle size distributions. The first one is fast hydrolysis. To that end TMOS was selected as silica source in the experiments since TMOS has the fastest hydrolysis rate among tetraalkoxysilanes and is highly soluble in water. The second one is a relatively slow condensation rate. Different types of base catalysts, L-lysine and ammonium hydroxide were tested as catalyst in the synthesis. Furthermore, pH, concentration of TMOS and reaction temperature were varied to further control the condensation rate. The third one is the use of an efficient capping agent to terminate particle growth. Here a PEG-silane was used as the termination agent. As the results demonstrate, by employing these elements, ultra-small sub-10 nm single-pore silica nanoparticles with narrow size distributions and high stability became accessible.

The condensation rate and quenching particles' growth at appropriate times via addition of PEG-silane allowed precise control of the average diameter of mesoporous silica nanoparticles from around 6 nm to larger than 15 nm with increments less than 1 nm. It is observed that the porous morphology of MSNs evolves as the average particle diameter increases. This structural evolution ultimately may help to better understand the interaction between CTAB micelles and silica precursors, particularly at the very early state of particle formation. Finally, in addition to the near infrared (NIR) dye Cy5.5 already encapsulate, DEAC (blue) and TMR (green) fluorescent dyes were co-condensed with TMOS to synthesize ultra-small single-pore florescent silica nanoparticles (mC dots) with different colors. Through the PEGylation step as part of the one-pot synthesis, the particles are already sterically stabilized after preparation for working in biological environments. Particles were characterized by a combination of transmission electron microscopy, dynamic light scattering, fluorescence correlation spectroscopy and optical spectroscopy.

Experimental Section. Chemicals and reagents. All chemicals were used as received. Hexadecyltrimethylammonium bromide (CTAB), dimethyl sulfoxide (DMSO), (3-aminopropyl)triethoxysilane (APTES), (3-mercaptopropyl)trimethoxysilane (MPTMS), tetramethyl orthosilicate (TMOS), L-lysine and 2.0 M ammonium hydroxide in ethanol were purchased from Sigma Aldrich. Methoxysilane-terminated poly(ethylene glycol) chains (PEG-silane, molecular weight around 500 g/mole) was purchased from Gelest. Acetic acid was purchased from Mallinckrod. DEAC florescent dye with thiol functionality, as well as TMR and Cy5.5 dyes with malemido functionality were purchased from GE. Absolute anhydrous 99.5% ethanol was purchased from Pharmco-Aaper. De-ionized (D.I.) water was generated using a Millipore Milli-Q system.

Synthesis of ultra small mesoporous silica nanoparticles using L-lysine as catalyst. For the synthesis of 6.6 nm mesoporous silica nanoparticles, 0.23 mmol of CTAB and 0.62 mmol of L-lysine were added into 10 ml of D.I. water. Then the solution was stirred at 30° C. for 30 mins until CTAB fully dissolved. After that, 0.43 mmol of TMOS was added into the solution under vigorous stiffing and the solution was further stirred at 30° C. for one hour. Following that, 0.21 mmol of PEG-silane was added and the solution was stirred at 30° C. for another hour. In the next step, the temperature was increased from 30° C. to 80° C. and stirring continued at 80° C. for another 24 hs. Afterwards, the solution was cooled to room temperature and then transferred into a dialysis membrane tube (Pierce, Molecular Weight Cut off 10000). The solution in the dialysis tube was dialyzed in 100 ml acid solution (which was a mixture of D.I. water, ethanol and acetic acid with the volume ratio 1:1:0.007) for 24 hs to extract CTAB out of the pores of the particles. This process was repeated three times. The solution was then dialyzed in 2000 ml DI-water for another 24 hs. This process was again repeated for three times. The particles were finally filtered through a 200 nm syringe filter (fisher brand) and then stored at room temperature for further investigations.

Figure 12:
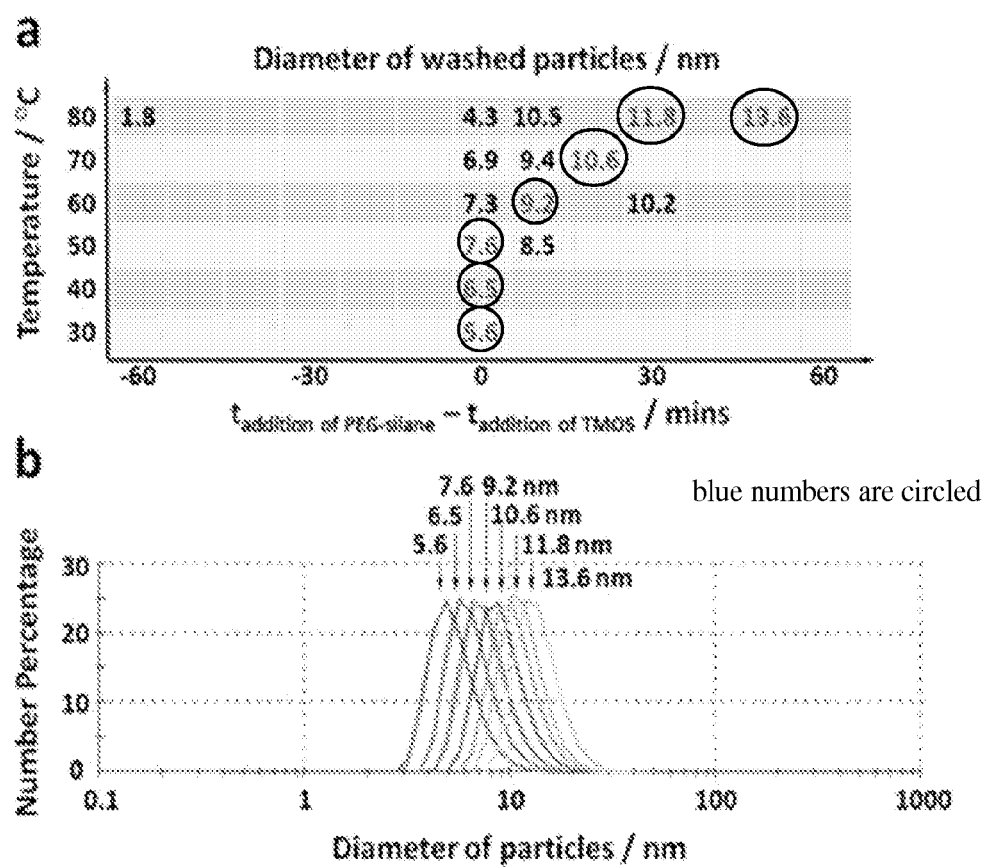
FIG. 12 shows (a) a map showing the average diameter of washed particles synthesized under different reaction conditions as measured by DLS. Each sample was measured three times and the results were averaged. (b) DLS measurement results on selected samples as indicated by blue numbers in (a).

The molar ratio of the reactants was 1 TMOS:0.53 CTAB: 2.7 L-lysine:0.49 PEG-silane:1292 $H_2O$. For the synthesis of particles with different average diameters, the initial synthesis temperature was varied from 30° C. to 80° C. and the time gap of the addition of PEG-silane after the addition of TMOS was varied from less than 1 minute to 1 hour, while other synthesis condition remained the same. Details of synthesis conditions are shown in FIG. 12.

Figure 14:
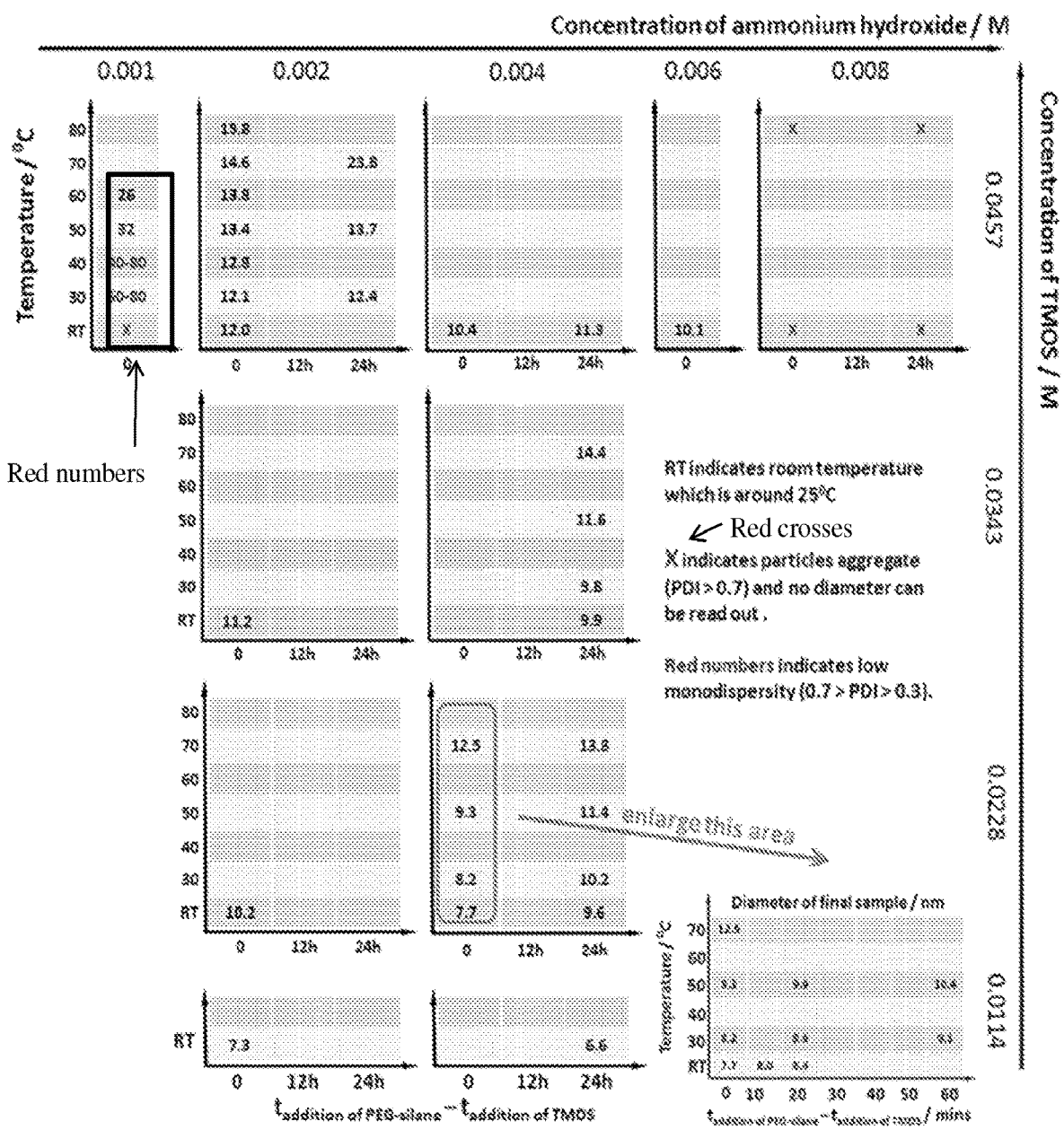
FIG. 14 shows a map showing the average diameters of washed particles synthesized under different reaction conditions with ammonium hydroxide as catalyst. The average diameter of each sample was measured by dynamic light scattering (DLS). Each sample was measured three times and results were then averaged.

Synthesis of ultra small mesoporous silica nanoparticles using ammonium hydroxide as catalyst. The synthesis procedure using ammonium hydroxide as catalyst was almost the same as the procedure using L-lysine as catalyst. The only difference was that instead of L-lysine a specific amount of ammonium hydroxide was added into the precursor solution as base catalyst. In order to control average particle diameters, initial synthesis temperature, concentration of TMOS and CTAB, concentration of ammonium hydroxide and time point of the addition of PEG-silane were varied independently. In more detail, the initial synthesis temperature was varied from 30° C. to 80° C. The concentration of ammonium hydroxide was varied from 0.001 M to 0.008 M. The concentration of TMOS was varied from 0.011 M to 0.046 M, while the molar ratio of TMOS to CTAB was fixed at 1:0.49. The time point of the addition of PEG-silane after the addition of TMOS was varied from less than 1 minute to 24 hours. Details of synthesis conditions are shown in FIG. 14.

Synthesis of ultra-small single-pore florescent silica nanoparticles (mC dots) with different colors. Cy5.5, TMR and DEAC were used as the florescent dyes to synthesize ultra-small single-pore florescent silica nanoparticles. Cy5.5 and TMR dyes with malemido functionality were conjugated to MPTMS in DMSO while DEAC dye with thiol functionality was conjugated to APTES in DMSO. The synthesis procedure of 9.3 nm sized particles using ammonium hydroxide as catalyst was used to prepare fluorescent mC dots. The respective silane-conjugated florescent dye with specific absorption and emission spectrum was added together with TMOS into the synthesis solution to condense into the final particle. The molar ratio of dye-silane conjugate to TMOS was 1:4855.

Characterization of particle morphology. Transmission electron microscopy (TEM) images were taken using a FEI Tecnai T12 Spirit microscope operated at an acceleration voltage of 120 kV. Hydrodynamic particle sizes and size distributions were measured by dynamic light scattering (DLS) using a Malvern Zetasizer Nano-SZ operated at 20° C. Each DLS sample was measured three times and results superimposed in the respective figures in this example. Number percentage curves are used to present the measurement results. The average diameter of each sample was calculated by averaging the mean diameters of number percentage curves from three measurements. Polydispersity index (PDI) with scale from 0 to 1 measured by DLS indicates the presence of a mixture of oligomers or aggregates in the sample. And the lower the PDI, the more monodisperse the sample is. PDI was used as the parameter to determine samples' polydispersity.

Analysis of particle size distribution. In order to obtain size distribution data from TEM images, the diameters of over 100 particles were measured in the same image using a ruler tool provided by the TEM facility software. The software automatically recorded the diameters of all of the measured particles. Sorting the recorded diameters into bins generated the distribution of the particle size. Considering that the systematic error of the ruler tool can be as high as over 1 nm, due to the limited resolution of the TEM images used, the increment of the bins was set to 2 nm in order to optimize the analysis. Furthermore, in order to lower the standard error of each data point, this process was repeated three times for each sample. The distribution results were then averaged and the standard errors were calculated. In order to compare the distributions of different samples in one diagram, lines with markers instead of columns were used to display the data.

Analysis of number of pores per particle distribution. The distribution of the number of pores per particle of each sample was obtained through analyzing over 500 particles on a single TEM image with appropriate magnification. This process was repeated three times for each sample. The distribution results were then averaged and the standard errors were calculated. In order to compare the distributions of different samples in one diagram, lines with markers instead of columns were used to display the data.

Characterization of fluorescent properties of dye encapsulating mC dots. Absorption-matched samples were prepared by appropriate dilution of dye doped particles and free dye with water and measured in quartz cuvettes using a Varian Cary 5000 spectrophotometer (Varian, Palo Alto, Calif.) (FIG. 7a). The extinction coefficients of DEAC (42000 M−1cm−1), TMR (98000 M−1cm−1) and Cy5.5 (250,000 M−1cm−1) were used to calculate the concentration of the dyes in the samples.

Fluorescence measurements of absorption-matched samples were performed on a Photon Technologies International Quantamaster spectrofluorometer (PTI, Birmingham, N.J.) in order to estimate the quantum efficiency enhancement per dye of the dyes encapsulated in the particles versus the free dye in aqueous solution.

The absorption-matched samples were further measured on a home-built FCS using solid state 445 nm (for DEAC particles), HeNe 535 nm (for TMR particles) and solid state 633 nm (for DEAC particles) excitation to characterize florescent properties, such as brightness per particle, hydrodynamic diameter and concentration of particles as described in reference. The FCS instrument was calibrated for size prior to all measurements. The number of dyes per particle was derived from the ratio between the concentration of dyes measured by absorption spectra and the concentration of particles measured by FCS of the same sample.

Results and discussion. Controlling particle growth through optimizing hydrolysis and condensation. As discussed in the introduction, it is desirable to have fast hydrolysis in order to synthesize ultra small silica nanoparticles with narrow size distributions. Fast hydrolysis here means that the time period needed for silane hydrolysis should be much shorter than the time period needed for silica condensation. In the best of all cases, the hydrolysis process can be completed before the majority of hydrolyzed silicic acid derivatives condenses. This can be facilitated through use of a rapidly hydrolyzing silica source and appropriately slowing down the silica condensation rate thereby adjusting particle growth to a convenient time window. This enabled observation of the process of mesoporous silica nanoparticle growth from sub-nanometers to tens of nanometers.

Here, TMOS was used as silica source since it has the fastest hydrolysis rate among tetraalkoxysilanes. Both hydrolysis rate and condensation rate in silica sol-gel chemistry greatly depend on pH. The hydrolysis product, silicic aid, lowers solution pH. In a base catalyzed sol-gel reaction this slows down hydrolysis but accelerates condensation, which for reasons outlined above is not favorable. In order to study the effects of hydrolysis rate and condensation rate on particle size, instead it would be desirable to fix the pH during the synthesis. For this reason L-lysine was initially selected as buffer catalyst, which can maintain the pH slightly above 9 at appropriate concentrations. Since the pKa's of $\alpha$-$(CH_2)_4NH_3^+$, $\alpha$-$NH_3^+$ and $\alpha$-COOH in L-lysine are estimated to be 10.28, 8.90 and 2.18, respectively, about 92% of $\alpha$-$(CH_2)_4NH_2$ and 33% of $\alpha$-$NH_2$ are protonated under the synthesis condition (pH around 9.2). Through the electrostatic interactions between these positively charged protonated amine groups on L-lysine and negatively charged deprotonated hydroxyl groups on the silica surface, L-lysine molecules tend to attach on the surface of silica particles and deactivate the hydroxyl groups. Consequently, this attachment hinders condensation occurring on silica surfaces and thus further lowers the growth of silica nanoparticles.

Figure 10:
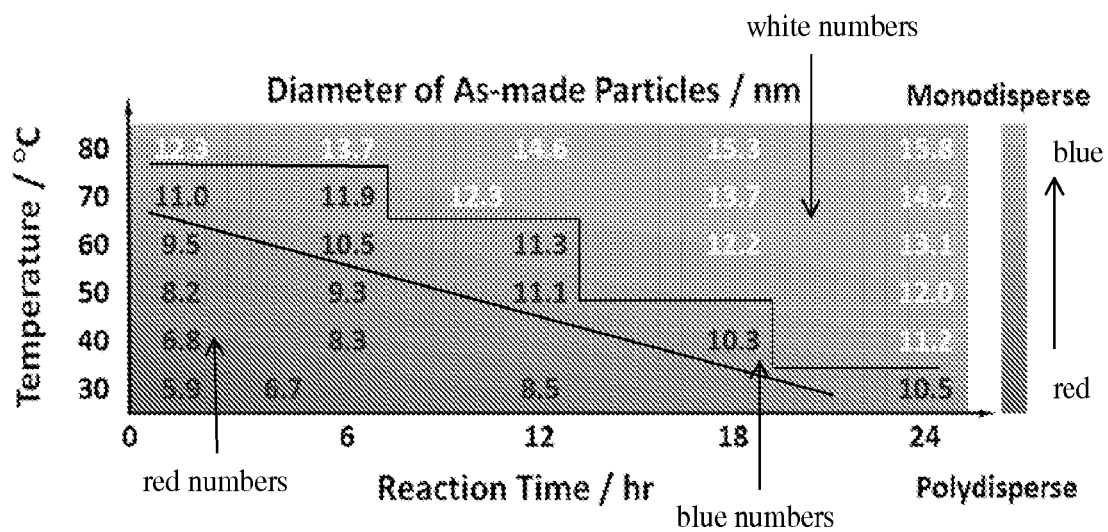
FIG. 10 shows a representative map showing the average diameters of as-made particles synthesized under different reaction conditions as measured by dynamic light scattering (DLS). Each sample was measured three times and the results were then averaged.

Based on these considerations, MSNs were synthesized using L-lysine as catalyst and TMOS as silica source. The initial pH of the reaction was 9.2 and was maintained around 9 through the whole reaction by L-lysine. The synthesis temperature was varied from 30° C. to 80° C. and the reaction time was varied from 1 hour to 24 hours to control the growth of the particles. The average diameters of the as-made particles under different synthesis conditions were measured by DLS using a very small amount of the reaction solution. Results are shown in FIG. 10. Each data point in FIG. 10 comes from a different synthesis batch. Each synthesis batch were repeated one or two times in this example and the results were very close with deviations in size of less than 0.5 nm. From FIG. 10, for a particular temperature particles grow bigger as reaction time increases. For example, at 80° C. particles grow from around 12 nm after 1 hour to 16 nm in 24 hours. The same trend was observed for all temperatures studied between 30° C. and 80° C. However, overall the particle size decreases as synthesis temperature is decreased. Please note that by shortening reaction time and lowering synthesis temperature, the average diameter of as-made particles can be pushed down to less than 6 nm. These results suggest that by using TMOS as silica source and L-lysine as buffer catalyst, which can lower the condensation rate through surface association, particle growth can be slowed down to a convenient time window allowing size control in a range from about 5 to 15 nm.

However, it was found that the stability of the synthesized particles greatly depended on size. According to DLS measurements of samples after washing, particles with smaller average diameters showed higher polydispersity indexes (PDIs). Particularly for <10 nm particles, the PDIs were always higher than 0.7 and no distinct size distribution could be read out in light scattering measurements. This suggests that these particles greatly aggregated during the washing step. Only the particles with average diameters larger than 12 nm maintained narrow size distributions in treatment steps after synthesis. According to the final value of the PDI, different colors were assigned to the data in FIG. 10. White numbers indicate that the final PDIs of the samples were lower than 0.25, which is an acceptable value. Red numbers indicate that the final PDIs were higher than 0.7, which suggests severe aggregation of final particles after washing. Blue numbers signify PDIs between 0.7 and 0.25. Based on these data FIG. 10 shows a graded background color depicting the relationship between the average diameter of as-made particles and their size dispersity after the washing step. Using L-lysine as catalyst, the smaller particles always have lower stability and higher size dispersity. As the average diameters drop to below 10 nm, the stability of particles against aggregation becomes low. This may be due to the higher surface energy of smaller particles. Another reason may be the presence of residual free silicic acid in solution when the reaction was stopped. This silicic acid may lead to uncontrolled condensation during the washing step and thus cause aggregation. In summary, although the average diameters of as-made particles can be varied from about 5 nm to about 16 nm, additional steps can taken in order to improve particle stability.

Quenching particle growth through addition of PEG-silane. A PEGylation step is typically conducted before in-vivo experiments not only for stabilizing particles, but also for lowering particle surface charge and obtaining better biodistribution characteristics. Inspired by the comparison of colloidal particle growth with living (anionic) polymerization for the generation of narrowly distributed objects and the use of termination/capping agents in living polymerizations, it was contemplated that a PEGylation step could actually be used during the one-pot synthesis to terminate particle growth thereby providing an additional control parameter for particle size. Integrating the PEGylation step into the one-pot synthesis would simultaneously prevent particle aggregation by sterical stabilization and enabling work in high salt containing biological environments without additional synthesis steps.

Figure 11:
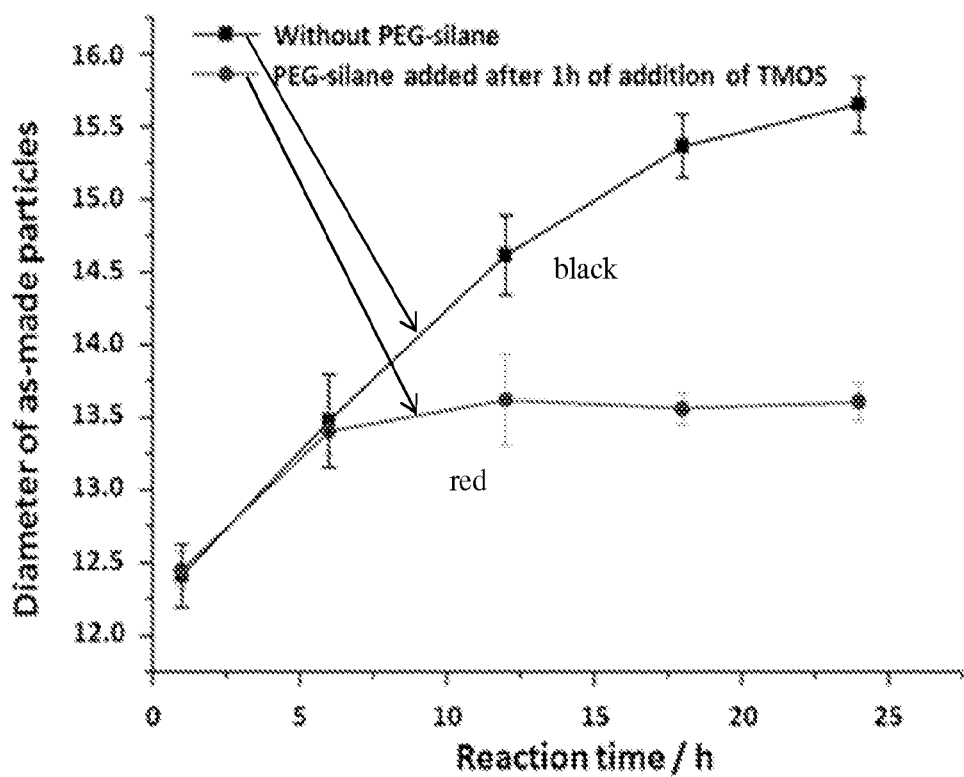
FIG. 11 shows representative particle diameters as measured by dynamic light scattering (DLS) during particle growth in the absence (squares) and presence (circles) of PEG-silane. Each data point was obtained by averaging three independent measurements.

In order to proof the principle of using PEG-silane as a particle capping agent which terminates growth, the growth process of two syntheses were compared, one with PEG-silane and one without PEG-silane. The average particle diameter with DLS was measured, sacrificing a very small amount of the reaction solution at different reaction times (1, 6, 12, 18 and 24 hours). For the synthesis with PEG-silane the average particle diameter was first measured after 1 hour reaction to make sure the particle size is comparable with that of the synthesis without PEG-silane (FIG. 11). At the same time of the measurement, 100 micro liter of PEG-silane was added into the synthesis mixture. From FIG. 11, without PEG-silane the MSNs grew from around 12 nm at 1 hour to around 15 nm after one day.

In contrast, if PEG-silane was added one hour after the addition of TMOS, the average diameter of the resulting particles grew a bit further to around 13.5 nm and then stayed roughly constant throughout the remainder of the synthesis process. This result suggests that addition of PEG-silane during the reaction indeed can efficiently quench particle growth. Actually, during more detailed studies, it was observed that the average diameter of particles always increased by several Angstroms once PEG-silane was added. This increment occurred within seconds. Data further suggest that PEG-silane molecules first only physically attach to the particles through, e.g. Van der Waal's interactions or electrostatic interactions, instead of covalently bonding to the particle surface. It is this relatively fast attachment that enables PEG-silane to efficiently quench particle growth.

In order to fully condense the PEG-silanes to the silica nanoparticles, a subsequent heat treatment for 24 hrs at 80° C. was applied as the final step of the synthesis. No significant size change was observed as a result of this heat treatment. Considering that there still is unreacted silane in the reaction mixture during heat treatment and that high temperatures increase the condensation rate and speed up particle growth (FIG. 10), this further corroborates that the growth of the particles is effectively quenched by PEG-silane.

Quenching particle growth via PEG-ylation adds a powerful tool to control particle size. Based on results reported in FIG. 10, in subsequent experiments PEG-silane was added as a capping agent into batches under different synthesis conditions. In more detail, the particle synthesis temperature was varied from 30° C. to 80° C. to control the growth rate. The time gap between the additions of TMOS and PEG-silane was varied from less than 1 minute to 50 minutes to quench particle growth at different time points. FIG. 12a maps out the relationship between final average particle diameter as measured by DLS and synthesis conditions. While the x-axis of FIG. 10 is overall reaction time, the x-axis of FIG. 12a is a relative time axis between the addition of TMOS and PEG-silane. In all cases reported in this Figure, 24 hours after addition of PEG-silane a 80° C. heat treatment for another 24 hours was applied to covalently fix the PEG-silane onto the particle surface. All of the batches showed distinct DLS size curves (FIG. 12b) with average sizes from 5.6-13.6 nm separated by 1-1.5 nm, as well as relatively low PDIs, indicating no noticeable aggregation after washing. These results further demonstrate the high efficiency of termination via PEG-silane.

Figure 13:
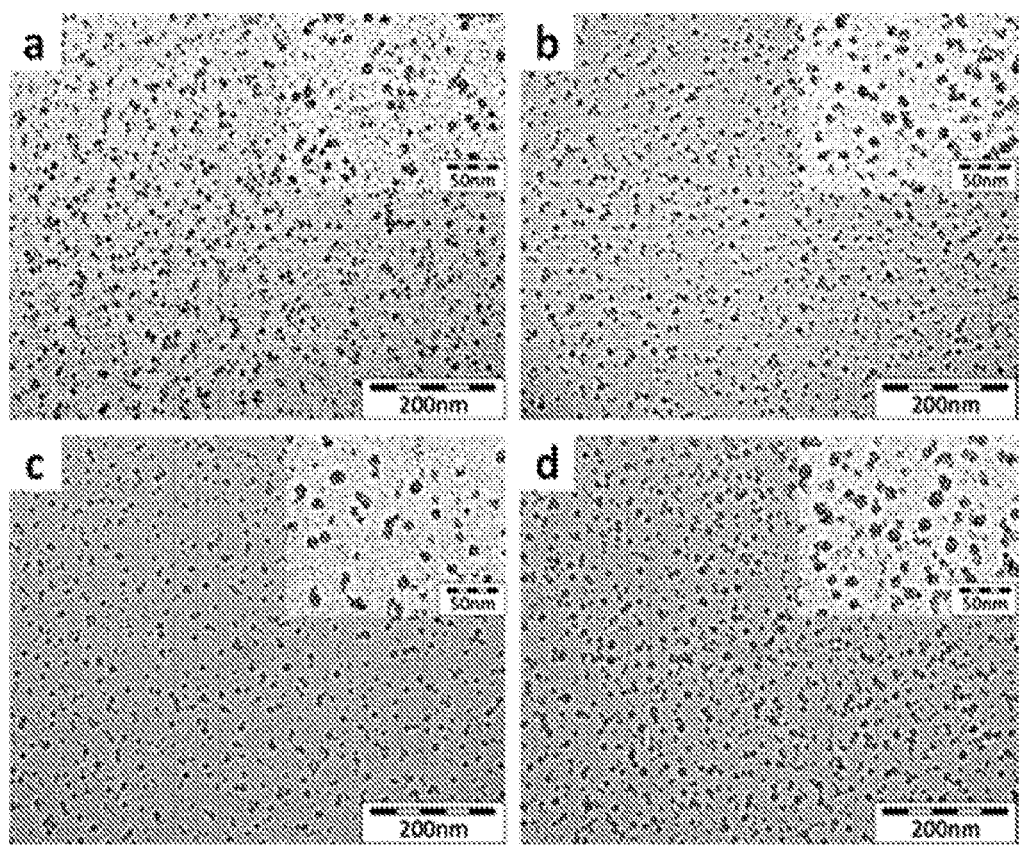
FIG. 13 shows representative TEM images of silica particles with different average diameters: (a) 5.6 nm, (b) 7.6 nm, (c) 10.6 nm and (d) 13.6 nm. Inserts display images of the same samples but at higher magnification.

From FIG. 12a, at 80° C., if PEG-silane is added right on top of the addition of TMOS (x axis equals to 0), the final average particle diameter is below 5 nm. When PEG-silane is added 50 minutes after the addition of TMOS, the final average particle diameter increases to above 13 nm. The same trend is observed as the synthesis temperature is decreased. This finding is consistent with a longer growth period leading to larger and larger particles if PEG-silane is added at later and later time points. Interestingly, from FIG. 12a by fixing the PEG-silane addition right on top of the TMOS addition, the final average particle diameter first increases but then decreases as temperature increases from 30° C. to 80° C. This is very different to the behavior displayed in FIG. 10 where the as-made particle size continued to increase with temperature, most likely due to an increase of the condensation rate. The difference may be ascribed to the largely different mobility of PEG-silane at different temperatures. As PEG-silane is a relatively big molecule compared to free silicic acid, its mobility is expected to be more temperature dependent and might greatly increase at the higher synthesis temperatures. Consequently, while at lower temperatures the increasing condensation rate of the silicic acid first leads to larger particles with increasing temperature, at even higher temperatures the PEG-silane mobility increases to a point where the capping reaction becomes the dominant step thus reducing particle size. From FIG. 12a, when TMOS and PEG-silane are added on top of each other, the temperature threshold where the reactivity of PEG-silane and silicic acid reverses is between 50° C. and 60° C. FIG. 13a-d shows TEM images of selected particles with increasing hydrodynamic diameters, of 5.6 nm, 7.6 nm, 10.6 nm and 13.6 nm, respectively (as measured by DLS, see FIG. 12b). The smaller magnification images illustrate the high degree of particle size uniformity while the higher resolution images (FIG. 13, insets) reveal details of particle structure. In FIG. 13a some of the particles show single-pore structure with diameter close to 10 nm while some of them are no pore containing silica pieces of just 2 or 3 nm. Although the average diameter of this sample from DLS is 5.6 nm, the TEM image suggests some size distribution. As the average diameter increases to 13.6 nm (FIGS. 13b to 13e), larger particles with more pores begin to show up while the percentage of smaller particles decreases. As a result, the average particle diameter increases consistent with the DLS measurements (FIG. 12b). Both DLS measurements and TEM images indicate reasonably high particle uniformity without any detectable aggregation. However, a finite size distribution within the different particle batches is clearly visible in TEM.

This finite particle size distribution might be due to the use of L-lysine as catalyst. As L-lysine molecules can attach to the surface of the growing silica particles, both the isotropic silica growth and the structure directing effect of CTAB might be disturbed resulting in particle structure inhomogeneities.

Next, other catalysts to generate ultra-small (<10 nm) MSNs with precise control over size distribution and morphology were studied.

Synthesis using ammonium hydroxide as catalyst. Several types of base catalysts have been successfully used in the synthesis of mesoporous silica nanoparticles, such as triethanolamine (TEA), tetramethylammonium hydroxide and ammonium hydroxide. In this example, ammonium hydroxide as catalyst replacing L-lysine was attempted. Ammonium hydroxide is a common chemical used in silica synthesis. Second, ammonium hydroxide is a relatively small molecule, which does not tend to attach to the silica surface. Finally, no negative effects of ammonium hydroxide e.g. on PEGylation were found.

Results on average particle diameter as measured by DLS from particle synthesis batches obtained under different experimental conditions are mapped out in FIG. 14. The map is constructed as a set of sub-maps each having the same style as the one displayed in FIG. 12a. The x axis of each sub-map indicates the time gap between the additions of TMOS and PEG-silane, while the y axis of each sub-map indicates the initial synthesis temperature. Different sub-maps along the overall x and y directions were obtained for different concentrations of ammonium hydroxide and TMOS, respectively. In this way FIG. 14 displays what is actually a four dimensional map in only two dimensions, as there are a total of four synthesis parameters that were varied: (1) concentration of ammonium hydroxide, (2) concentration of TMOS, (3) addition of PEG-silane relative to TMOS, and (4) initial temperature. Parameters (1), (2) and (4) were used for controlling particle growth rate while parameter (3) was used for controlling the growth period.

Considering the sub-map with the concentration of ammonium hydroxide of 0.002 M and the concentration of TMOS of 0.0457 M ($2^{nd}$ sub-map from top left in FIG. 14), where the PEG-silane is added on top of TMOS (i.e. x axis value=0): Here the average diameter of the final washed particles increases with increasing synthesis temperature from room temperature (RT) to 80° C. It is interesting to note that this monotonic trend is similar to the L-lysine system in the absence of PEG-silane capping (FIG. 10), but very different compared to behavior of the L-lysine system with capping, where the average diameter of washed particles first increased and then decreased with temperatures increasing from 30° C. to 80° C. (FIG. 12*a*, x axis equals to 0). This difference may be due to a difference in condensation rates in the L-lysine catalyzed system versus the ammonium hydroxide system. For ammonium hydroxide, an immediate drop of solution pH was observed from about 10 to close to 8 upon injection of TMOS into the reaction, probably due to the instantaneous hydrolysis of TMOS producing silicic acid. This observation is consistent with the expected behavior from calculation results. Since the $pK_b$ of ammonium hydroxide is estimated to be 4.75, the pH of 0.002 M ammonium hydroxide aqueous solution is 10.26. Since the $pKa_1$ and $pKa_2$ of orthosilicic acid are estimated to be 9.84 and 13.2, respectively, the pH of the solution drops from 10.26 to 8.42 after all of the 0.0457M TMOS hydrolyzes. For one thing, this almost immediate drop of pH further indicates the fast hydrolysis rate of TMOS, which is a prerequisite in the proposed mechanism (FIG. 9) to obtain narrow particle size distributions. Furthermore, since the silica condensation rate is maximized at a pH around 8.4, this reaction condition actually results in the maximum condensation rate. As a result, a relative high pH triggers the fast hydrolysis of TMOS upon which silicic acid is produced by hydrolysis of TMOS. In turn this lowers the pH thus optimizing the particle growth rate. In comparison, the synthesis pH of the L-lysine system always stays around 9 throughout the reaction. This pH in the L-lysine system reduces both, the initial hydrolysis and the condensation rates of TMOS relative to the ammonium hydroxide catalyzed system. Furthermore, as already discussed the attachment of L-lysine molecules on the silica particle surface can further slow down particle growth. For these reasons, the growth rate of particles is much faster in the ammonium hydroxide catalyzed system than in the L-lysine system. While the non-monotonic dependence of final particle size on synthesis temperature in the L-lysine system (FIG. 14, x axis equals to 0) indicated a competition between silicic acid condensation and PEG-silane quenching, in the ammonium hydroxide system this competition does not manifest itself in the particle size since the condensation rate of silicic acid is always fast enough to outcompete PEGylation leading to monotonically increasing particle size with temperature. This trend is observed in almost all of the sub-maps in FIG. 14. The same sub-map ([ammonium hydroxide]=0.002 M, [TMOS]=0.0457 M) also shows that the average diameter of washed particles always increases when PGE-silane addition is delayed, irrespective of temperature. In analogy to the L-lysine system, this is simply because a longer growth period results in bigger particles. This trend is also observed in all of the sub-maps in FIG. 14.

When concentrations of ammonium hydroxide of 0.008 M or higher, or lower than 0.001 M were used, particle size control was lost. As indicated by the red crosses in FIG. 14, when the concentration of ammonium hydroxide was 0.008 M or higher, silica always formed aggregates and precipitated either during the reaction or during the washing steps. Similarly, when the concentration of ammonium hydroxide was 0.001 M or lower, silica formed aggregates at room temperature and no distinct particle diameter could be read out in DLS measurements. As the synthesis temperature increased from room temperature to 80° C., average particle diameter gradually decreased from unreadable (aggregation) to around 26 nm. It is interesting to note that this monotonic decrease of particle size at higher temperatures is totally opposite to what is observed in other sup-maps with ammonium hydroxide concentrations equal to or higher than 0.002 M. This is because the hydrolysis rate of TMOS decreases at lower ammonium hydroxide concentration. When the concentration of ammonium hydroxide decreases below a threshold, the hydrolysis process is not fast enough to complete before particle formation. Consequently, instead of condensation, hydrolysis dominates the growth kinetics of particles by continuously providing silicic acid, which further condenses onto the particles. As a result, higher temperature predominantly increases the hydrolysis rate and results in higher particle concentration but smaller particle size. Actually, this is very similar to the synthesis of silica particles using TEOS as silica source where smaller particles are obtained at higher temperature. In both, the TEOS system and the near-neutral-pH TMOS system, hydrolysis has a lower kinetic rate than condensation and thus dominates the growth of the particles. This is very different compared to the proposed mechanism for optimal control of particle growth (FIG. 9) where condensation rather than hydrolysis is the dominating process for the particle growth. Only when hydrolysis is fast enough and condensation becomes the dominant growth process, is it possible to focus on the very early stage of particle formation and the synthesis of ultra-small mesoporous silica nanoparticles becomes possible. According to FIG. 14, the threshold of ammonium hydroxide concentration to trigger this mechanism in the system is between 0.001 M and 0.002 M. By comparing the sub-maps in FIG. 14 for different ammonium hydroxide concentrations from 0.002 M to 0.006 M, but with the same TMOS concentration of 0.0456M, it was observed that particle size decreases as the concentration of ammonium condensation pH of the synthesis with an ammonium hydroxide concentration of 0.002 M is around 8.42, which is slightly higher than 8.4, the pH of maximum condensation rate, higher ammonium hydroxide concentrations will result in higher pH and slower condensation rates, and consequently in smaller particle sizes.

Within the appropriate region of ammonium hydroxide concentration (0.002M to 0.006 M), TMOS concentration was further varied to control particle growth. TMOS/CTAB ratio was always fixed when the concentration of TMOS was varied. As shown in the sub-maps with the same ammonium hydroxide concentration of 0.002 M, but different TMOS concentration, the average diameter of washed particles decreased from 12.0 nm to 7.3 nm when the TMOS concentration decreased from 0.0457 M to 0.0114 M. The same decreasing trend was observed in batches with ammonium hydroxide concentration of 0.004 M. This suggests that as the concentration of TMOS decreases, the condensation rate of TMOS decreases resulting in slower particle growth.

In order to demonstrate the size control possible with the approach, the area in the green circle in FIG. 14 was enlarged. As shown by the inserted sub-map in FIG. 14, by fixing the ammonium hydroxide concentration at 0.004 M and the TMOS concentration at 0.0228 M, the average particle diameter can be precisely tuned from less than 8 nm to larger than 12 nm with increments of about 0.5 nm through simply varying synthesis temperature and when PEG-silane is added relative to TMOS in order to quench particle growth.

Figure 15:
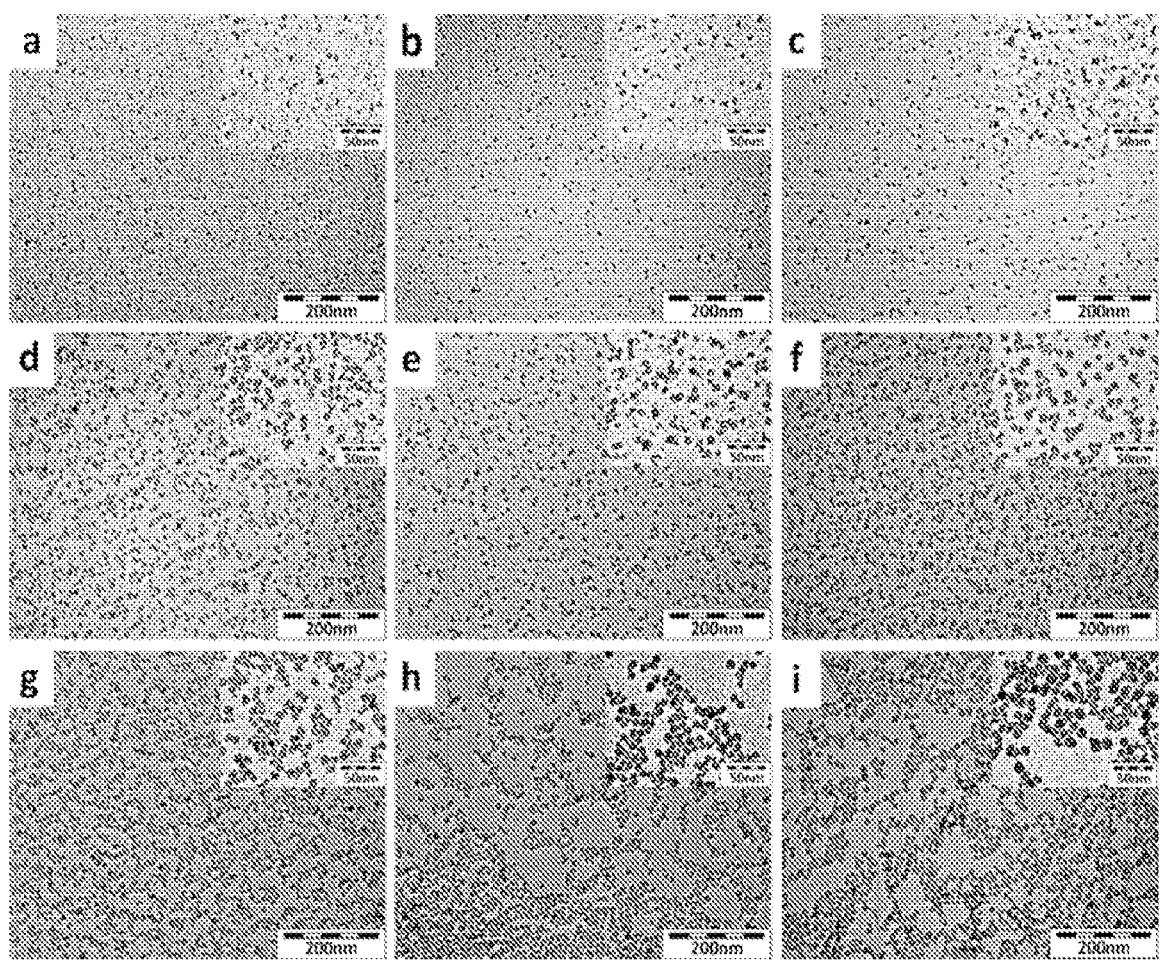
FIG. 15 shows representative TEM images of silica particles with different average diameters: (a) 6.6 nm, (b) 7.3 nm, (c) 8.2 nm, (d) 9.3 nm, (e) 10.2 nm, (f) 11.3 nm, (g) 12.1 nm, (h) 13.5 nm, and (i) 15.9 nm. Inserts display images of the same samples but at higher magnification.
Figure 16:
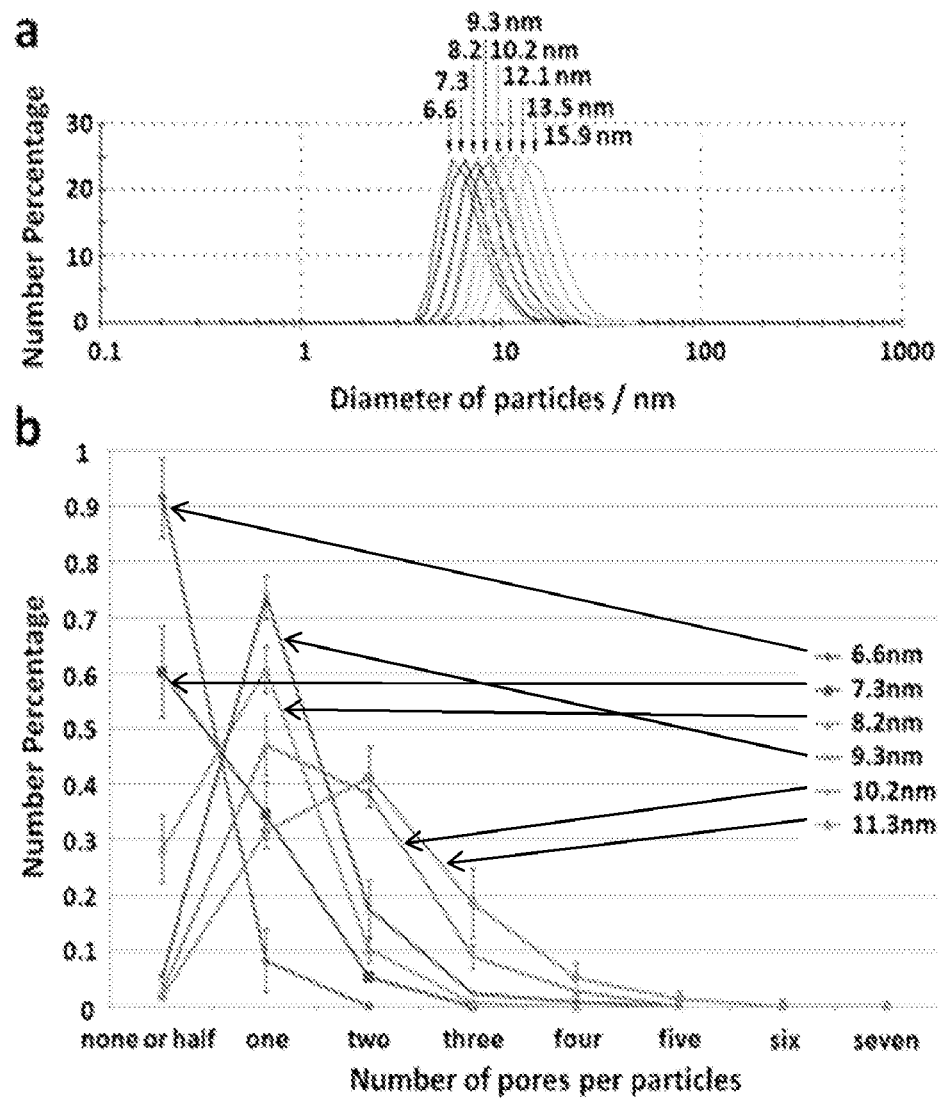
FIG. 16 shows representative (a) DLS measurement results of selected particles with different average diameters synthesized with ammonium hydroxide as catalyst. (b) Distributions of number of pores per particle determined from TEM image analysis.

Morphology characterization of ultra-small mesoporous silica nanoparticles. Nine samples with increasing average diameters out of the map shown in FIG. 14 were selected for morphology characterization. FIG. 15 shows the TEM images of the selected samples with diameters ranging from 6.6 nm to 15.9 nm. The smaller magnification images illustrate the high degree of homogeneity in particle size while the higher resolution images in the insets reveal details of particle structure. Compared to the mesoporous silica nanoparticles synthesized with L-lysine as catalyst (FIG. 13), the particles synthesized with ammonium hydroxide have a more homogeneous morphology and narrower size distribution. This is probably due to the fact that L-lysine molecules tend to attach on the surface of silica particles and thus affect particle morphology. Another reason might be that the condensation rate with ammonium hydroxide is higher and thus results in higher degree of particles formation. FIG. 16a summarizes DLS measurement results for these selected samples. Data for the 11.3 nm sample is not included in FIG. 16a because the x axis (particle diameter) is on a log-scale. The DLS curve of the 11.3 nm sample thus almost completely overlaps with the curve of the 10.2 nm sample. Both, the TEM images as well as the DLS measurement results suggest that particles of different batches are highly uniform in size without detectable aggregation.

The narrow size distribution of particles from different batches enables taking a look at the morphological evolution as a function of particle size. In order to quantitatively assess this evolution, the TEM images of samples in FIG. 15 were used to analyze the distribution of the number of pores per particle for each of the batches. Results of this analysis are shown in FIG. 16b. As the average diameter of the particles increases, the distribution of the number of pores per particle shifts to larger numbers and, more interestingly, becomes wider. Among the batches studied, the 9.3 nm sample has the most homogeneous pore morphology: More than 70 percent of the particles are single-pore particles. Non-pore or half-pore particles, i.e. pieces that stem from unfinished micelle encapsulation by the growing silica (see FIG. 9) can hardly be found.

In order to relate particle morphology to particle size, the distribution of particle diameter on the basis of the TEM data was further quantitatively analyzed. As shown by the diameter distributions in FIG. 17, all samples showed relatively narrow size distributions. However, as the average diameter increases, in analogy to the analysis in FIG. 16b of the number of pore distributions, the distributions of particle diameter shift to the right side and become wider. These two distributions are related. A series of TEM images of individual particles were inserted into the top of FIG. 17 in order to further elucidate this relation. This series nicely details the morphological evolution of individual particles with increasing diameter as depicted by the x-axis. As particles grow from around 3 nm to close to 20 nm, the number of pores per particle gradually increases from none to more than four. Through snapshots of particles from various batches this series of images graphically illustrates the growth process of an individual mesoporous silica nanoparticle with time, compare also with FIG. 9. Almost all of the single-pore particles have accessible pores, instead of the formation of hollow shells (FIG. 15 d to f). This might suggest that the association of CTAB micelles in the silica particle formation process is more dynamic rather than static.

Figure 17:
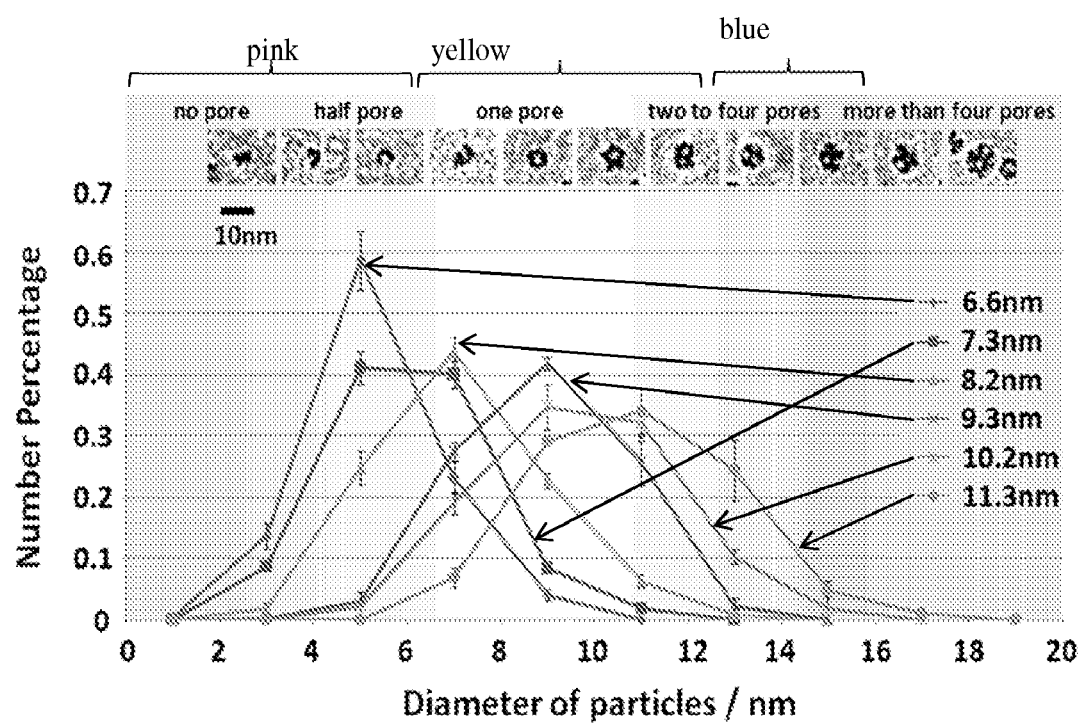
FIG. 17 shows representative particle size distributions as determined by TEM image analysis. Inserted TEM images (top) correlate particle morphology with size. Colors identify size ranges leading to the same particle morphology.

In order to further facilitate the direct comparison between the distributions of particle diameter with the distributions of the number of pores per particle, in FIG. 17 different colors were assigned to particle diameter ranges leading to the same number of pores per particle. For example, the pink area represents non-pore or half-pore particles while the yellow area represents single-pore particles. Colors change gradually as there is no distinct cut-off size between different morphologies. In FIG. 17, the yellow area is the biggest area beginning from around 6 nm and ending at around 11 nm. All particles with diameters within this area are single-pore particles. In comparison, the areas of two-pore to four-pore particles are smaller. This is reasonable in light of geometrical considerations. In order to maintain a relatively low overall surface energy, MSNs always tend to have sphere-like shape. For this reason, growing a new pore on a bigger particle with more pores will cause less increment of particle size.

From the color code in FIG. 17, it is straightforward to tell the morphology distribution of samples with different average diameters, consistent with the independent measurements shown in FIG. 16b. For example, the diameter distribution of the 6.6 nm sample occupies both the pink and yellow areas, which suggests there are non-pore particles, half-pore particles and also single-pore particles present in this sample. According to FIG. 17, the percentage of the non-pore and half-pore particles in this sample is roughly around 80%, which is close to the independent measurement result around 90% (FIG. 16b). The slight discrepancy is due to the fact that there is no distinct cut-off diameter between particles with different pore morphologies. Since FIG. 17 provides a semi-quantitative idea about the morphological homogeneity of a given size distribution, it is a very helpful diagram in guiding the synthesis of ultra-small mesoporous silica nanoparticles, e.g. for nanotheranostic applications. According to FIG. 17, among the particles with well-developed pores, the single-pore particles cover the widest diameter range from around 6 nm to around 11 nm (yellow area in FIG. 17). Firstly, this size range matches well with the targeted size window for rapid renal excretion and favorable biodistribution characteristics of nanoparticles. Secondly, considering the fact that the diameter distribution of synthesized samples is always several nanometers wide, this 6-11 nm size range is able to include almost the entire size distribution of an individual particle synthesis batch. It thus allows to achieve an optimum in homogeneity in pore morphology within a single synthesis.

One of the presented samples whose diameter distribution fits into this range is the 9.3 nm sample (FIG. 17). As shown in the corresponding TEM images (FIG. 15d), the synthesized particles are uniformly sized and homogeneous in morphology, i.e. almost all of the particles have a single well-defined pore. This is further elucidated for this batch by the number of pores per particle distribution analysis shown in FIG. 16b.

Figure 18:
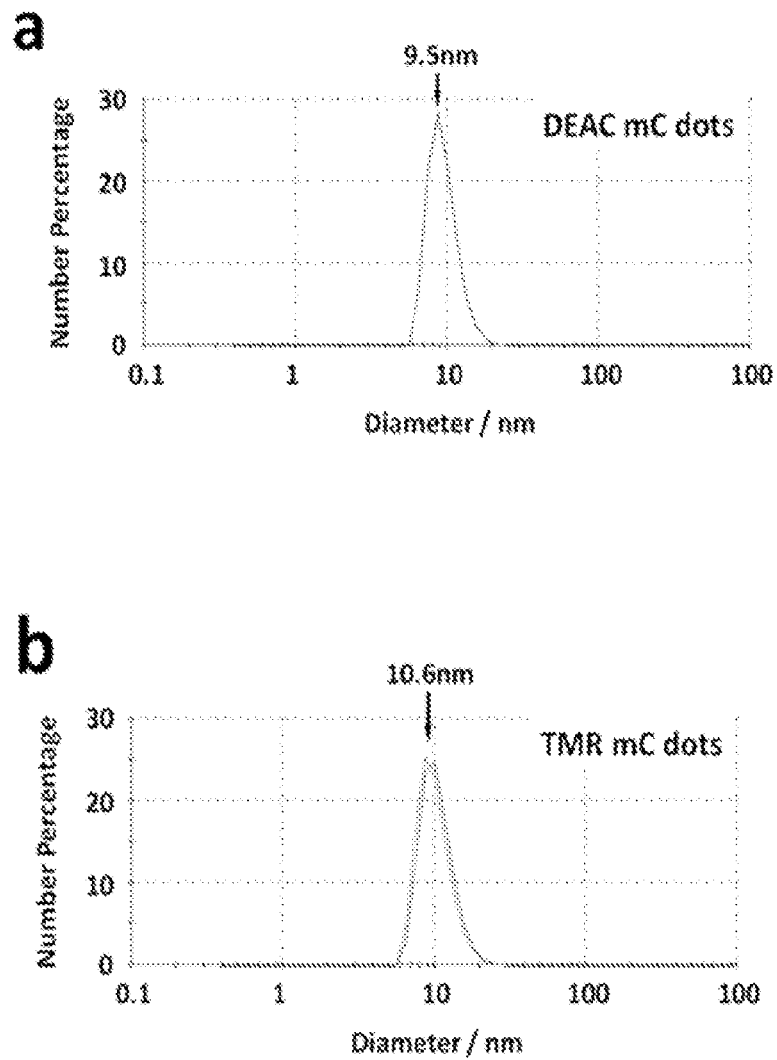
FIG. 18 shows representative characterization of mC dots with different colors. Graphs (a), (c), (e) and (g) display characterization results for DEAC labeled mC dots. Graphs (b), (d), (f) and (h) show characterization results for TMR labeled mC dots. Graphs (a) and (b) show DLS measurement results of dye labeled mC dots. Graphs (c) and (d) show the comparison of correlation curves between free dye molecules and dye-labeled mC dots. Graphs (e) and (f) display spectrophotometer and spectrofluorometer measurement results of free dye molecules and dye-labeled mC dots. Displays (g) and (h) show TEM images of dye labeled mC dots.
Figure 18:
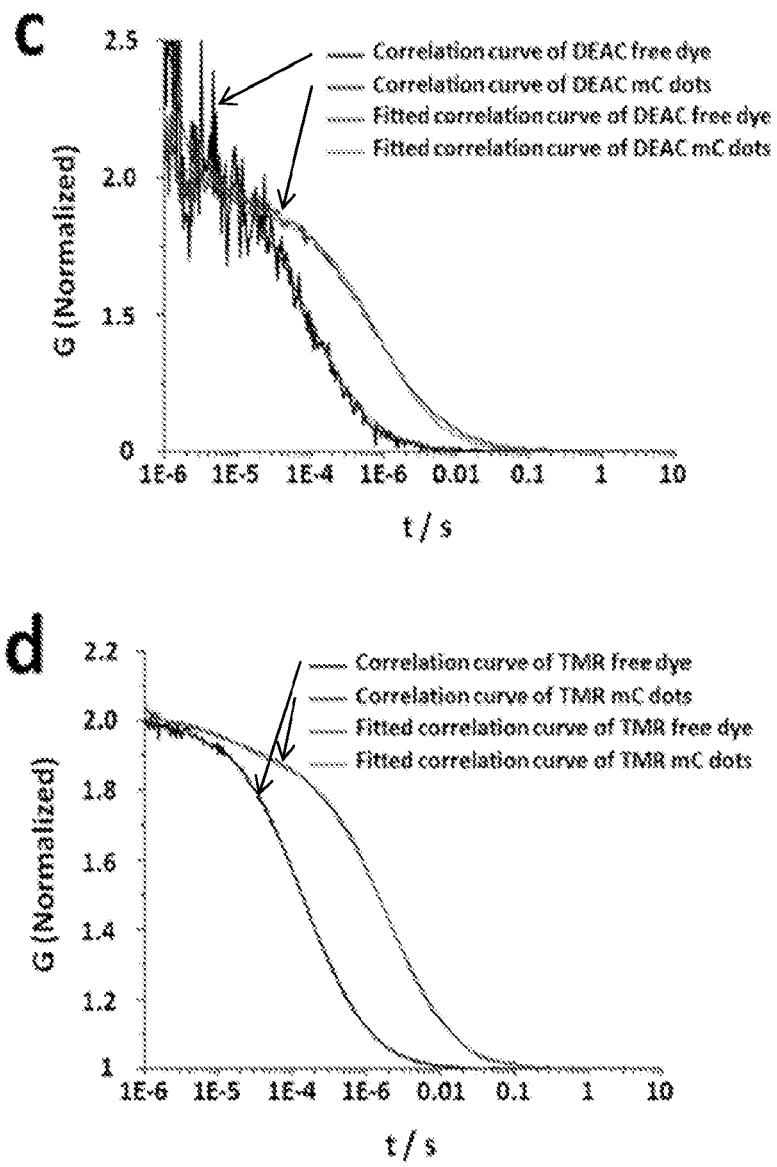
Figure 18:
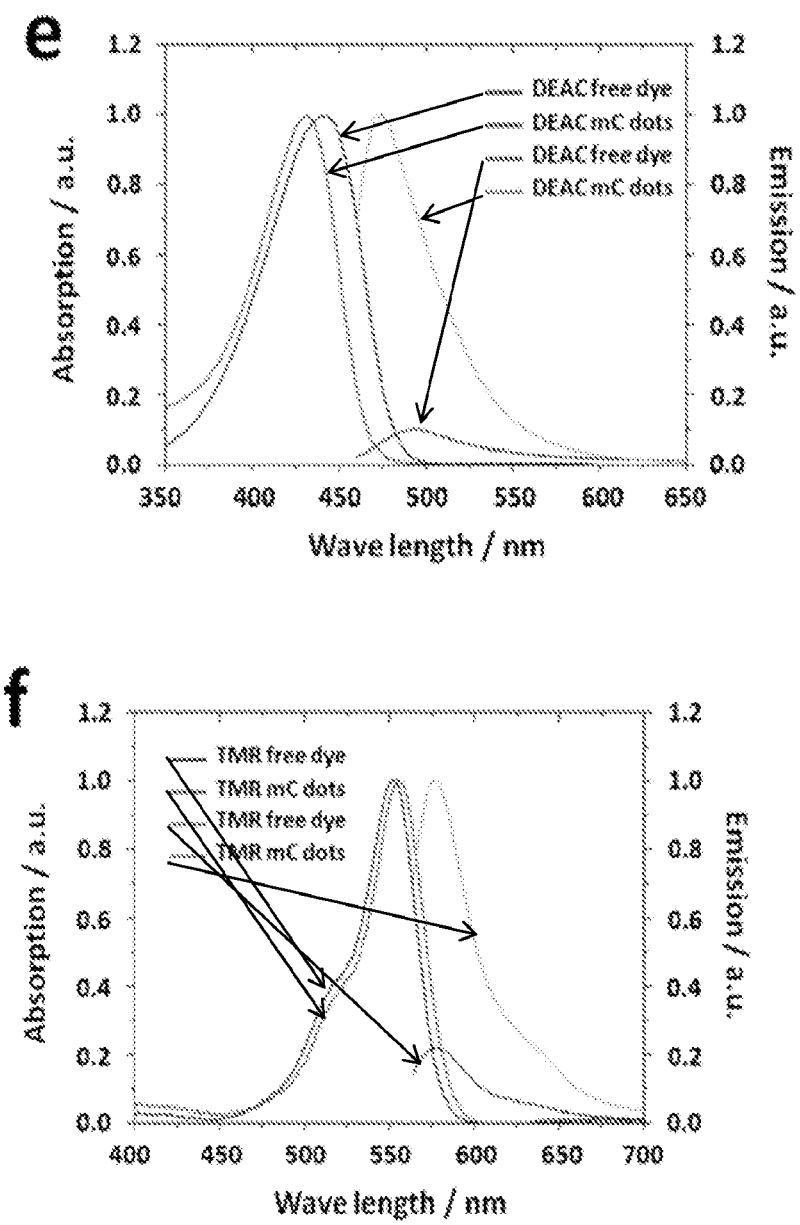
Figure 18:
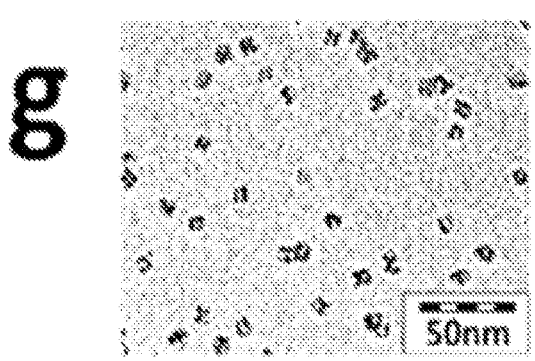
Figure 18:
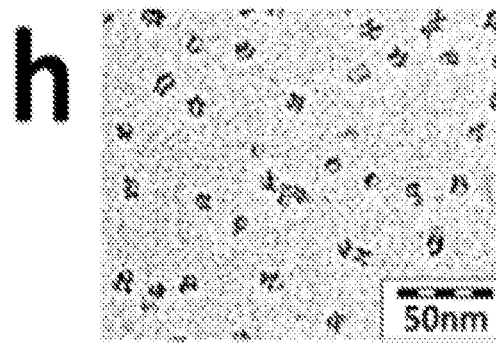

Ultra-small florescent single-pore silica nanoparticles with multiple colors. As discussed above, the particles synthesized in this system with average diameter around 9.3 nm have the most homogeneous single-pore morphology and also potentially the most favorite biodistribution characteristics. In order to further visualize such sub-10 nm single-pore silica nanoparticles in in-vitro and in-vivo experiments, labeling with florescent dyes is highly desirable. To this end the synthesis protocol for the 9.3 nm particles were slightly modified by simultaneously adding silane conjugated dyes and TMOS into the reaction mixture. In this way near infrared (NIR) fluorescent dye Cy5.5 could be successfully encapsulated into the single pore silica nanparticles leading to ultra-small (<10 nm) NIR fluorescent mesoporous silica nanoparticles or, in short, mC dots. Here, this approach is generalized to other colors for multi-color imaging applications. In addition to Cy5.5, two types of dyes with different absorption and emission characteristics, DEAC (blue) and TMR (green), were used for the synthesis of mC dots. From DLS results in FIGS. 18a and 9b, the average hydrodynamic diameters of the DEAC and TMR dye-labeled mC dots were 9.5 nm and 10.6 nm respectively. FIGS. 18g and h show TEM images of the respective mC dots. From these images most of the particles maintained the single-pore morphology. Both, DLS measurements and TEM images, suggest that adding silane-conjugated dyes does not significantly change morphological characteristics of the single-pore silica nanoparticles as compared to the non-fluorescent species. From photospectrometer and fluorometer measurements, FIGS. 18e and f, the absorption/emission maxima of DEAC and TMR free dye are around 440/495 nm and 552/579 nm, respectively, while those of the encapsulated dyes are at 431/475 nm and 554/576 nm, respectively. It is known that encapsulation into silica can enhance the fluorescence intensity due to an increase in quantum efficiency of the dyes. Through absorption matching of free dye and particle solutions and comparing the emission maxima (FIGS. 18e and f), the relative quantum enhancements of DEAC and TMR were determined in the silica particles versus free dye in aqueous solution as 12.3 and 3.5, respectively. In other words, encapsulated in the mC dots a DEAC/TMR dye is 12.3/3.5 times brighter than as a free dye in aqueous solution. In order to further quantify size and brightness characteristics of the mC dots, fluorescent correlation spectroscopy (FCS) for particle characterization was used. FCS is similar to DLS except it uses the fluorescence of the diffusing species rather than the scattered light to generate auto-correlation data. FIGS. 18c and d show comparisons of FCS correlation curves between free dyes and dye-labeled mC dots for DEAC and TMR, respectively. In both cases the FCS correlation curves of the particles are shifted to longer times due to the longer times the larger particles need to diffuse through the same focal observation volume. FCS derived particle diameters for DEAC free dye/DEAC based mC dot and TMR free dye/TMR based mC dot are 1.4/9.7 nm and 1.6/, 13.2 nm, respectively. This is in reasonable agreement with the DLS results, vide-supra, verifying that the silica particles detected in DLS are successfully labeled with dye. Furthermore, FCS measurements also provide the concentration of the diffusing species. By combining this information with results of static optical measurements shown in FIGS. 18e and f, one can derive the average number of dyes per particle, which was 1.2 and 2.1 for DEAC and TMR labeled C dots, respectively. According to studies on structure-photophysical property correlations of C dots, the high quantum enhancements observed here for TMR, and in particular DEAC labeled mC dots, suggest that the dyes are incorporated inside the silica walls of the mC dots.

This example shows that proper choice of silica precursors (TMOS, dye-conjugated silanes), solvent (water) catalyst (L-lysine, ammonium hydroxide) and reaction conditions (monomer and catalyst concentrations, temperature, time-point of addition of PEG-silane capping agent) leads to control over size and size distribution of ultra-small (<10 nm) CTAB directed mesoporous silica nanoparticles (MSNs) and fluorescent mesoporous silica nanoparticles (mC dots) of various colors, including NIR probes. Key elements of achieving this control are (i) fast hydrolysis (by means of TMOS as monomer), (ii) slow condensation (by means of moderate temperatures and low monomer/catalyst concentrations) and (iii) quenching of particle growth by addition of PEG-silane as a capping agent. The latter simultaneously achieves steric stabilization of particles for work in high-salt containing physiological conditions. Results establish access to uniform, sub-10 nm, single pore fluorescent silica nanoparticles (mC dots) with potential application as a theranostic materials platform with rapid renal excretion.

By controlling the particle growth rate and quenching the growth at appropriate time-points, average particle diameters can be precisely tailored from around 6 nm to larger than 15 nm with increments below 1 nm. Furthermore, through analyzing particle diameter distributions and number of pores per particle distributions, it was found that the synthesis batch with average particle diameter around 9.3 nm had the most homogeneous single-pore morphology. The associated size distribution matches the established size window for favorable renal excretion and biodistribution characteristics of PEG-ylated nanoparticles. This approach enables the isolation and characterization of species at the very early stages of mesoporous silica nanoparticle formation. Varying the alkyl chain length of the surfactant, e.g. between C12 and C20, further enables tailoring of pore size as well as overall particle size.

Figure 22:
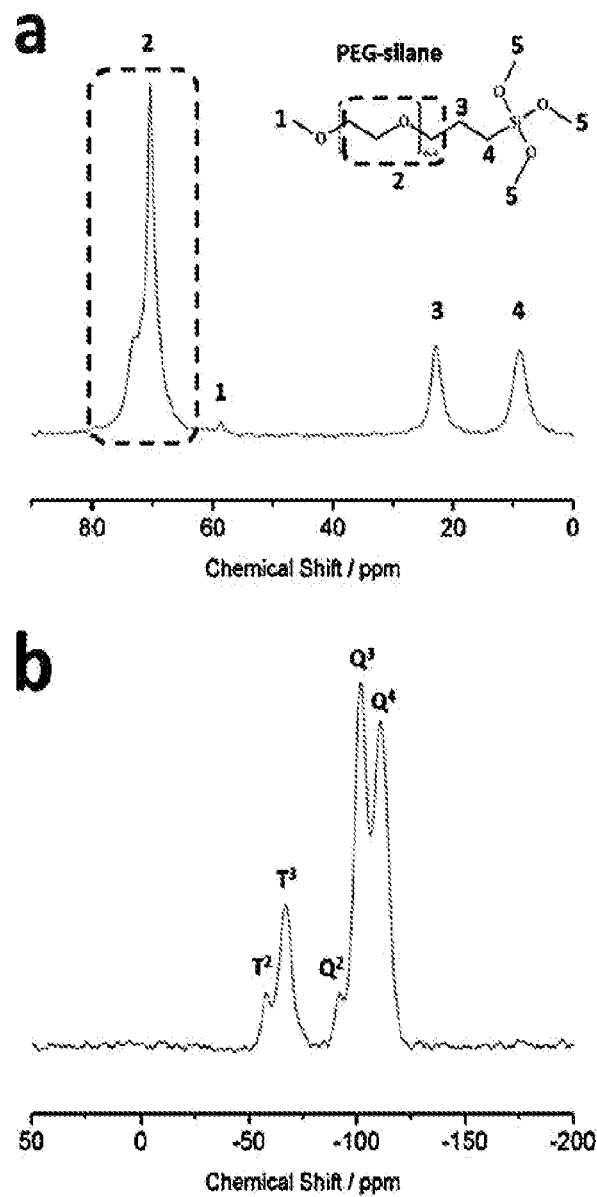
FIG. 22 shows an example of a solid state NMR spectra of 9.3 nm mesoporous silica particles. (a) $^{13}$C solid state NMR spectrum. (b) $^{29}$Si solid state NMR spectrum.

Local Structure and Long-Term Stability of Ultra small Single Pore Silica Nanoparticles. In the study mC dots were already characterized via liquid $^1$H NMR to demonstrate successful CTAB removal as well as the presence of PEG chains on the particle surface. CTAB removal was further corroborated in our first study by nitrogen sorption/desorption measurements. To reveal local structure, here the 9.3 nm single pore particles were subjected to $^{13}$C and $^{29}$Si solid state NMR characterizations. As shown in FIG. 22a, the $^{13}$C solid state NMR spectrum shows peaks at around 9 ppm, 23 ppm, 59 ppm, 71 ppm, and 73 ppm which correspond to signals from the PEG-silane (see inserted figure). The absence of a peak from the methoxy groups (FIG. 22a, labeled 5), expected at around 50 ppm, indicates complete hydrolysis and suggests condensation of PEG-silane onto the particle surface. Furthermore, the absence of signals in the $^{13}$C solid state NMR spectrum of peaks from CTAB expected at 34, 32, and 29 ppm, respectively, is consistent with liquid NMR results (vide supra) confirming its complete removal. The $^{29}$Si solid state NMR spectrum in FIG. 22b shows five peaks. The peaks at around −111 ppm, −102 ppm, and −92 ppm correspond to $Q^4$ $(Si(OSi)_4)$, $Q^3$ $(Si(OSi)_3(OH))$, and $Q^2$ $(Si(OSi)_2(OH)_2)$ groups. The peaks at around −67 ppm and −58 ppm correspond to $T^3$ (R—Si $(OSi)_3$) and $T^2$ (R—Si$(OSi)_2$(OH)) groups. The presence of T groups in addition to Q groups further indicates the condensation of PEG-silane on the particle surface. Considering the particles were dialyzed using a dialysis membrane with 10 k molecular weight cut off before NMR characterization, self-condensed PEG-silane should have been washed away from this sample. For this reason, the T groups actually represent the PEG-silane which condenses onto the particles and confirm the formation of a PEG layer on the silica nanoparticles.

Figure 23:
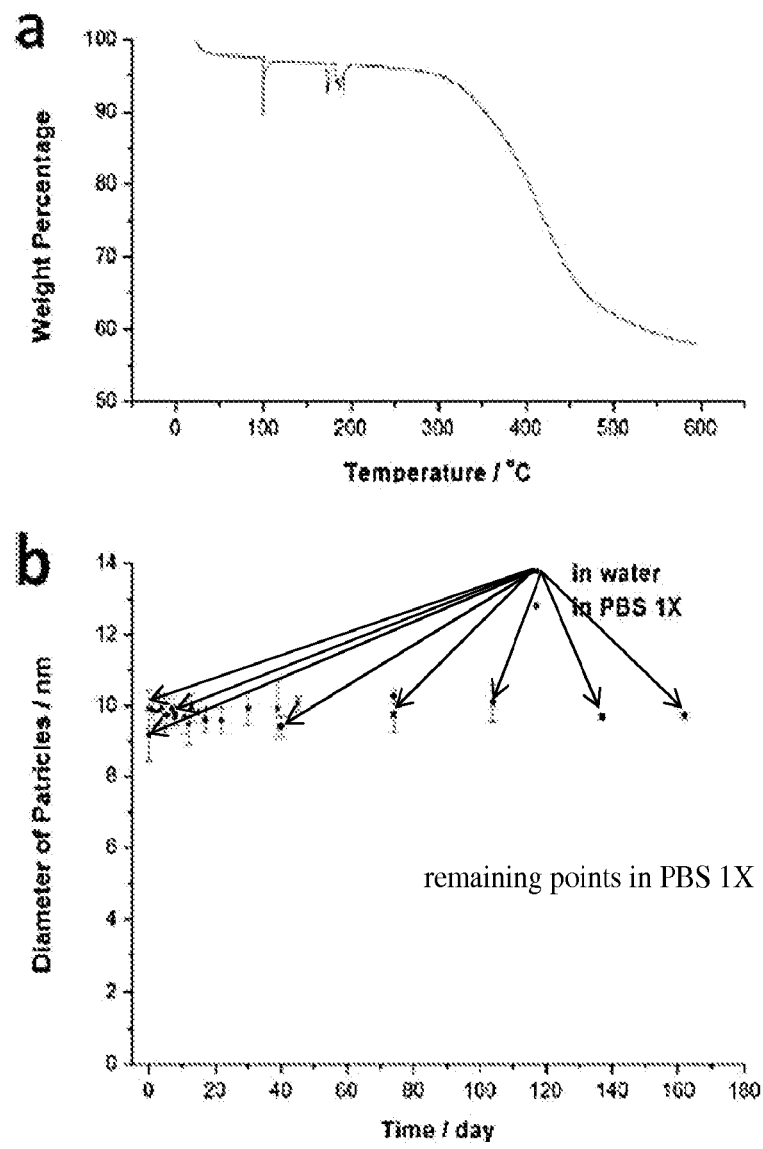
FIG. 23 shows an example of a) TGA of dried 9.3 nm single pore silica nanoparticles. (b) Long-term stability test of 9.3 nm single pore silica nanoparticles in both PBS 1× and DI water measured by DLS.

To quantitatively characterize the density of PEG chains on the particle surface, 9.3 nm single pore particles were subjected to TGA. From FIG. 23a, around 58 wt % of inorganic material (silica) remained as temperatures increased from room temperature to 600° C., while around 40 wt % of organic components (mostly PEG) were burned away. The number of chains per particle and the surface density of PEG chains can then be estimated by simplifying the morphology of the 9.3 nm (hydrodynamic diameter)

single pore particles as tubes with 8 nm outer diameter, 3 nm inner diameter, and 8 nm length. The density of dense silica nanoparticle is between 1.4 to 2.1 g/cm$^3$. Using the lowest density of silica 1.4 g/cm$^3$ in calculation, there are at least 400 PEG chains per particle, and the PEG chains surface density is about 1.6 PEGs/nm$^2$. Considering the surface density of native silanol groups on bare silica is 4.9/nm$^2$, this number suggests that the surface of the single pore particles is almost fully covered by PEG chains. This is consistent with the zeta-potential of these particles measured in PBS 1× (pH 7.5) as −3.4 mV that is very close to zero, despite a very short PEG chain length. For a 10 mL reaction, around 15-18 mg of powder of the 9.3 nm dialyzed particles were collected after drying using a rotary evaporator, of which 58 wt % or 10 mg was silica. Considering 0.22 mmol of TMOS were added into the 10 mL reaction in theory generating about 14 mg of silica at 100% yield, the estimated yield of the reaction is about 71%. Losses in yield could, for example, be the result of premature termination of the reaction by addition of PEGsilane.

Via PEGylation the particles are sterically stabilized after synthesis for in vivo applications. To test the long-term stability of these ultra small mesoporous particles in physiologically relevant media, the 9.3 nm single pore particles were transferred into PBS 1× (pH 7.5), and the hydrodynamic particle size was monitored over several months via DLS. From FIG. 23b, in PBS 1× the average hydrodynamic particle diameter increased to 9.7 nm and remained close to this value for more than two months. Furthermore, in DI water the particles retained their initial size for almost half a year, see FIG. 23b. These data demonstrate that particles neither degrade nor aggregate on these time scales corroborating the stable PEGylation protocol developed here.

Example 3

This example shows ultra small sub-10 nm fluorescent single-pore silica nanoparticles, referred as mesoporous mC dots. The ultra small size and homogeneous porosity endow these materials with the potential to serve as the novel inorganic theranostic nanomaterials. As the first step of the development of cargo loading/release mechanisms, our group quantitatively studied the pore accessibility and capacity of mC dots through fluorescence cross-correlation spectroscopy (FCCS) and absorbance optical characterizations. The results suggest the pores of mC dots are accessible and could be used to load molecular cargos.

Figure 24:
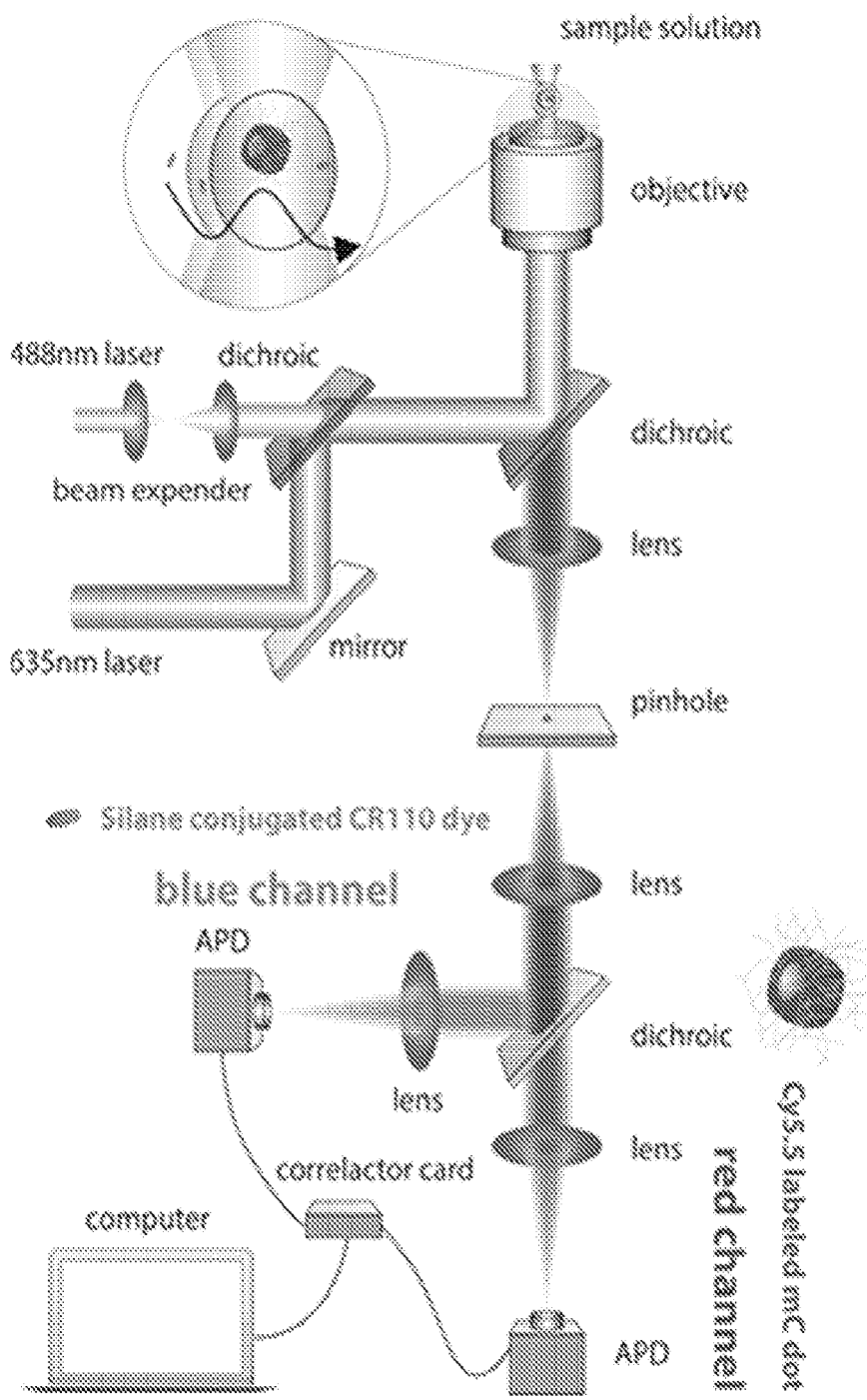
FIG. 24. Setting up FCCS. Two diode pumped solid state laser lines illuminates the sample; 488 nm laser channel monitors the diffusion of CR110 dye and 633 nm laser channel monitors the diffusion of Cy5.5 labeled mC dots. The focal spots of the two channels overlap for cross-correlation measurements. The detected fluorescent light is split by a dichroic behind the collimating lens and focused onto two different avalanche photodiode detectors (APD). The signals are correlated online by a correlate card associated with a personal computer.
Figure 25:
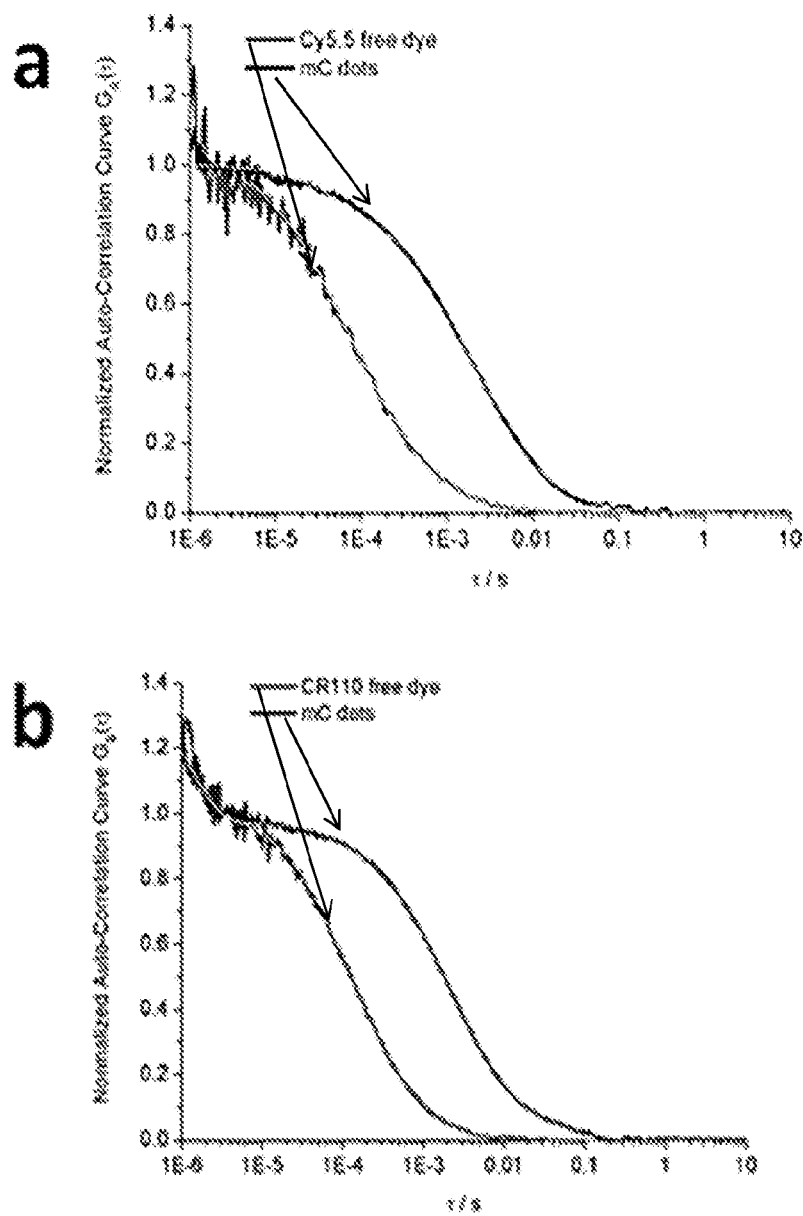
FIG. 25 shows an example of a) normalized red channel auto-correlation curves of Cy5.5 free dye and Cy5.5 labeled mC dots, with fits. b) Normalized blue channel auto-correlation curves of CR110 free dye and CR110 dye loaded by mC dots, with fits. c) Normalized absorbance spectra of c) CR110 and Cy5.5 free dye and d) CR110 loaded mC dots with occupied and unoccupied pores.
Figure 25:
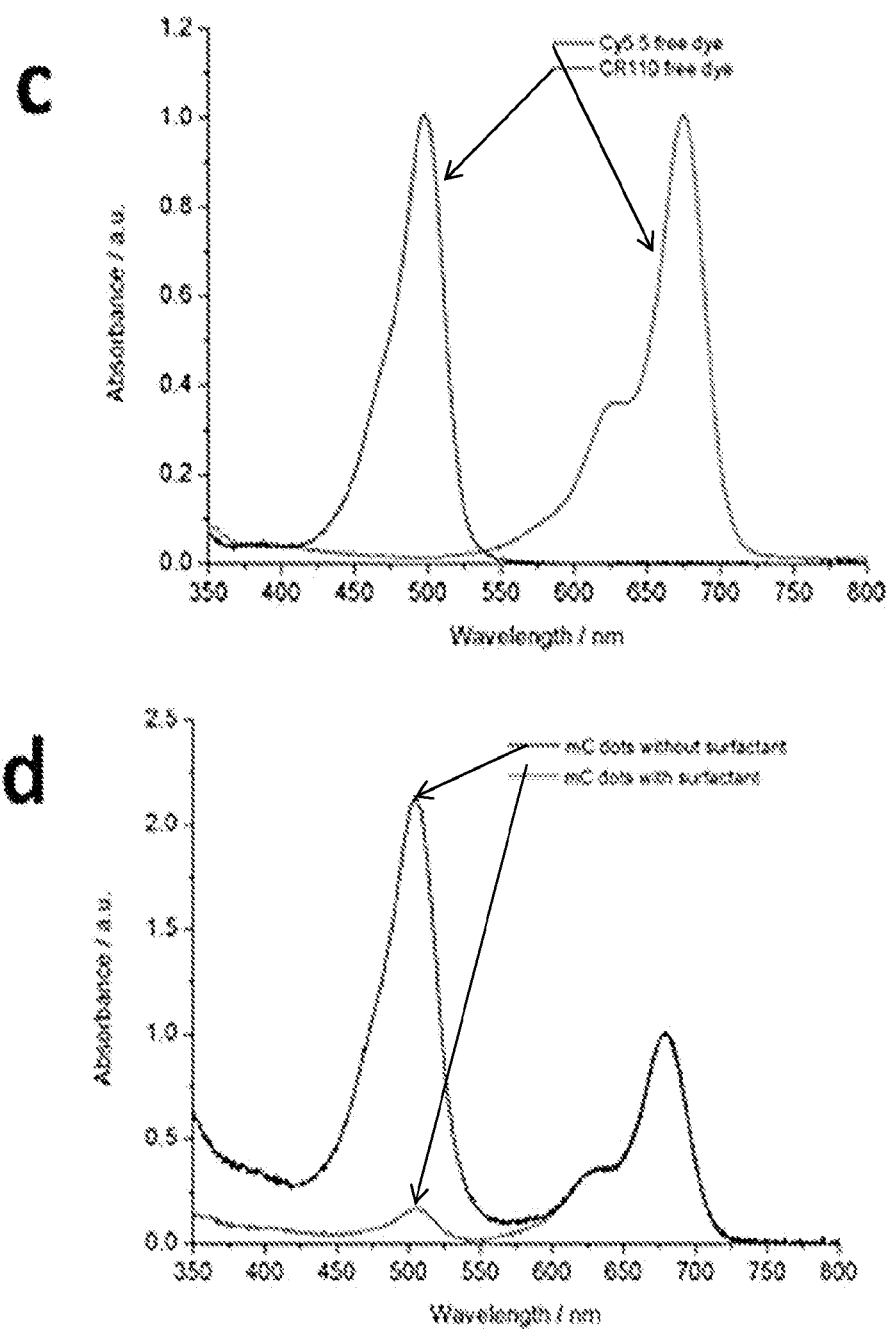

Cy5.5 labeled mC dots with average diameter around 9.3 nm were synthesized according to our previous publications. CR110 fluorescent dye was first conjugated to amino silane though N-hydroxysuccinimide (NHS) esters amine reaction, and then used as the model of molecular cargos. To load silane conjugated CR110 dye molecules into the pores of mC dots, Cy5.5 labeled mC dots were mixed with silane conjugated CR110 dye under mild base condition overnight. As a result, CR110 dye will condense onto the inner pore bare silica surface of mC dots through silane condensation chemistry. The samples were then dialyzed for six days to fully wash away unreacted CR110 dye. Pore accessibility and capacity of mC dots was then studied by FCCS and absorbance optical characterizations. Shown in FIG. 24, FCCS optical characterization was conducted on a home built FCCS setup. The setup was based on two individual FCS channels with overlapped focal spots. The channel with 635 nm excitation wavelength (red channel) monitors the diffusion of Cy5.5 dye labeled mC dots. And the channel with 488 nm excitation wavelength (blue channel) monitors the diffusion of CR110 dye labeled moieties. As the results, the information, e.g. diffusion constant, hydrodynamic size and brightness per molecule, can be obtained from the auto-correlations of each individual channels. And the information about the co-localization degree of Cy5.5 and CR110 moieties can be obtained from the cross-correlation of these two channels. Shown in FIGS. 25a and b, both of the auto-correlation curves of Cy5.5 labeled CR110 loaded mC dots in the red and blue channels shift to the right in comparison to the free Cy5.5 and CR110 dye. This indicates the diffusion of Cy5.5 and CR110 labeled moieties in the sample solution is slower than the diffusion of Cy5.5 and CR110 free dye. The fitted hydrodynamic diameters of the Cy5.5 and CR110 labeled moieties in the sample solution are 10.5 and 12.5 nm (Table 4), respectively, which are consistent with the expected size of mC dots. These results suggest both of Cy5.5 and CR110 dye in the sample solution were bonded to the silica nanoparticles. It also agrees well with the absorbance spectrum of the sample solution which shows two absorbance peaks at around 680 nm and 500 nm corresponding to Cy5.5 and CR110 absorbance (FIGS. 25c and d). By combining the FCS characterization results and absorbance spectrum, the average numbers of dye molecules per particle could be calculated. Shown in Table 4, each mC dot contains around 2 Cy5.5 dye which agrees well with our previous studies and indicates no aggregation happens during CR110 loading reaction. In addition, each mC dot contains around five CR110 dye. This is consistent with the brightness per particle measurement in which the CR110 loaded mC dot is around five times brighter than one CR110 free dye under 488 nm excitation. These results suggest one mC dot could load around five CR110 molecules. Considering the hydrodynamic diameter of CR110 dye molecule is around 0.9 nm and the pore dimension of mC dots is about 3 nm in diameter and 7 nm in depth, there should still be free space in the pores of mC dots for loading more CR110 molecules. This fairly low pore capacity could be due to the covalent interaction used here for cargo loading. It is very possible that once one silane conjugated CR110 molecule diffuses into the pore and condense onto the inner pore surface, it is immobilized on the pore surface by the covalent bonds and thus sterically prevents other CR110 molecules to diffuse into the pore and get loaded. For this reason, the loading performance greatly depends on the cargo loading mechanisms. When non-covalent interaction was used for molecular cargo loading, e.g. hydrophobicity/hydrophobicity, the loading performance could be significantly increased. Considering the main objective of this experiment is to study the pore accessibility of mC dots, to use the covalent interaction for cargo loading, as indicated here, is one of the simplest and most reliable choices. To compare the performance of different cargo loading/release mechanisms and further optimize the cargo loading conditions is clearly necessary and is currently on going.

TABLE 4

FCS Characterization Results

| | Red Channel | | | | Blue Channel | | | |
|---|---|---|---|---|---|---|---|---|
| | Diffusion Constant ($cm^2s^{-1}$) | Hydrodynamic Diameter (nm) | Brightness per Molecule (kHz) | Dye Equivalents | Diffusion Constant ($cm^2s^{-1}$) | Hydrodynamic Diameter (nm) | Brightness per Molecule (kHz) | Dye Equivalents |
| Free Cy5.5 | 3.3E−06 | 1.2 | 7.5 | 1.2 | — | — | — | — |
| Free CR110 | — | — | — | — | 4.5E−06 | 0.9 | 5.6 | 1.1 |
| mC dots | 3.7E−07 | 10.5 | 14.0 | 1.7 | 3.2E−07 | 12.5 | 27.2 | 4.8 |
| mC dots with occupied pores | 3.9E−07 | 10.1 | 14.0 | 1.5 | 3.3E−07 | 12.1 | 7.2 | 1.4 |

FCCS measurements were conducted to further quantify the pore accessibility of mC dots. Shown in FIG. 26a, in addition to auto-correlation curves of red and blue channels, we can obviously see cross-correlation signal of these two channels. This indicates the colocalization of Cy5.5 and CR110 labeled diffusing moieties. By comparing the height of cross-correlation curve to the heights of auto-correlation curves, the Cy5.5 and CR110 coverage percentage of the mC dot sample were calculated. The Cy5.5 coverage percentage was around 26% while the CR110 coverage percentage was around than 80%. The fairly low Cy5.5 coverage percentage was due to the high negative charge of Cy5.5 dye which prevents the silane conjugated Cy5.5 dye to condense into negative charged silica matrix during particle growth. And this coverage percentage could be increased through optimizing the charge balance during the synthesis reaction. However, since the pore accessibility of mC dots does not really depend on the Cy5.5 encapsulation, this 26% Cy5.5 coverage percentage will not affect the pore accessibility analysis. Indeed the 80% CR110 coverage percentage indicates that around 80% mC dots had loaded at least one CR110 dye molecule. These data further prove the pore accessibility of mC dots and suggest the potential of mC dots for molecular cargo delivery.

Figure 26:
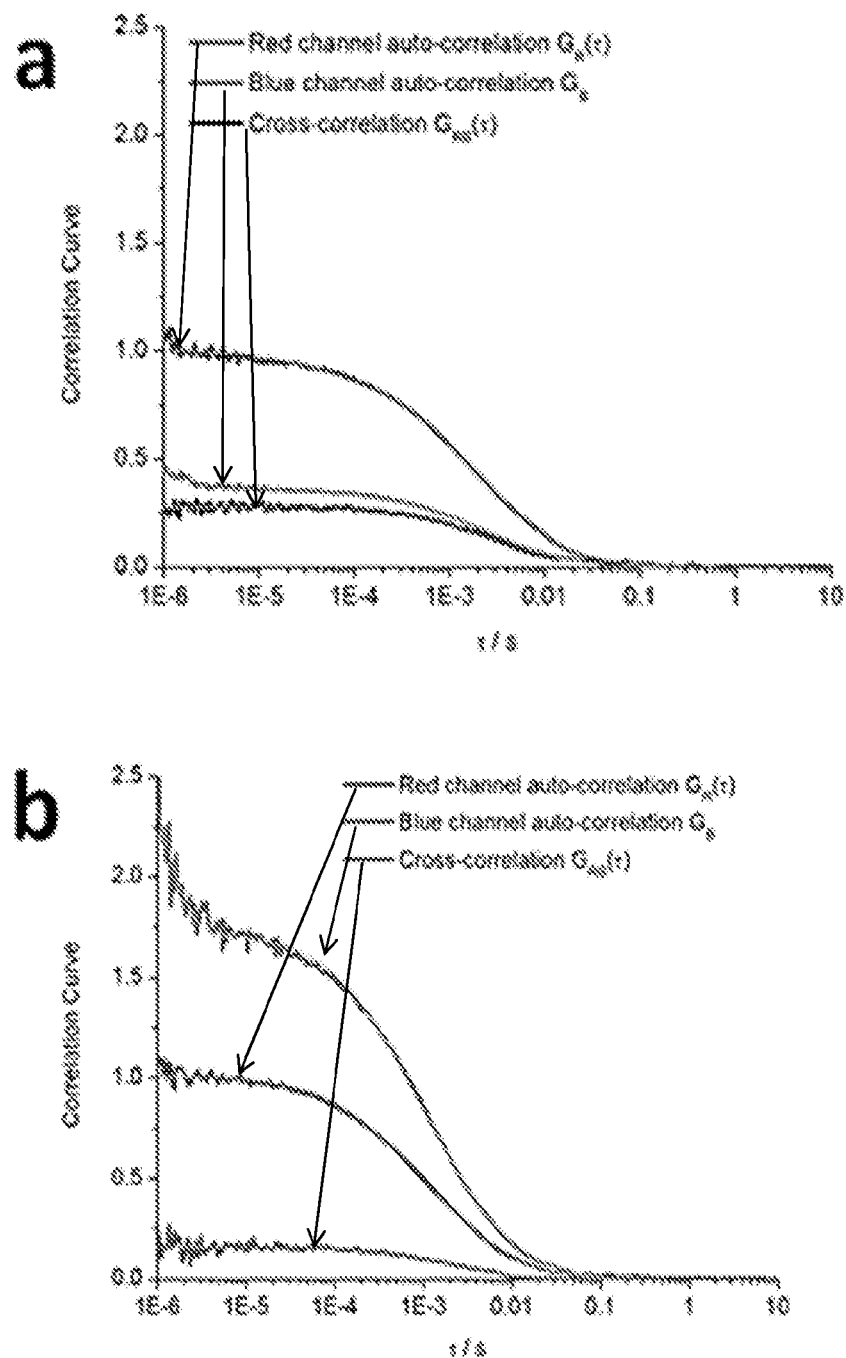
FIG. 26 shows representative red channel auto-correlation, blue channel auto-correlation and cross-correlation curves of mC dots with a) unoccupied and b) occupied pores. All curves are normalized to the red channel auto-correlation curves for comparison.
Figure 27:
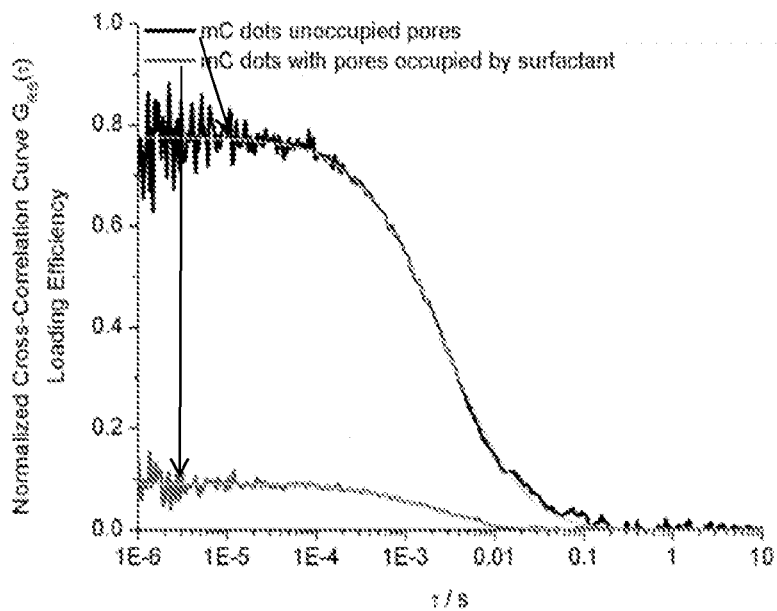
FIG. 27 shows an example of a comparison of cross-correlation curves of mC dots with unoccupied and occupied pores. The curves are normalized to the blue auto-correlation curves for CR110 loading efficiency comparison.

To further confirm the loaded CR110 dye are located inside the pores rather than sitting on the outer surface of mC dots, one control experiment was set up in which the silane conjugated CR110 dye was added into the same batch of mC dots but pores occupied by surfactant. Since cetrimonium bromide (CTAB) surfactant was used as the structure directing agents in mC dot synthesis, CTAB micelles occupy the pores of mC dots throughout the reaction until being extracted by acid in the post-reaction washing steps. In this control experiment, CR110 dye was added into mC dot solution right after mC dot synthesis, before CTAB was extracted. For this reason, the CR110 molecules had much lower possibility to diffuse into the pores and attach to the inner pore surface as the pores were still occupied by CTAB. By comparing the loading performance of mC dots with occupied and unoccupied pores, the locations of loaded CR110 dye could be determined Shown in FIG. 25d, after washing away unreacted CR110 dye, the remaining CR110 peak of mC dots with occupied pores is much lower than that of mC dots with unoccupied pores. This suggests CR110 can be loaded into mC dots only when the pores are unoccupied. FIG. 26a and FIG. 26b compares the FCCS characterization results of mC dots with occupied and unoccupied pores. In these results, all of the correlation curves were normalized according to the red channel auto-correlation curves for comparison. The blue channel auto-correlation curve of mC dots with occupied pores (FIG. 26b) is much higher than that of mC dots with unoccupied pores (FIG. 26a). This indicates the concentration of mC dots which load at least one CR110 dye becomes much lower when the pores are occupied. Also shown in Table 4, the average of number of loaded CR110 dye molecules per particle decreases from 5 to 1.4 as the pores are occupied. The decrease in both the concentration of CR110 loaded mC dots and the amount of loaded CR110 per mC dot indicates the cargo loading performance of mC dots decreases as the pores are occupied by surfactant. The cross-correlation curve of mC dots with occupied pores (FIG. 26b) is lower than that of mC dots with unoccupied pores (FIG. 26a). This indicates the co-localization degree of Cy5.5 and CR110 also becomes lower when the pores of mC dots are occupied. According to FIG. 26b, the Cy5.5 and CR110 dye coverage of mC dots with pores occupied by surfactant was 16% and 9%, respectively. Compared to the 80% CR110 coverage percentage of mC dots with unoccupied pores (FIG. 26a), this 9% CR110 coverage suggests a significant decrease of colocalization degree of Cy5.5 and CR110 in the sample with occupied pores. Shown in FIG. 27, after normalized to the blue channel auto-correlation curves, the heights of cross-correlation curves directly demonstrate the CR110 coverage percentage, in other words, loading efficiency. With open pores, around 80% of mC dots can load at least one CR1110 dye. In comparison, as pores are occupied by surfactants, only around 9% of mC dots are able to load CR110 dye. This is further consistent with the difference in absorbance spectra (FIG. 25c) and the difference in the concentration of CR110 loaded particles (FIGS. 26a and b). The remaining 10% cross-correlation intensity indicates there are still 10% mC dots which could load CR110 dye although the pores are occupied. This could be due to two reasons. First, even the surface of mC dots is covalently covered by polyethylene glycol (PEG) chains; there may still be a few accessible silanol groups on the outer surface for silane conjugated CR110 dye to condense with. Second, although the pores are occupied by CTAB surfactant, the CR110 dye may still have the possibility to diffuse into the pores and get loaded. However, this great decrease of colocalization degree as pores are occupied by surfactant suggests that the location of most of the loaded CR110 in mC dots with unoccupied pores is inside the pores, rather than on the outer surface. This further demonstrates the accessibility of the pores of mC dots.

One interesting phenomenon is that the Cy5.5 dye coverage percentage of mC dots is different in the samples with occupied and unoccupied pores (FIGS. 26a and b). Although the mC dots used in these experiments came from the same batch, the FCCS results suggest the Cy5.5 dye coverage percentage decreases from 26% to 16% when the pores are occupied. This decrease could be due to the dependence of mC dot morphology on particle size. As particle size decreases, the number of pores per particle decreases from multiple to zero. According to our previous publication, the size distribution of mC dots used in this study could range from 12 nm to 6 nm. Within this size region, the pores of the smaller particles are mostly not fully developed. And this poor pore morphology could result in a lower affinity between CTAB micelles and mC dots. For example, the CTAB micelles are more stable inside the well-developed pores on the bigger particles since the pores are better closed, while the CTAB micelles associated with half pore particles are easier to dissociate due to the less sterical protection. As the results, silane conjugated CR110 may have higher possibility to attach to the pore surface of the smaller particles, rather than diffusing into the well-developed pores of the bigger particles which are densely occupied by CTAB micelles. And considering the Cy5.5 encapsulation degree also depends on particle size. The bigger particles have more silica matrix and thus could incorporate more Cy5.5 dye molecules while the smaller particles may not have enough matrix volume to incorporate even one single Cy5.5 molecule. For these reasons, as CTAB surfactant presents, CR110 dye trends to attach to the smaller particles with less developed pores, however, Cy5.5 dye trends to locate in the bigger particles which have more silica matrix volume. In comparison, after the removal of CTAB, bigger particles have larger pore surface area and thus could load more CR110 molecules. And the localization of CR110 matches better with the localization of Cy5.5 and results in higher cross-correlation signal. However, this difference is small compared to the difference of CR110 dye coverage percentage in mC dot samples with occupied and unoccupied pores, and thus will not great affect the pore accessibility analysis here. And indeed the FCCS characterizations could be helpful to quickly determine the dye coverage and thus help to optimize the dye coverage percentage in nanoparticle synthesis for better silica-based fluorescent bio-probes.

The pore accessibility and capacity of mC dots were quantitatively studied through FCCS and absorbance optical characterizations. The results demonstrate the pore accessibility of mC dots. While loading molecular cargo via covalent interaction, each mC dot could load around 5 CR110 molecules averagely and around 80% of mC dots could load at least one CR110 dye molecule. These results could be of importance for the further development of cargo loading/release mechanisms of mC dots.

Zeta-potential. Surface charge and zeta-potential are of great importance in in vivo applications of silica nanoparticles. Bare silica nanoparticles without surface modification have high native negative surface charge which could result in significant disadvantages. First, silica nanoparticles are usually stabilized by the native negative surface charge. The electrostatic repulsion prevents silica nanoparticles from aggregation. However, once injected into the physiological environment, the native surface charge of silica nanoparticles will be quenched by salt ions and bio-molecules and thus causes aggregation. The aggregation of silica nanoparticles could further cause particle accumulation in body and results in long-term toxicity. Second, the native surface charge of silica nanoparticles could also result in protein absorption and unfavorable liver uptake. The biomolecule corona forming on the surface of silica nanoparticles could further cause the loss of tumor targeting functionality. For these reasons, the surface modification of silica nanoparticles with PEG chains for neutral surface charge and sterical stability is always an important step toward favorable biodistribution profile and reliable in vivo stability. PEG chains are used as the terminating agents to quench the particle growth for ultra small silica nanoparticle synthesis. The particles are covalently covered by PEG chains once synthesized, and thus are already sterically stabilized and ready for in vivo studies. To further determine the presence of enough PEG chains on particles surface, we studied the zeta-potential of the PEGylated mC dots. The results suggest that the accurate zeta-potential measurements could be obtained through optimizing the measurement concentration. And the average zeta-potential of mC dots is neutral.

Figure 28:
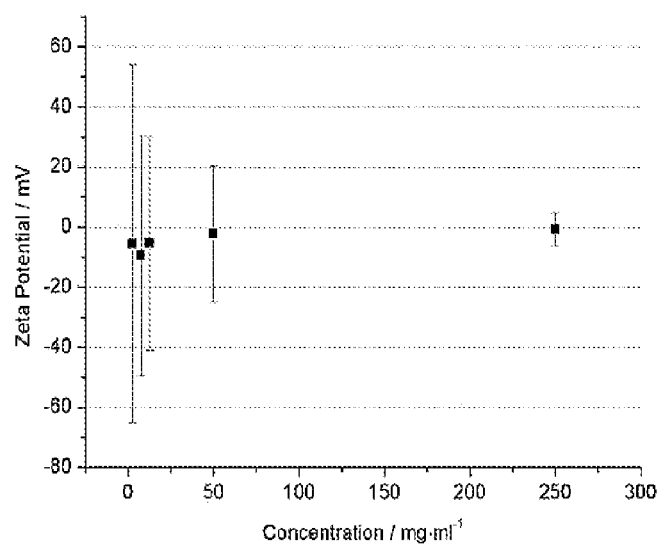
FIG. 28 shows an example of zeta-potential measurement results of mC dots at different concentrations. All data points were measured by three times and the results were averaged. The deviation was reported by Malvern Zetasizer facility based on the distribution of zeta-potential.

The typical way to measure zeta-potential is dynamic light scattering (DLS). The zeta-potential of mC dots were measured via dynamic light scattering (DLS) using a Malvern Zetasizer facility. Shown in FIG. 28, the zeta-potential of as made mC dots with concentration around 2-3 mg/ml is −5.6 mV with deviation 59.6 mV. Considering that the surface with zeta-potential between −10 mV to +10 mV could be considered as the neutral surface, the average zeta-potential −5.6 mV suggests the successful PEGylation of mC dots. However, the huge deviation associated with the average indicates the low accuracy of the measurements. This low accuracy could be due to the ultra small size and neutral zeta potential of mC dots. As particle size decreases, scattering light intensity of particles decreases and results in lower signal for measurements. For PEGylated particles with neutral zeta-potential, the particles have low response to the external electrified and thus results in even lower signal to noise ratio. mC dots are ultra small sub-10 nm with neutral zeta-potential, and thus the overall signal may not be sufficient for the precise measurement. To increase the measurement accuracy, we increase the signal to noise ratio via up concentrating the mC dot sample solution. Shown in FIG. 28, the deviation significantly decreases as sample concentration increases while the average zeta-potential maintains at slightly below 0. At the sample concentration around 0.25 g/ml, the deviation decreases to 5.6 mV, below 10 mV, and thus gives enough reliability for the results. And the average zeta-potential is −0.7 mV. These results further suggest the successful PEGylation and neutral surface of mC dots. They are also consistent with the long-term stability reported.

Cancer targeting ligands on surface. In order to endow mC dots with cancer targeting functionality, cyclic arginine-glycine-aspartic acid (cRGD) peptides were attached to the surface of mC dots. Heterobifunctional PEGs with NHS ester and maleimido groups was first conjugated with amino silane through NHS ester amine reaction. cRGD peptide was then conjugated to the silane-PEG-mal via cysteine-maleimide linkage. The cRGD-PEG-silane was later attached onto the surface of Cy5 labeled mC dots together with the monofunctional PEG-silane to generate cRGD-labeled mC dots. Number of cRGD per mC dot was characterized through absorbance spectra and FCS.

Figure 29:
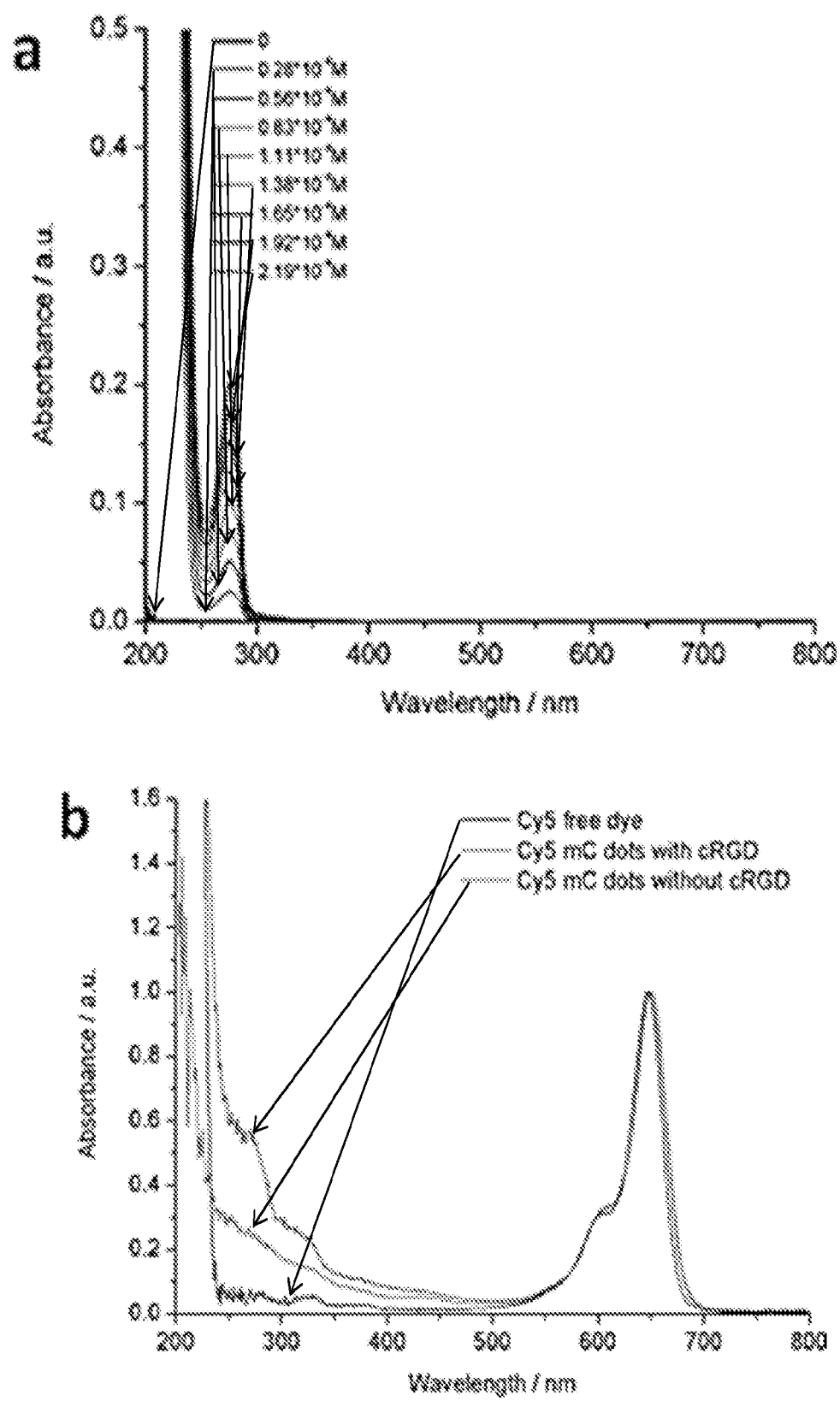
FIG. 29 shows an example of an a) absorbance spectra of cRGD at different concentrations. The insert is the calibration curve of cRGD based on the maximum absorption of cRGD at 275 nm. The extinction coefficient of cRGD at 275 nm is estimated to be 1051 $M^{-1}cm^{-1}$. b) Normalized absorbance spectra of Cy5 free dye, Cy5 mC dots with and without cRGD.

Shown in FIG. 29a, cRGD has absorbance peak at around 275 nm due the tyrosine residue. By measuring the absorbance spectra of cRGD at different concentrations, the extinction coefficient of cRGD could be calibrated (FIG. 29a). The extinction coefficient of cRGD at 275 nm is estimated to be 1051 $M^{-1}$ $cm^{-1}$. Shown in FIG. 29b, after normalized according to the absorbance of Cy5 dye at 650 nm, the spectrum of cRGD labeled mC dots shows additional absorbance peak at 275 nm, which corresponds well to the cRGD residues on particle surface. The small peak at around 325 nm could be due to the quench of native Cy5 dye since the spectrum of Cy5 free dye shows the absorbance peak at the similar wavelength region. The absorption intensity purely due to cRGD at 275 nm of cRGD labeled mC dots could be established via subtracting the spectrum with the spectrum of mC dots without cRGD modification. The concentration of cRGD in the mC dot sample solution could then be estimated using the extinction coefficient of cRGD at 275 nm. The concentration of mC dot in the sample solution could be separately measured by FCS using Cy5 fluorescent signal. And by comparing the concentration of cRGD and the concentration of mC dots, the number of cRGD per mC dot could be calculated. The results suggest each mC dot has around 11 cRGD peptide molecules on surface. The cRGD labeled mC dots show expected tumor targeting functionality in flow cytometry experiments.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A composition comprising polyethylene-glycol (PEG) functionalized mesoporous oxide nanoparticles having an average size of 15 nm or less and having only one pore per mesoporous oxide nanoparticle, and at least 90% of the nanoparticles are within 3 nm of the average size, and at least a portion of a non-pore surface of the functionalized mesoporous oxide nanoparticles is at least partially functionalized with polyethylene glycol groups.

2. The composition of claim 1, wherein the oxide nanoparticles are metal oxide nanoparticles, non-metal oxide nanoparticles, or mixed metal non-metal nanoparticles, or a combination thereof.

3. The composition of claim 1, wherein at least a portion of the individual nanoparticle non-pore surface and at least a portion of the individual nanoparticle pore surface are functionalized.

4. The composition of claim 3, wherein the at least a portion of the nanoparticle non-pore surface and the at least a portion of the pore surface have different functionalization.

5. The composition of claim 3, wherein the at least a portion of the individual nanoparticle non-pore surface is functionalized with a targeting group.

6. The composition of claim 5, wherein the targeting group is a cancer targeting ligand.

7. The composition of claim 1, wherein at least a portion of the nanoparticles comprise a molecular cargo.

8. The composition of claim 7, wherein the molecular cargo is a therapeutic agent or prophylactic agent.

9. The composition of claim 7, wherein the molecular cargo is covalently bonded to at least a portion of the pore surface and/or non-pore surface of the nanoparticles.

10. The composition of claim 9, wherein the molecular cargo is covalently bonded to at least a portion of the pore surface via a linker.

11. The composition of claim 10, wherein the molecular cargo is a fluorescent dye.

12. The composition of claim 7, wherein the molecular cargo is sequestered in a pore of the nanoparticles.

13. The composition of claim 7, wherein the molecular cargo is dispersed in the oxide nanoparticles.

14. The composition of claim 13, wherein the molecular cargo is a fluorescent dye.

15. The composition of claim 1, wherein at least 70% of the mesoporous oxide nanoparticles have only one pore per mesoporous oxide nanoparticle.

16. The composition of claim 1, wherein the PEG functionalized mesoporous oxide nanoparticles have an average size of 10 nm or less.

17. The composition of claim 1, wherein the PEG functionalized mesoporous oxide nanoparticles have an average size of between 6 nm and 10 nm.

18. The composition of claim 1, wherein the average size of the PEG functionalized mesoporous oxide nanoparticles is determined by transmission electron microscopy (TEM).

19. A method of making polyethylene glycol (PEG) functionalized mesoporous oxide nanoparticles having an average size of 15 nm or less and having only one pore per mesoporous oxide nanoparticle, and at least 90% of the nanoparticles are within 3 nm of the average size, and at least a portion of a non-pore surface of the functionalized mesoporous oxide nanoparticles is at least partially functionalized with polyethylene glycol groups comprising the steps of:
   a) forming a reaction mixture in an aqueous solvent having a basic pH comprising:
      i) a surfactant, and
      ii) an oxide precursor,
   b) holding the reaction mixture at a temperature and for a time such that mesoporous oxide nanoparticles are formed;
   c) adding a PEG-functionalized oxide precursor,
   d) holding the reaction mixture at a temperature and for a time such that the PEG-functionalized mesoporous oxide nanoparticles are formed;
   e) optionally, holding the PEG-functionalized mesoporous oxide nanoparticles at a temperature 50° C. to 95° C. for 0.5 to 24 hours;
   f) cooling the reaction mixture to room temperature; and
   g) removing the surfactant from the nanoparticles.

20. The method of claim 19, further comprising the step of functionalizing the nanoparticles.

21. The method of claim 20, wherein the PEG-functionalized nanoparticles are contacted with a fluorescent dye conjugated oxide precursor such that at least a portion of the pores are functionalized with a fluorescent dye.

22. The method of claim 20, wherein the PEG-functionalized nanoparticles are contacted with a molecular cargo such that at least a portion of the molecular cargo is sequestered in the pores of the nanoparticles.

23. The method of claim 19, wherein at least 70% of the mesoporous oxide nanoparticles have only one pore per mesoporous oxide nanoparticle.

24. A method for delivering a molecular cargo to an individual comprising:
   administering to an individual a composition comprising polyethylene-glycol (PEG) functionalized mesoporous oxide nanoparticles having an average size of 15 nm or less and having only one pore per mesoporous oxide nanoparticle, and at least 90% of the nanoparticles are within 3 nm of the average size, and at least a portion of the non-pore surface is at least partially functionalized with polyethylene glycol groups comprising a molecular cargo, wherein at least a portion of the molecular cargo is released in the individual.

25. The method of claim 24, wherein the molecular cargo is a therapeutic agent or prophylactic agent.

26. The method of claim 24, wherein at least 70% of the mesoporous oxide nanoparticles have only one pore per mesoporous oxide nanoparticle.

* * * * *

UNITED STATES PATENT AND TRADEMARK OFFICE
CERTIFICATE OF CORRECTION

PATENT NO. : 10,732,115 B2
APPLICATION NO. : 14/410223
DATED : August 4, 2020
INVENTOR(S) : Wiesner et al.

Page 1 of 1

It is certified that error appears in the above-identified patent and that said Letters Patent is hereby corrected as shown below:

In the Claims

Column 37, Line 64, in Claim 12:
"The composition of 7"
Should read:
--The composition of claim 7--.

Signed and Sealed this
First Day of December, 2020

Andrei Iancu
*Director of the United States Patent and Trademark Office*